(12) United States Patent
Jirgensons et al.

(10) Patent No.: US 7,598,384 B2
(45) Date of Patent: Oct. 6, 2009

(54) TETRAHYDROQUINOLINONES AND THEIR USE AS ANTAGONISTS OF METABOTROPIC GLUTAMATE RECEPTORS

(75) Inventors: Aigars Jirgensons, Riga (LV); Christopher Graham Raphael Parsons, Nidderau (DE); Ieva Jaunzeme, Riga (LV); Ivars Kalvinsh, Salaspils (LV); Markus Henrich, Wetzlar (DE); Maksims Vanejevs, Riga (LV); Tanja Weil, Heidelberg (DE); Valerjans Kauss, Riga (LV); Wojciech Danysz, Nidderau (DE)

(73) Assignee: Merz Pharma GmbH & Co. KGAA, Frankfurt am Main (DE)

( * ) Notice: Subject to any disclaimer, the term of this patent is extended or adjusted under 35 U.S.C. 154(b) by 561 days.

(21) Appl. No.: 11/066,899

(22) Filed: Feb. 25, 2005

(65) Prior Publication Data
US 2005/0197361 A1 Sep. 8, 2005

Related U.S. Application Data

(60) Provisional application No. 60/548,788, filed on Feb. 27, 2004.

(51) Int. Cl.
*C07D 215/38* (2006.01)
(52) U.S. Cl. .................................... 546/159; 546/153
(58) Field of Classification Search .............. 546/153, 546/159
See application file for complete search history.

(56) References Cited

U.S. PATENT DOCUMENTS

| | | | | |
|---|---|---|---|---|
| 5,110,815 A | * | 5/1992 | Effland et al. | 514/228.2 |
| 5,216,164 A | * | 6/1993 | Effland et al. | 546/157 |
| 5,310,914 A | * | 5/1994 | Effland et al. | 546/157 |
| 6,350,749 B1 | * | 2/2002 | Shiraishi et al. | 514/248 |
| 6,472,408 B1 | | 10/2002 | Carlier et al. | |

FOREIGN PATENT DOCUMENTS

| | | |
|---|---|---|
| DE | 2001572 | 7/1971 |
| DE | 2449030 | 5/1976 |
| FR | 2287224 | 5/1976 |
| WO | WO 88/02251 | 4/1988 |
| WO | WO 02/28837 | 4/2002 |
| WO | WO 03/082350 | 10/2003 |

OTHER PUBLICATIONS

Fink, J Med Chem, vol. 38(18), pp. 3645-3651, 1995.*
*International Search Report for International Application No. PCT/GB2005/00717*, Sep. 16, 2005.
Dostenko, et al., *Russ. Chem. Bull., Int. Ed.*, 2002, 51, 1556-1561.
Pitts, et al., *Biorg. Med. Chem. Lett.*, 1998, 8, 307-312.
Schroeder, et al., *Eur. J. Med. Chem.—CHIMICA Therapeutica*, 1979, 14, 309-315.
Shanazarov, et al., *Khimiya Geterotsiklicheskikh Soedinenii*, 1991, 1, 86-92.
Haas, et al., *J. Heterocyclic Chem.*, 1981, 18, 619-622.
Schoepp, et al., *Neuropharmacology*, 1999, 38, 1431-1476.
Roedig, et al., *Chem. Ber.*, 1958, 91, 330-339.
Roedig, et al., *Chem. Ber.*, 1960, 93, 2294-2300.
Stankevich et al., *Chem. Heterocycl. Compd.* (Engl.Transl.), 1966, 2, 440-442; translated from *Khim. Geterotsikl. Soedin.*, 1966, 2, 583-585.
Gudrinietse, et al., *Latv. PSR Zinat.Akad.Vestis Khim.Ser.*, 1972, 622-623.
Gudrinietse, et al., *Chem. Abstr.*; 1973, 78; 29581m.
Yukhnevich et al., *Latv. PSR Zinat. Akad. Vestis Khim. Ser.*, 1973, 699-704.
Yukhnevich et al., *Chem. Abstr.*, 1974, 80, 82603n.
Junek, et al., *Z. Naturforsch. B*, 1970, 25, 1423-1426.
Katsuri et al., *Tetrahedron*, 1975, 31, 527-531.
Albrecht, et al., *Arch. Pharm.*, 1975, 308, 588-594.
Roth, et al., *Arch. Pharm.*, 1977, 310, 48-55.
Bennett, et al., *J. Heterocycl. Chem.*, 1979, 16, 633-635.
Reimann, et al., *Arch. Pharm.*, 1985, 318, 871-878.
Reimann, et al., *Arch. Pharm.*, 1985, 318, 1105-1115.
Nitta, et al., *Bull. Chem. Soc. Jpn.*, 1990, 63, 932-934.
Murogova, et al., *Pharm.Chem.J.* (Eng/.Transl.), 1990, 24, 633-638.
Gatta, et al., *Heterocycles*, 1992, 34, 991-1004.
Molina, et al., *Tetrahedron*, 1995, 51, 1265-1276.
Fink, et al.; *J. Med. Chem.*, 1995, 38, 3645-3651.
Miyabara, et al., *Heterocycles*, 1999, 51, 983-988.
Pyrko, *Chem. Heterocycl. Compd.*(Engl.Transl.), 1999, 35, 688-694.
Fukumoto, et al., *J. Med. Chem.* 2002, 45, 3009-3021.
Okada, et al., *Heterocycles*, 1997, 46, 129-132.
Lopez-Calle, et al., *Liebigs Ann. Org. Bioorg. Chem.*, 1996, 11, 1855-1866.
Carlier, et al., *Angew. Chem. Int. Ed. Eng.*, 2000, 112, 1845-1847.
Kantlehner, et al., *J. Prakt. Chem. / Chem.-Ztg.*, 1998, 340, 408-423.

* cited by examiner

*Primary Examiner*—D. Margaret Seaman
(74) *Attorney, Agent, or Firm*—Hueschen and Sage

(57) ABSTRACT

The invention relates to tetrahydroquinolinone derivatives as well as their pharmaceutically acceptable salts. The invention further relates to a process for the preparation of such compounds. The compounds of the invention are group I mGluR antagonists and are therefore useful for the control and prevention of acute and/or chronic neurological disorders.

77 Claims, No Drawings

TETRAHYDROQUINOLINONES AND THEIR USE AS ANTAGONISTS OF METABOTROPIC GLUTAMATE RECEPTORS

FIELD OF THE INVENTION

The present invention is concerned with novel metabotropic glutamate receptor (mGluR) antagonists, methods for their synthesis and the treatment and/or prevention of neurological disorders.

BACKGROUND OF THE INVENTION

Neuronal stimuli are transmitted by the central nervous system (CNS) through the interaction of a neurotransmitter released by a neuron, which neurotransmitter has a specific effect on a neuroreceptor of another neuron.

L-glutamic acid is considered to be the major excitatory neurotransmitter in the mammalian CNS, consequently playing a critical role in a large number of physiological processes. Glutamate-dependent stimulus receptors are divided into two main groups. The first group comprises ligand-controlled ion channels whereas the second comprises metabotropic glutamate receptors (mGluR). Metabotropic glutamate receptors are a subfamily of G-protein-coupled receptors (GPCR).

At present, eight different members of these mGluRs are known. On the basis of structural parameters such as sequence homology, the second messenger system utilized by these receptors and their different affinity to low-molecular weight compounds, these eight receptors can be divided into three groups: mGluR1 and mGluR5 belong to group I which couple to phospholipase C and their activation leads to intracellular calcium-ion mobilization. Both mGluR2 and mGluR3 belong to group II and mGluR4, mGluR6, mGluR7 and mGluR8 belong to group III, which couple to adenyl cyclase with their activation causing a reduction in second messenger cAMP and as such a dampening of the neuronal activity.

The presence of Group I mGluR antagonists has been shown to result in a reduced presynaptic release of the neurotransmitter glutamate and consequently, to decrease glutamate-mediated neuronal excitation via postsynaptic mechanisms. Since a variety of pathophysiological processes and disease states affecting the CNS are thought to be due to excessive glutamate induced excitation, group I mGluR antagonists could be therapeutically beneficial in the treatment of CNS diseases.

Therefore, group I mGluR antagonists may be administered to provide neuroprotection in acute and chronic pathological conditions such as: AIDS-related dementia, Alzheimer's disease, Creutzfeld-Jakob's syndrome, bovine spongiform encephalopathy (BSE) or other prion related infections, diseases involving mitochondrial dysfunction, diseases involving β-amyloid and/or tauopathy such as Down's syndrome, hepatic encephalopathy, Huntington's disease, motor neuron diseases such as amyotrophic lateral sclerosis (ALS), multiple sclerosis (MS), olivopontocerebellar atrophy, post-operative cognitive deficit (POCD), Parkinson's disease, vascular and frontal lobe dementia, eye injuries, eye disorders (e.g. glaucoma, retinopathy), head and spinal cord injuries/trauma, hypoglycaemia, hypoxia (e.g. perinatal), ischaemia (e.g. resulting from cardiac arrest, stroke, bypass operations or transplants), seizures/convulsions/epilepsy, glioma and other tumours, inner ear insult (e.g. in tinnitus, sound or drug-induced), L-dopa-induced and tardive dyskinesias, Wilson's disease.

Other indications in this context include a symptomatological effect on the following conditions: addiction (nicotine, alcohol, opiate, cocaine, amphetamine obesity and others), amyotrophic lateral sclerosis (ALS), anxiety and panic disorders, attention deficit hyperactivity disorder (ADHD), restless leg syndrome and hyperactive children, autism, seizures/convulsions/epilepsy, dementia (e.g. in Alzheimer's disease, Korsakoff syndrome, vascular dementia, HIV infections, Down's syndrome), depression (including that resulting from Borna virus infection) and bipolar manic-depressive disorder, drug tolerance e.g. to opioids, dyskinesia (e.g. L-Dopa-induced, tardive dyskinesia or in Huntington's disease), fragile-X syndrome, Huntington's chorea, irritable bowel syndrome (IBS), migraine, multiple sclerosis, muscle spasms, pain (chronic and acute), Parkinson's disease, post traumatic stress disorder, schizophrenia, spasticity, tinnitus, Tourette's syndrome, urinary incontinence and vomiting, Wilson's disease.

THE PRESENT INVENTION

We have determined that certain tetrahydroquinolones are Group I mGluR antagonists. Therefore, these substances may be therapeutically beneficial in the treatment of conditions which involve excessive glutamate induced excitation of the CNS. These substances are preferably administered in the form of a pharmaceutical composition, wherein they are present together with one or more pharmaceutically acceptable diluents, carriers, or excipients.

Tetrahydroquinolinones have been disclosed in the art. For example, Kajigaeshi, Shoji; Shirakawa, Shinsuke; Nishida, Akiko; Noguchi, Michihiko, Chemistry Express (1991), 6(7), 527-30 (CODEN: CHEXEU ISSN:0911-9566. CAN 115: 135894 AN 1991:535894 CAPLUS) disclose 2-Benzylsulfanyl-7,7-dimethyl-5-oxo-5,6,7,8-tetrahydro-quinoline-3-carbonitrile. However, this compound is not demonstrated to have activity as a Group I mGluR antagonist. 2-Benzylsulfanyl-5-oxo-5,6,7,8-tetrahydro-quinoline-3-carbonitrile; 2-(2-Methoxyphenyl)-7,8-dihydro-6H-quinolin-5-one; 2-Benzyloxy-7,8-dihydro-6H-quinolin-5-one; 3-Nitro-7,8-dihydro-6H-quinolin-5-one were disclosed by: John Wyeth and Brother Ltd., UK (WO 9521825); ICI Australia Ltd., Australia; Australian Institute of Marine Science (WO 8802251); Karo Bio AB, Swed. (WO 2004037792); Hoechst-Roussel Pharmaceuticals Inc., USA (EP 489379); Warner-Lambert Company, USA (WO 9834921); The Hong Kong University of Science and Technology, Hong Kong (U.S. Pat. No. 6,472,408); Dotsenko, V. V. et al. East-Ukrainian National University, Luhansk, Ukraine, Russian Chemical Bulletin (2002), 51(8), 1556-1561; Molina, Pedro et al. Fac. Quim., Univ. Murcia, Murcia, Spain, Tetrahedron (1995), 51(4), 1265-76; Ruda, Marcus C et al. Karo Bio AB, Swed., Heterocyclic Communications (2003), 9(6), 571-574; Carlier, Paul R et al. Hong Kong University of Science and Technology, Kowloon, Hong Kong, Angewandte Chemie, International Edition (2000), 39(10), 1775-1777; Fink, David M et al. Hoechst-Roussel Pharmaceuticals Inc., Somerville, USA, Journal of Medicinal Chemistry (1995), 38(18), 3645-51; Marcoux, Jean-Francois et al. Merck & Co., Rahway, N.J., USA, Journal of Organic Chemistry (2001), 66(12), 4194-4199; Hoffman, Jacob M et al. Merck Sharp and Dohme Res. Lab., West Point, USA, Journal of Organic Chemistry (1984), 49(1), 193-5. No metabotropic activity has been demonstrated for these compounds.

OBJECTS OF THE INVENTION

It is an object of the present invention to provide novel pharmaceutical compounds which are tetrahydroquinolone Group I mGluR antagonists and pharmaceutical compositions thereof. It is a further object of the invention to provide a novel method of treating, eliminating, alleviating, palliating, or ameliorating undesirable CNS disorders which involve excessive glutamate induced excitation of the CNS by employing a compound of the invention or a pharmaceutical composition containing the same. An additional object of the invention is the provision of a process for producing the tetrahydroquinolone active principles. Yet additional objects will become apparent hereinafter, and still further objects will be apparent to one skilled in the art.

SUMMARY OF THE INVENTION

What we therefore believe to be comprised by our invention may be summarized inter alia in the following words:

Compounds of Formula IA

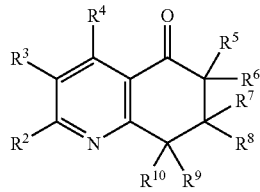

IA wherein
$R^2$ represents $C_{2-6}$alkyl, cyclo$C_{3-12}$alkyl, cyclo$C_{3-12}$alkyl-$C_{1-6}$alkyl, $C_{2-6}$alkenyl, $C_{2-6}$alkynyl, aryl, biaryl, aryl-heteroaryl, heteroaryl-heteroaryl, heteroaryl-aryl, aryl$C_{1-6}$alkyl, aryl$C_{2-6}$alkenyl, aryl$C_{2-6}$alkynyl, heteroaryl, heteroaryl$C_{1-6}$alkyl, heteroaryl$C_{2-6}$alkenyl, heteroaryl$C_{2-6}$alkynyl, 2,3-dihydro-1H-indenyl, $C_{2-6}$alkoxy, hydroxy-$C_{2-6}$alkoxy, cyclo$C_{3-12}$alkoxy, cyclo$C_{3-12}$alkyl-$C_{1-6}$alkoxy, aryloxy, aryl-$C_{1-6}$alkoxy, $C_{1-6}$alkoxy$C_{1-6}$alkyl, $C_{1-6}$alkylthio, $C_{4-6}$alkenylthio, cyclo$C_{3-12}$alkylthio, cyclo$C_{3-12}$alkyl-$C_{1-6}$alkylthio, cyclo$C_{3-12}$alkyl-$C_{3-6}$alkenylthio, $C_{1-6}$alkoxy$C_{1-6}$alkylthio, $C_{1-6}$alkoxy$C_{3-6}$alkenylthio, aryl$C_{3-6}$alkenylthio, heteroaryl$C_{1-6}$alkylthio, $C_{1-6}$alkylsulfonyl, cyclo$C_{3-12}$alkyl-$C_{1-6}$alkylsulfonyl, aryl$C_{1-6}$alkylsulfonyl, $C_{1-6}$alkylamino, di-$C_{1-6}$alkylamino, cyclo$C_{3-12}$alkylamino, $C_1$-$C_6$alkoxy-cyclo$C_3$-$C_{12}$alkylamino, cyclo$C_{3-12}$alkyl-$C_{1-6}$alkylamino, di-$C_{1-6}$alkylamino$C_{1-6}$alkyl, $C_{1-6}$alkoxy-$C_{2-6}$alkylamino, arylamino, aryl$C_{1-6}$alkylamino, N-cyclo$C_{3-12}$alkyl-N—$C_{1-6}$alkylamino, N-aryl-N—$C_{1-6}$alkylamino, N-aryl$C_{1-6}$ alkyl-N—$C_{1-6}$alkylamino, 2-indanylamino, 1,2,3,4-tetrahydroisoquinolin-2-yl, tetrahydrofuryl, pyrrolidino, piperidino, 4-arylpiperidino, 4-heteroarylpiperidino, morpholino, piperazino, 4-$C_{1-6}$alkylpiperazino, 4-arylpiperazino, hexamethyleneimino, benzazepinyl, 1,3-dihydro-2H-isoindol-2-yl, heteroaryl$C_{1-6}$alkoxy, heteroarylamino, heteroaryl$C_{1-6}$alkylamino, —NHC(=O)—$R^{11}$, —NHSO$_2$—$R^{11}$, —NHC(=O)OR$^{11}$, —C(=O)NH—$R^{11}$, —$C_{1-6}$alkyl-C(=O)NH—$R^{11}$, wherein the cyclo$C_{3-12}$alkyl is optionally unsaturated and wherein one carbon atom in the cyclo$C_{3-12}$alkyl moiety may be replaced by an oxygen atom or an NR$^{12}$-moiety;
$R^3$ represents hydrogen, cyano, nitro, halogen, $C_{1-6}$alkyl, CF$_3$, heteroaryl, 2,3-dihydro-1H-indenyl, hydroxy, $C_{1-6}$alkoxy, pyrrolidino, piperidino, morpholino;
$R^4$ represents hydrogen, halogen, nitro, $C_{1-6}$alkoxy, hydroxy-$C_{2-6}$alkoxy;
$R^5$ and $R^6$ which may be the same or different, each independently represent hydrogen, hydroxy, $C_{1-6}$alkyl; cyclo$C_{3-12}$alkyl, $C_{2-6}$alkenyl, $C_{1-6}$alkoxy, $C_{1-6}$alkoxy$C_{1-6}$alkyl, $C_{1-6}$alkylthio, $C_{3-6}$alkenylthio, $C_{1-6}$alkylamino, di-$C_{1-6}$alkylamino, cyclo$C_{3-12}$alkylamino, di-$C_{1-6}$alkylamino$C_{1-6}$alkyl, aryl$C_{1-6}$alkylamino, aryl, aryl$C_{1-6}$alkyl, or aryl$C_{2-6}$alkenyl;
or one of $R^5$ and $R^6$ and one of $R^7$ and $R^8$ together represent —(CH$_2$)$_n$— with n being 3, 4 or 5, while the remaining of $R^5$ and $R^6$ as well as $R^7$ and $R^8$ are both hydrogen;
$R^7$ and $R^8$, which may be the same or different, each independently represent hydrogen, $C_{1-6}$alkyl, cyclo$C_{3-12}$alkyl, $C_{2-6}$alkenyl, cyclo$C_{3-12}$alkyl-$C_{1-6}$alkyl, aryl, aryl$C_{1-6}$alkyl, heteroaryl, or heteroaryl-$C_{1-6}$alkyl;
or $R^7$ and $R^8$ may together represent —(CH$_2$)$_m$— with m being 4, 5 or 6;
$R^9$ and $R^{10}$, which may be the same or different, each independently represent hydrogen, $C_{1-6}$alkyl, hydroxy, or $C_{1-6}$alkoxy;
$R^{11}$ represents hydrogen, $C_{1-6}$alkyl, $C_{2-6}$alkenyl, aryl; aryl$C_{1-6}$alkyl, aryl$C_{2-6}$alkenyl, heteroaryl, heteroaryl$C_{1-6}$alkyl, $C_{1-6}$alkylamino, di-$C_{1-6}$alkylamino, cyclo$C_{3-12}$alkylamino, di-$C_{1-6}$alkylamino$C_{1-6}$alkyl, arylamino, aryl$C_{1-6}$alkylamino, aryl$C_{2-6}$alkenylamino, N-aryl-N—$C_{1-6}$alkylamino, pyrrolidino, piperidino, morpholino, hexamethyleneimino, benzazepinyl, 1,3-dihydro-2H-isoindol-2-yl, cyclo$C_{3-12}$alkyl, or cyclo$C_{3-12}$alkyl$C_{1-6}$alkyl, wherein the cyclo$C_{3-12}$alkyl is optionally unsaturated and wherein one carbon atom in the cyclo$C_{3-12}$alkyl moiety may be replaced by an oxygen atom or an NR$^{12}$-moiety;
$R^{12}$ represents hydrogen, $C_{1-6}$alkyl, aryl, heteroaryl, aryl$C_{1-6}$alkyl or heteroaryl$C_{1-6}$alkyl;
wherein the term "$C_{1-6}$alkyl" represents straight or branched chain alkyl groups; the term "$C_{2-6}$alkenyl" represents straight or branched chain alkenyl groups; the term "$C_{2-6}$alkynyl" represents straight or branched chain alkynyl groups the term "cyclo$C_{3-12}$alkyl" represents monocyclic or bicyclic, or tricyclic alkyl groups including cyclopropyl, cyclobutyl, cyclopentyl, cyclohexyl, bicyclo[2.2.1]heptyl and adamantanyl; the term "aryl" represents phenyl or naphthyl, or phenyl substituted by one or more substituents selected independently from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, and pyridyl; the term "biaryl" represents biphenylene, preferably 4,4'-biphenylene, wherein one or both phenyl rings may optionally be substituted independently by one or more of the substituents independently selected from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, and pyridyl; the term "heteroaryl" represents an aromatic 5-6 membered ring comprising one to four heteroatoms selected from oxygen, sulfur and nitrogen, and a 5-6 membered bicyclic ring comprising one to four heteroatoms selected from oxygen, sulfur and nitrogen fused with a benzene ring or a 5-6 membered ring comprising one to four heteroatoms selected from oxygen, sulfur and nitrogen, wherein the heteroaryl is optionally substituted by one or more substituents selected independently from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, pyridyl, and aryl; heteroaryl may be furyl, thiophenyl, pyrrolyl, oxazolyl, isoxazolyl, thiazolyl, imidazolyl, oxadiazolyl, tetrazolyl, pyridinyl, pyrimidyl, benzofuryl, benzothiophenyl, indolyl, benzimidazolyl, benzoxazolyl, benzothiazolyl, quinolyl and isoquinolyl; and the term "halogen" represents fluorine, chlorine, bromine and iodine;

and optical isomers, polymorphs and pharmaceutically-acceptable acid and base addition salts, hydrates, and solvates thereof;

it being understood that:

$R^2$ may not represent unsubstituted phenyl or naphthyl;

$R^2$ may not represent substituted phenyl having at least one ortho-substituent other than hydrogen, relative to the tetrahydroquinoline ring of formula IA to which the phenyl is attached;

$R^2$ may not represent dimethylamino;

if one of $R^5$ and $R^6$ and one of $R^7$ and $R^8$ together represent —$(CH_2)_n$— with n being 3, 4 or 5, while the remaining of $R^5$ and $R^6$ as well as $R^7$ and $R^8$ are both hydrogen, then $R^2$ may also be halogen;

if $R^3$, $R^4$, $R^5$, $R^6$, $R^7$, $R^8$, $R^9$ and $R^{10}$ all represent hydrogen at the same time, then $R^2$ may not represent $C_{2-6}$alkyl;

if $R^3$ is cyano, then $R^2$ may not represent methylthio or ethylthio;

$R^7$ and $R^8$ may not represent furyl;

and the compound of Formula IA may not represent:

2-Benzyloxy-7,8-dihydro-6H-quinoline-5-one, 2-Phenoxy-7,8-dihydro-6H-quinolin-5-one, 2-(1H-Indol-3-yl)-7,8-dihydro-6H-quinolin-5-one, 2-(1H-Indol-3-yl)-7,7-dimethyl-7,8-dihydro-6H-quinolin-5-one, 2-Thiophen-2-yl-7,8-dihydro-6H-quinolin-5-one, 2-Ethoxy-7,8-dihydro-6H-quinolin-5-one, 7,7-Dimethyl-2-(6-methyl-pyridin-3-ylmethylsulfanyl)-5-oxo-5,6,7,8-tetrahydro-quinoline-3-carbonitrile, 2-(1H-Benzoimidazol-2-ylmethylsulfanyl)-7,7-dimethyl-5-oxo-5,6,7,8-tetrahydro-quinoline-3-carbonitrile, 2-(4-Methoxy-phenyl)-7,8-dihydro-6H-quinolin-5-one, 2-(4-Chloro-phenyl)-7,7-dimethyl-7,8-dihydro-6H-quinolin-5-one, 2-(4-Fluoro-phenyl)-7,8-dihydro-6H-quinolin-5-one, 2-(4-Isopropyl-phenyl)-5-oxo-5,6,7,8-tetrahydroquinoline-3-carbonitrile, or 2-Cyclohexyl-7,8-dihydro-6H-quinolin-5-one such a compound of Formula IA, wherein $R^3$ represents hydrogen, cyano or nitro;

such a compound of Formula IA, wherein $R^4$ represents hydrogen;

such a compound of Formula IA, wherein $R^5$ and $R^6$, which may be the same or different, each independently represent hydrogen or $C_{1-6}$alkyl, and $R^7$ and $R^8$, which may be the same or different, each independently represent hydrogen, $C_{1-6}$alkyl or cyclo$C_{3-12}$alkyl, or wherein one of $R^5$ and $R^6$ and one of $R^7$ and $R^8$ together represent —$(CH_2)_n$— with n being 3, 4 or 5, while the remaining of $R^5$ and $R^6$ as well as $R^7$ and $R^8$ are both hydrogen, or wherein $R^7$ and $R^8$ may together represent —$(CH_2)_m$— with m being 4, 5 or 6;

such a compound of Formula IA, wherein $R^5$ and $R^6$, which may be the same or different, each independently represent hydrogen, methyl, or ethyl;

such a compound of Formula IA, wherein $R^7$ and $R^8$, which may be the same or different, each independently represent hydrogen, methyl, or cyclohexyl.

such compound of Formula IA, wherein one of $R^5$ and $R^6$ and one of $R^7$ and $R^8$ together represent —$(CH_2)_n$— with n being 4, while the remaining of $R^5$ and $R^6$ as well as $R^7$ and $R^8$ are both hydrogen;

such compound of Formula IA, wherein $R^7$ and $R^8$ together represent —$(CH_2)_m$— with m being 5 or 6;

such compound of Formula IA, wherein $R^9$ and $R^{10}$, which may be the same or different, each independently represent hydrogen or $C_{1-6}$alkyl;

such compound of Formula IA, wherein $R^9$ and $R^{10}$, which may be the same or different, each independently represent hydrogen or methyl;

such compound of Formula IA, wherein $R^2$ represents $C_{1-6}$alkylthio, $C_{4-6}$alkenylthio or cyclo$C_{3-12}$alkylthio; $R^3$ represents hydrogen or cyano; $R^4$ represents hydrogen, halogen, nitro or $C_{1-6}$alkoxy; $R^5$ and $R^6$, which may be the same or different, each independently represent hydrogen or $C_{1-6}$alkyl; $R^7$ and $R^8$, which may be the same or different, each independently represent hydrogen, $C_{1-6}$alkyl or cyclo$C_{3-12}$alkyl or $R^7$ and $R^8$ may together represent —$(CH_2)_m$— with m being 4, 5 or 6; and $R^9$ and $R^{10}$, which may be the same or different, each independently represent hydrogen or $C_{1-6}$alkyl;

such compound of Formula IA, wherein $R^2$ represents $C_{2-6}$alkoxy, cyclo$C_{3-12}$alkoxy, cyclo$C_{3-12}$alkyl-$C_{1-6}$alkoxy, aryloxy, aryl-$C_{1-6}$alkoxy or $C_{1-6}$alkoxy$C_{1-6}$alkyl; $R^3$ represents hydrogen or cyano; $R^4$ represents hydrogen, halogen, nitro or $C_{1-6}$alkoxy; $R^5$ and $R^6$, which may be the same or different, each independently represent hydrogen or $C_{1-6}$alkyl; $R^7$ and $R^8$, which may be the same or different, each independently represent hydrogen, $C_{1-6}$alkyl or cyclo$C_{3-12}$alkyl or $R^7$ and $R^8$ may together represent —$(CH_2)_m$— with m being 4, 5 or 6; and $R^9$ and $R^{10}$, which may be the same or different, each independently represent hydrogen or $C_{1-6}$alkyl;

such compound of Formula IA, wherein $R^2$ represents $C_{1-6}$alkylamino, di-$C_{1-6}$alkylamino, cyclo$C_{3-12}$alkylamino, cyclo$C_{3-12}$alkyl-$C_{1-6}$alkylamino, di-$C_{1-6}$alkylamino $C_{1-6}$alkyl, $C_{1-6}$alkoxy-$C_{2-6}$alkylamino, arylamino, aryl$C_{1-6}$alkylamino, N-cyclo$C_{3-12}$alkyl-N—$C_{1-6}$alkylamino, N-aryl-N—$C_{1-6}$alkylamino, N-aryl$C_{1-6}$alkyl-N—$C_{1-6}$alkylamino, wherein the aryl moieties may be unsubstituted or substituted by one or two substituents, each independently selected from methoxy, cyano, halogen, hydroxy, methyl, pyridyl, morpholinyl and piperidinyl; $R^3$ represents hydrogen or cyano; $R^4$ represents hydrogen, halogen, nitro or $C_{1-6}$alkoxy; $R^5$ and $R^6$, which may be the same or different, each independently represent hydrogen or $C_{1-6}$alkyl; $R^7$ and $R^8$, which may be the same or different, each independently represent hydrogen, $C_{1-6}$alkyl or cyclo$C_{3-12}$alkyl, or $R^7$ and $R^8$ may together represent —$(CH_2)_m$— with m being 4, 5 or 6; and $R^9$ and $R^{10}$, which may be the same or different, each independently represent hydrogen or $C_{1-6}$alkyl;

such a compound of Formula IA, wherein $R^2$ represents $C_{2-6}$alkyl, cyclo$C_{3-12}$alkyl, cyclo$C_{3-12}$alkyl-$C_{1-6}$alkyl, $C_{2-6}$alkenyl or aryl$C_{1-6}$alkyl; $R^3$ represents hydrogen, cyano, nitro or morpholino; $R^4$ represents hydrogen, halogen, nitro or C$_{1-6}$alkoxy; R$^5$ and R$^6$, which may be the same or different, each independently represent hydrogen or C$_{1-6}$alkyl; R$^7$ and R$^8$, which may be the same or different, each independently represent hydrogen, C$_{1-6}$alkyl or cycloC$_{3-12}$alkyl, or R$^7$ and R$^8$ may together represent —(CH$_2$)$_m$— with m being 4, 5 or 6; and R$^9$ and R$^{10}$, which may be the same or different, each independently represent hydrogen or C$_{1-6}$alkyl;

such a compound of Formula IA, wherein R$^2$ represents arylC$_{2-6}$alkynyl or heteroarylC$_{2-6}$alkynyl, wherein the aryl moiety may be unsubstituted or substituted by one or two substituents each independently selected from, methoxy, cyano, halogen, hydroxy and methyl and the heteroaryl moiety may be unsubstituted or substituted by one or two substituents each independently selected from phenyl, methoxy, cyano, halogen, hydroxy and methyl; R$^3$ represents hydrogen, cyano or nitro; R$^4$ represents hydrogen; R$^5$ and R$^6$, which may be the same or different, each independently represent hydrogen or C$_{1-6}$alkyl; R$^7$ and R$^8$, which may be the same or different, each independently represent hydrogen, C$_{1-6}$alkyl or cycloC$_{3-12}$alkyl, or R$^7$ and R$^8$ may together represent —(CH$_2$)$_m$— with m being 4, 5 or 6; and R$^9$ and R$^{10}$, which may be the same or different, each independently represent hydrogen or C$_{1-6}$alkyl;

such a compound of Formula IA, wherein R$^2$ represents biaryl or heteroaryl-aryl, wherein the aryl moieties may be unsubstituted or substituted by one or two substituents each independently selected from methoxy, cyano, halogen, hydroxy and methyl; R$^3$ represents hydrogen, cyano or nitro; R$^4$ represents hydrogen; R$^5$ and R$^6$, which may be the same or different, each independently represent hydrogen or C$_{1-6}$alkyl; R$^7$ and R$^8$, which may be the same or different, each independently represent hydrogen, C$_{1-6}$alkyl or cycloC$_{3-12}$alkyl, or R$^7$ and R$^8$ may together represent —(CH$_2$)$_m$— with m being 4, 5 or 6; and R$^9$ and R$^{10}$, which may be the same or different, each independently represent hydrogen or C$_{1-6}$alkyl;

such a compound of Formula IA, wherein R$^2$ represents aryl-heteroaryl or heteroaryl-heteroaryl, wherein the aryl moieties and the heteroaryl moieties, that are not directly attached to the tetrahydroquinoline ring of formula IA, may be unsubstituted or substituted by one or two substituents each independently selected from methoxy, cyano, halogen, hydroxy, methyl, pyridyl, morpholinyl and piperidinyl; R$^3$ represents hydrogen, cyano or nitro; R$^4$ represents hydrogen; R$^5$ and R$^6$, which may be the same or different, each independently represent hydrogen or C$_{1-6}$alkyl; R$^7$ and R$^8$, which may be the same or different, each independently represent hydrogen, C$_{1-6}$alkyl or cycloC$_{3-12}$alkyl or R$^7$ and R$^8$ may together represent —(CH$_2$)$_m$— with m being 4, 5 or 6; and R$^9$ and R$^{10}$, which may be the same or different, each independently represent hydrogen or C$_{1-6}$alkyl;

such a compound of Formula IA, wherein R$^2$ represents halogen, aryl, heteroaryl, arylamino, arylC$_{1-6}$alkylamino, cycloC$_{3-12}$alkyl, piperidino, 4-arylpiperidino, morpholino, piperazino, 4-C$_{1-6}$alkylpiperazino, or 4-arylpiperazino, wherein the aryl moieties and the heteroaryl moieties may be unsubstituted or substituted by one or two substituents, each independently selected from methoxy, cyano, halogen, hydroxy and methyl; one of R$^5$ and R$^6$ and one of R$^7$ and R$^8$ together represent —(CH$_2$)$_n$— with n being 3, 4 or 5, while the remaining of R$^5$ and R$^6$ as well as R$^7$ and R$^8$ are both hydrogen; R$^3$ represents hydrogen, cyano or nitro; R$^4$ represents hydrogen; and R$^9$ and R$^{10}$, which may be the same or different, each independently represent hydrogen or C$_{1-6}$alkyl;

Moreover, a method-of-treating a living animal, including a human for a condition associated with glutamate induced excitation of the CNS comprising the step of administering to the living animal an amount of an mGluR antagonist selected from those of formula IA

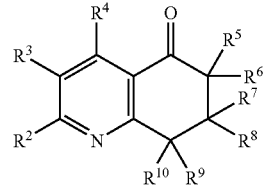

IA wherein

R$^2$ represents C$_{1-6}$alkyl, cycloC$_{3-12}$alkyl, cycloC$_{3-12}$alkyl-C$_{1-6}$alkyl, C$_{2-6}$alkenyl, C$_{2-6}$alkynyl, aryl, biaryl, aryl-heteroaryl, heteroaryl-heteroaryl, heteroaryl-aryl, arylC$_{1-6}$alkyl, arylC$_{2-6}$alkenyl, arylC$_{2-6}$alkynyl, heteroaryl, heteroarylC$_{1-6}$alkyl, heteroarylC$_{2-6}$alkenyl, heteroarylC$_{2-6}$alkynyl, 2,3-dihydro-1H-indenyl, C$_{1-6}$alkoxy, hydroxy-C$_{2-6}$alkoxy, cycloC$_{3-12}$alkoxy, cycloC$_{3-12}$alkyl-C$_{1-6}$alkoxy, aryloxy, aryl-C$_{1-6}$alkoxy, C$_{1-6}$alkoxyC$_{1-6}$alkyl, C$_{1-6}$alkylthio, C$_{4-6}$alkenylthio, cycloC$_{3-12}$alkylthio, cycloC$_{3-12}$alkyl-C$_{1-6}$alkylthio, cycloC$_{3-12}$alkyl-C$_{3-6}$alkenylthio, C$_{1-6}$alkoxyC$_{1-6}$alkylthio, C$_{1-6}$alkoxyC$_{3-6}$alkenylthio, arylC$_{1-6}$alkylthio, arylC$_{3-6}$alkenylthio, heteroarylC$_{1-6}$alkylthio, C$_{1-6}$alkylsulfonyl, cycloC$_{3-12}$alkyl-C$_{1-6}$alkylsulfonyl, arylC$_{1-6}$alkylsulfonyl, C$_{1-6}$alkylamino, di-C$_{1-6}$alkylamino, cycloC$_{3-12}$alkylamino, C$_1$-C$_6$alkoxy-cycloC$_3$-C$_{12}$alkylamino, cycloC$_{3-12}$alkyl-C$_{1-6}$alkylamino, di-C$_{1-6}$alkylaminoC$_{1-6}$alkyl, C$_{1-6}$alkoxy-C$_{2-6}$alkylamino, arylamino, arylC$_{1-6}$alkylamino, N-cycloC$_{3-12}$alkyl-N—C$_{1-6}$alkylamino, N-aryl-N—C$_{1-6}$alkylamino, N-arylC$_{1-6}$alkyl-N—C$_{1-6}$alkylamino, 2-indanylamino, 1,2,3,4-tetrahydroisoquinolin-2-yl, tetrahydrofuryl, pyrrolidino, piperidino, 4-arylpiperidino, 4-heteroarylpiperidino, morpholino, piperazino, 4-C$_{1-6}$alkylpiperazino, 4-arylpiperazino, hexamethyleneimino, benzazepinyl, 1,3-dihydro-2H-isoindol-2-yl, heteroarylC$_{1-6}$alkoxy, heteroarylamino, heteroarylC$_{1-6}$alkylamino, —NHC(=O)—R$^{11}$, —NHSO$_2$—R$^{11}$, —NHC(=O)OR$^{11}$, —C(=O)NH—R$^{11}$, —C$_{1-6}$alkyl-C(=O)NH—R$^{11}$, wherein the cycloC$_{3-12}$alkyl is optionally unsaturated and wherein one carbon atom in the cycloC$_{3-12}$alkyl moiety may be replaced by an oxygen atom or an NR$^{12}$-moiety;

R$^3$ represents hydrogen, cyano, nitro, halogen, C$_{1-6}$alkyl, CF$_3$ heteroaryl, 2,3-dihydro-1H-indenyl, hydroxy, C$_{1-6}$alkoxy, pyrrolidino, piperidino, morpholino;

R$^4$ represents hydrogen, halogen, nitro, C$_{1-6}$alkoxy, hydroxy-C$_{2-6}$alkoxy;

R$^5$ and R$^6$ which may be the same or different, each independently represent hydrogen, hydroxy, C$_{1-6}$alkyl; cycloC$_{3-12}$alkyl, C$_{2-6}$alkenyl, C$_{1-6}$alkoxy, C$_{1-6}$alkoxyC$_{1-6}$alkyl, C$_{1-6}$alkylthio, C$_{3-6}$alkenylthio, C$_{1-6}$alkylamino, di-C$_{1-6}$alkylamino, cycloC$_{3-12}$alkylamino, di-C$_{1-6}$alkylaminoC$_{1-6}$alkyl, arylC$_{1-6}$alkylamino, aryl, arylC$_{1-6}$alkyl, or arylC$_{2-6}$alkenyl;

or one of R$^5$ and R$^6$ and one of R$^7$ and R$^8$ together represent —(CH$_2$)$_n$— with n being 3, 4 or 5, while the remaining of R$^5$ and R$^6$ as well as R$^7$ and R$^8$ are both hydrogen;

R$^7$ and R$^8$, which may be the same or different, each independently represent hydrogen, C$_{1-6}$alkyl, cycloC$_{3-12}$alkyl, C$_{2-6}$alkenyl, cycloC$_{3-12}$alkyl-C$_{1-6}$alkyl, aryl, arylC$_{1-6}$alkyl, heteroaryl or heteroarylC$_{1-6}$alkyl;

or R$^7$ and R$^8$ may together represent —(CH$_2$)$_m$— with m being 4, 5 or 6;

R$^9$ and R$^{10}$, which may be the same or different, each independently represent hydrogen, C$_{1-6}$alkyl, hydroxy, or C$_{1-6}$alkoxy;

R$^{11}$ represents hydrogen, C$_{1-6}$alkyl, C$_{2-6}$alkenyl, aryl; arylC$_{1-6}$alkyl, arylC$_{2-6}$alkenyl, heteroaryl, heteroarylC$_{1-6}$alkyl, C$_{1-6}$alkylamino, di-C$_{1-6}$alkylamino, cycloC$_{3-12}$alkylamino, di-C$_{1-6}$alkylaminoC$_{1-6}$alkyl, arylamino, arylC$_{1-6}$alkylamino, arylC$_{2-6}$alkenylamino, N-aryl-N—C$_{1-6}$alkylamino, pyrrolidino, piperidino, morpholino, hexamethyleneimino, benzazepinyl, 1,3-dihydro-2H-isoindol-2-yl, cycloC$_{3-12}$alkyl, or cycloC$_{3-12}$alkylC$_{1-6}$alkyl, wherein the cycloC$_{3-12}$alkyl is optionally unsaturated and wherein one carbon atom in the cycloC$_{3-12}$alkyl moiety may be replaced by an oxygen atom or an NR$^{12}$-moiety;

R$^{12}$ represents hydrogen, C$_{1-6}$alkyl, aryl, heteroaryl, arylC$_{1-6}$alkyl or heteroarylC$_{1-6}$alkyl;

wherein the term "C$_{1-6}$alkyl" represents straight or branched chain alkyl groups; the term "C$_{2-6}$alkenyl" represents straight or branched chain alkenyl groups; the term "C$_{2-6}$alkynyl" represents straight or branched chain alkynyl groups the term "cycloC$_{3-12}$alkyl" represents monocyclic or bicyclic, or tricyclic alkyl groups including cyclopropyl, cyclobutyl, cyclopentyl, cyclohexyl, bicyclo[2.2.1]heptyl and adamantanyl; the term "aryl" represents phenyl or naphthyl, or phenyl substituted by one or more substituents selected independently from a halogen, trifluoromethyl, C$_{1-6}$alkyl, C$_{2-6}$alkenyl, C$_{1-6}$alkoxy, amino, hydroxy, nitro, cyano, C$_{1-6}$alkoxycarbonyl, C$_{1-6}$alkylamino, di-C$_{1-6}$alkylamino, cyanomethyl, piperidinyl, morpholinyl, and pyridyl; the term "biaryl" represents biphenylene, preferably 4,4'-biphenylene, wherein one or both phenyl rings may optionally be substituted independently by one or more of the substituents independently selected from a halogen, trifluoromethyl, C$_{1-6}$alkyl, C$_{2-6}$alkenyl, C$_{1-6}$alkoxy, amino, hydroxy, nitro, cyano, C$_{1-6}$alkoxycarbonyl, C$_{1-6}$alkylamino, di-C$_{1-6}$alkylamino, cyanomethyl, piperidinyl, morpholinyl, and pyridyl; the term "heteroaryl" represents an aromatic 5-6 membered ring comprising one to four heteroatoms selected from oxygen, sulfur and nitrogen, and a 5-6 membered bicyclic ring comprising one to four heteroatoms selected from oxygen, sulfur and nitrogen fused with a benzene ring or a 5-6 membered ring comprising one to four heteroatoms selected from oxygen, sulfur and nitrogen, wherein the heteroaryl is optionally substituted by one or more substituents selected independently from a halogen, trifluoromethyl, C$_{1-6}$alkyl, C$_{2-6}$alkenyl, C$_{1-6}$alkoxy, amino, hydroxy, nitro, cyano, C$_{1-6}$alkoxycarbonyl, C$_{1-6}$alkylamino, di-C$_{1-6}$alkylamino, cyanomethyl, piperidinyl, morpholinyl, pyridyl, and aryl; heteroaryl may be furyl, thiophenyl, pyrrolyl, oxazolyl, isoxazolyl, thiazolyl, imidazolyl, oxadiazolyl, tetrazolyl, pyridinyl, pyrimidyl, benzofuryl, benzothiophenyl, indolyl, benzimidazolyl, benzoxazolyl, benzothiazolyl, quinolyl and isoquinolyl; and the term "halogen" represents fluorine, chlorine, bromine and iodine;

it being understood that if one of R$^5$ and R$^6$ and one of R$^7$ and R$^8$ together represent —(CH$_2$)$_n$— with n being 3, 4 or 5, while the remaining of R$^5$ and R$^6$ as well as R$^7$ and R$^8$ are both hydrogen, then R$^2$ may also be halogen;

and optical isomers, polymorphs and pharmaceutically-acceptable acid and base addition salts, hydrates, and solvates thereof, which is effective for alleviation of the condition;

such a method wherein the compound is administered in the form of a pharmaceutical composition thereof comprising the compound in combination with one or more pharmaceutically-acceptable diluents, excipients, or carriers;

such a method wherein the condition associated with excessive glutamate induced excitation of the CNS is selected from the group consisting of AIDS-related dementia, Alzheimer's disease, Creutzfeld-Jakob's syndrome, bovine spongiform encephalopathy (BSE) or other prion related infections, diseases involving mitochondrial dysfunction, diseases involving β-amyloid and/or tauopathy such as Down's syndrome, hepatic encephalopathy, Huntington's disease, motor neuron diseases such as amyotrophic lateral sclerosis (ALS), multiple sclerosis (MS), olivopontocerebellar atrophy, postoperative cognitive deficit (POCD), Parkinson's disease, vascular and frontal lobe dementia, eye injuries, eye disorders (e.g. glaucoma, retinopathy), head and spinal cord injuries, trauma, hypoglycaemia, hypoxia (e.g. perinatal), ischaemia (e.g. resulting from cardiac arrest, stroke, bypass operations or transplants), seizures, convulsions, epilepsy, glioma and other tumours, inner ear insult (e.g. in tinnitus, sound or drug-induced), L-dopa-induced and tardive dyskinesias, Wilson's disease.

such a method wherein the condition associated with excessive glutamate induced excitation of the CNS is selected from the group consisting of addiction (nicotine, alcohol, opiate, cocaine, amphetamine obesity and others), amyotrophic lateral sclerosis (ALS), anxiety and panic disorders, attention deficit hyperactivity disorder (ADHD), restless leg syndrome and hyperactive children, autism, seizures, convulsions, epilepsy, dementia (e.g. in Alzheimer's disease, Korsakoff syndrome, vascular dementia, HIV infections, Down syndrome), depression (including that resulting from Borna virus infection) and bipolar manic-depressive disorder, drug tolerance e.g. to opioids, dyskinesia (e.g. L-Dopa-induced, tardive dyskinesia or in Huntington's disease), fragile-X syndrome, Huntington's chorea, irritable bowel syndrome (IBS), migraine, multiple sclerosis, muscle spasms, pain (chronic and acute), Parkinson's disease, post traumatic stress disorder, schizophrenia, spasticity, tinnitus, Tourette's syndrome, urinary incontinence and vomiting, Wilson's disease.

Further, a pharmaceutical composition comprising, together with one or more pharmaceutically acceptable excipients or vehicles, a compound selected from those of Formula IA

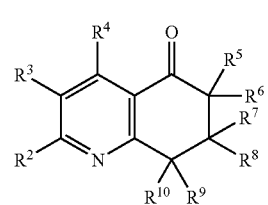

IA wherein
R$^2$ represents C$_{2-6}$alkyl, cycloC$_{3-12}$alkyl, cycloC$_{3-12}$alkyl-C$_{1-6}$alkyl, C$_{2-6}$alkenyl, C$_{2-6}$alkynyl, aryl, biaryl, aryl-heteroaryl, heteroaryl-heteroaryl, heteroaryl-aryl, aryl$C_{1-6}$alkyl, aryl$C_{2-6}$alkenyl, aryl$C_{2-6}$alkynyl, heteroaryl, heteroaryl$C_{1-6}$alkyl, heteroaryl$C_{2-6}$alkenyl, heteroaryl$C_{2-6}$alkynyl, 2,3-dihydro-1H-indenyl, $C_{2-6}$alkoxy, hydroxy-$C_{2-6}$alkoxy, cyclo$C_{3-12}$alkoxy, cyclo$C_{3-12}$alkyl-$C_{1-6}$alkoxy, aryloxy, aryl-$C_{1-6}$alkoxy, $C_{1-6}$alkoxy$C_{1-6}$alkyl, $C_{1-6}$alkylthio, $C_{4-6}$alkenylthio, cyclo$C_{3-12}$alkylthio, cyclo$C_{3-12}$alkyl-$C_{1-6}$alkylthio, cyclo$C_{3-12}$alkyl-$C_{3-6}$alkenylthio, $C_{1-6}$alkoxy$C_{1-6}$alkylthio, $C_{1-6}$alkoxy$C_{3-6}$alkenylthio, aryl$C_{3-6}$alkenylthio, heteroaryl$C_{1-6}$alkylthio, $C_{1-6}$alkylsulfonyl, cyclo$C_{3-12}$alkyl-$C_{1-6}$alkylsulfonyl, aryl$C_{1-6}$alkylsulfonyl, $C_{1-6}$alkylamino, di-$C_{1-6}$alkylamino, cyclo$C_{3-12}$alkylamino, $C_1$-$C_6$alkoxy-cyclo$C_{3-12}$alkylamino, cyclo$C_{3-12}$alkyl-$C_{1-6}$alkylamino, di-$C_{1-6}$alkylamino-$C_{1-6}$alkyl, $C_{1-6}$alkoxy-$C_{2-6}$alkylamino, arylamino, aryl$C_{1-6}$alkylamino, N-cyclo$C_{3-12}$alkyl-N—$C_{1-6}$alkylamino, N-aryl-N—$C_{1-6}$alkylamino, N-aryl$C_{1-6}$alkyl-N—$C_{1-6}$alkylamino, 2-indanylamino, 1,2,3,4-tetrahydroisoquinolin-2-yl, tetrahydrofuryl, pyrrolidino, piperidino, 4-arylpiperidino, 4-heteroarylpiperidino, morpholino, piperazino, 4-$C_{1-6}$alkylpiperazino, 4-arylpiperazino, hexamethyleneimino, benzazepinyl, 1,3-dihydro-2H-isoindol-2-yl, heteroaryl$C_{1-6}$alkoxy, heteroarylamino, heteroaryl$C_{1-6}$alkylamino, —NHC(=O)—$R^{11}$, —NHSO$_2$—$R^{11}$, —NHC(=O)O$R^{11}$, —C(=O)NH—$R^{11}$, —$C_{1-6}$alkyl-C(=O)NH—$R^{11}$, wherein the cyclo$C_{3-12}$alkyl is optionally unsaturated and wherein one carbon atom in the cyclo$C_{3-12}$alkyl moiety may be replaced by an oxygen atom or an N$R^{12}$-moiety;

$R^3$ represents hydrogen, cyano, nitro, halogen, $C_{1-6}$alkyl, $CF_3$, heteroaryl, 2,3-dihydro-1H-indenyl, hydroxy, $C_{1-6}$alkoxy, pyrrolidino, piperidino, morpholino;

$R^4$ represents hydrogen, halogen, nitro, $C_{1-6}$alkoxy, hydroxy-$C_{2-6}$alkoxy;

$R^5$ and $R^6$ which may be the same or different, each independently represent hydrogen, hydroxy, $C_{1-6}$alkyl; cyclo$C_{3-12}$alkyl, $C_{2-6}$alkenyl, $C_{1-6}$alkoxy, $C_{1-6}$alkoxy$C_{1-6}$alkyl, $C_{1-6}$alkylthio, $C_{3-6}$alkenylthio, $C_{1-6}$alkylamino, di-$C_{1-6}$alkylamino, cyclo$C_{3-12}$alkylamino, di-$C_{1-6}$alkylamino$C_{1-6}$alkyl, aryl$C_{1-6}$alkylamino, aryl, aryl$C_{1-6}$alkyl, or aryl$C_{2-6}$alkenyl;

or one of $R^5$ and $R^6$ and one of $R^7$ and $R^8$ together represent —(CH$_2$)$_n$— with n being 3, 4 or 5, while the remaining of $R^5$ and $R^6$ as well as $R^7$ and $R^8$ are both hydrogen;

$R^7$ and $R^8$, which may be the same or different, each independently represent hydrogen, $C_{1-6}$alkyl, cyclo$C_{3-12}$alkyl, $C_{2-6}$alkenyl, cyclo$C_{3-12}$alkyl-$C_{1-6}$alkyl, aryl, aryl$C_{1-6}$alkyl, heteroaryl, or heteroaryl-$C_{1-6}$alkyl;

or $R^7$ and $R^8$ may together represent —(CH$_2$)$_m$— with m being 4, 5 or 6;

$R^9$ and $R^{10}$, which may be the same or different, each independently represent hydrogen, $C_{1-6}$alkyl, hydroxy, or $C_{1-6}$alkoxy;

$R^{11}$ represents hydrogen, $C_{1-6}$alkyl, $C_{2-6}$alkenyl, aryl; aryl$C_{1-6}$alkyl, aryl$C_{2-6}$alkenyl, heteroaryl, heteroaryl$C_{1-6}$alkyl, $C_{1-6}$alkylamino, di-$C_{1-6}$alkylamino, cyclo$C_{3-12}$alkylamino, di-$C_{1-6}$alkylamino$C_{1-6}$alkyl, arylamino, aryl$C_{1-6}$alkylamino, aryl$C_{2-6}$alkenylamino, N-aryl-N—$C_{1-6}$alkylamino, pyrrolidino, piperidino, morpholino, hexamethyleneimino, benzazepinyl, 1,3-dihydro-2H-isoindol-2-yl, cyclo$C_{3-12}$alkyl, or cyclo$C_{3-12}$alkyl$C_{1-6}$alkyl, wherein the cyclo$C_{3-12}$alkyl is optionally unsaturated and wherein one carbon atom in the cyclo$C_{3-12}$alkyl moiety may be replaced by an oxygen atom or an N$R^{12}$-moiety;

$R^{12}$ represents hydrogen, $C_{1-6}$alkyl, aryl, heteroaryl, aryl$C_{1-6}$alkyl or heteroaryl$C_{1-6}$alkyl;

wherein the term "$C_{1-6}$alkyl" represents straight or branched chain alkyl groups; the term "$C_{2-6}$alkenyl" represents straight or branched chain alkenyl groups; the term "$C_{2-6}$alkynyl" represents straight or branched chain alkynyl groups the term "cyclo$C_{3-12}$alkyl" represents monocyclic or bicyclic, or tricyclic alkyl groups including cyclopropyl, cyclobutyl, cyclopentyl, cyclohexyl, bicyclo[2.2.1]heptyl and adamantanyl; the term "aryl" represents phenyl or naphthyl, or phenyl substituted by one or more substituents selected independently from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, and pyridyl; the term "biaryl" represents biphenylene, preferably 4,4'-biphenylene, wherein one or both phenyl rings may optionally be substituted independently by one or more of the substituents independently selected from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, and pyridyl; the term "heteroaryl" represents an aromatic 5-6 membered ring comprising one to four heteroatoms selected from oxygen, sulfur and nitrogen, and a 5-6 membered bicyclic ring comprising one to four heteroatoms selected from oxygen, sulfur and nitrogen fused with a benzene ring or a 5-6 membered ring comprising one to four heteroatoms selected from oxygen, sulfur and nitrogen, wherein the heteroaryl is optionally substituted by one or more substituents selected independently from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, pyridyl, and aryl; heteroaryl may be furyl, thiophenyl, pyrrolyl, oxazolyl, isoxazolyl, thiazolyl, imidazolyl, oxadiazolyl, tetrazolyl, pyridinyl, pyrimidyl, benzofuryl, benzothiophenyl, indolyl, benzimidazolyl, benzoxazolyl, benzothiazolyl, quinolyl and isoquinolyl; and the term "halogen" represents fluorine, chlorine, bromine and iodine;

and optical isomers, polymorphs and pharmaceutically-acceptable acid and base addition salts, hydrates, and solvates thereof;

it being understood that:

$R^2$ may not represent unsubstituted phenyl or naphthyl;

$R^2$ may not represent substituted phenyl having at least one ortho-substituent other than hydrogen, relative to the tetrahydroquinoline ring of formula IA to which the phenyl is attached;

$R^2$ may not represent dimethylamino;

if one of $R^5$ and $R^6$ and one of $R^7$ and $R^8$ together represent —(CH$_2$)$_n$— with n being 3, 4 or 5, while the remaining of $R^5$ and $R^6$ as well as $R^7$ and $R^8$ are both hydrogen, then $R^2$ may also be halogen;

if $R^3$, $R^4$, $R^5$, $R^6$, $R^7$, $R^8$, $R^9$ and $R^{10}$ all represent hydrogen at the same time, then $R^2$ may not represent $C_{2-6}$alkyl;

if R³ is cyano, then R² may not represent methylthio or ethylthio;

R⁷ and R⁸ may not represent furyl;

and the compound of Formula IA may not represent:

2-Benzyloxy-7,8-dihydro-6H-quinoline-5-one, 2-Phenoxy-7,8-dihydro-6H-quinolin-5-one, 2-(1H-Indol-3-yl)-7,8-dihydro-6H-quinolin-5-one, 2-(1H-Indol-3-yl)-7,7-dimethyl-7,8-dihydro-6H-quinolin-5-one, 2-Thiophen-2-yl-7,8-dihydro-6H-quinolin-5-one, 2-Ethoxy-7,8-dihydro-6H-quinolin-5-one, 7,7-Dimethyl-2-(6-methyl-pyridin-3-ylmethylsulfanyl)-5-oxo-5,6,7,8-tetrahydro-quinoline-3-carbonitrile, 2-(1H-Benzoimidazol-2-ylmethylsulfanyl)-7,7-dimethyl-5-oxo-5,6,7,8-tetrahydro-quinoline-3-carbonitrile, 2-(4-Methoxy-phenyl)-7,8-dihydro-6H-quinolin-5-one, 2-(4-Chloro-phenyl)-7,7-dimethyl-7,8-dihydro-6H-quinolin-5-one, 2-(4-Fluoro-phenyl)-7,8-dihydro-6H-quinolin-5-one, 2-(4-Isopropyl-phenyl)-5-oxo-5,6,7,8-tetrahydro-quinoline-3-carbonitrile, or 2-Cyclohexyl-7,8-dihydro-6H-quinolin-5-one.

Specific compounds of Formula IA within the present invention include but are not limited to:

7,7-Dimethyl-2-(2-methyl-allylsulfanyl)-5-oxo-5,6,7,8-tetrahydroquinoline-3-carbonitrile, 2-Isopropylsulfanyl-7,7-dimethyl-5-oxo-5,6,7,8-tetrahydroquinoline-3-carbonitrile, 7,7-Dimethyl-5-oxo-2-propylsulfanyl-5,6,7,8-tetrahydroquinoline-3-carbonitrile, 2-(2-Methyl-allylsulfanyl)-5-oxo-5,6,7,8-tetrahydroquinoline-3-carbonitrile, 2-Butylsulfanyl-7,7-dimethyl-5-oxo-5,6,7,8-tetrahydroquinoline-3-carbonitrile, 7,7-Dimethyl-5-oxo-2-piperidin-1-yl-5,6,7,8-tetrahydroquinoline-3-carbonitrile, 2-Benzylamino-7,7-dimethyl-5-oxo-5,6,7,8-tetrahydroquinoline-3-carbonitrile, 7,7-Dimethyl-2-phenethyl-7,8-dihydro-6H-quinolin-5-one, 2-Cyclohexyloxy-7,7-dimethyl-7,8-dihydro-6H-quinolin-5-one, 2-Isobutoxy-7,7-dimethyl-5,6,7,8-tetrahydroquinolin-5-one, 2-Isobutylsulfanyl-7,7-dimethyl-5-oxo-5,6,7,8-tetrahydroquinoline-3-carbonitrile, 2-Benzylamino-7,7-dimethyl-7,8-dihydro-6H-quinolin-5-one, 2-Benzyloxy-7,7-dimethyl-7,8-dihydro-6H-quinolin-5-one, 2-Benzyl-7,7-dimethyl-7,8-dihydro-6H-quinolin-5-one, 2-[2-(2-Methoxyphenyl)ethyl]-7,8-dihydro-6H-quinolin-5-one, 2-Adamantan-1-yl-6-propyl-7,8-dihydro-6H-quinolin-5-one, 7-Phenyl-2-pyridin-2-yl-7,8-dihydro-6H-quinolin-5-one, 2-Benzyloxy-7-(4-chloro-phenyl)-7,8-dihydro-6H-quinolin-5-one, 2-Adamantan-1-yl-7,7-dimethyl-7,8-dihydro-6H-quinolin-5-one, 2-Adamantan-1-yl-7,8-dihydro-6H-quinolin-5-one, 2-Isobutoxy-7-phenyl-7,8-dihydro-6H-quinolin-5-one, 2-Phenoxy-7-phenyl-7,8-dihydro-6H-quinolin-5-one, 2-Phenethyl-7,8-dihydro-6H-quinolin-5-one, 2-Benzyloxy-7,7-pentamethylene-7,8-dihydro-6H-quinoline-5-one, 2-Adamantan-1-yl-7,7-pentamethylene-7,8-dihydro-6H-quinoline-5-one, 2-Ethoxy-7,7-pentamethylene-7,8-dihydro-6H-quinoline-5-one, 2-(2-Hydroxyethoxy)-1-yl-7,7-pentamethylene-7,8-dihydro-6H-quinoline-5-one, 2-Isopropyl-7,7-dimethyl-7,8-dihydro-6H-quinolin-5-one, 2-Benzyloxy-7-ethyl-7,8-dihydro-6H-quinolin-5-one, 7-(4-Dimethylamino-phenyl)-2-hexyl-7,8-dihydro-6H-quinolin-5-one, 2-Cyclohexyl-7-propyl-7,8-dihydro-6H-quinolin-5-one, 2-(4-Methoxy-phenyl)-6,6-dimethyl-7,8-dihydro-6H-quinolin-5-one, cis,trans-6-Ethyl-2-(4-methoxy-phenyl)-cis,trans-6,8-dimethyl-7,8-dihydro-6H-quinolin-5-one, 2-(3-Methoxy-phenyl)-7,7-dimethyl-7,8-dihydro-6H-quinolin-5-one, 2-(3-Methoxy-phenyl)-6-ethyl-7,8-dihydro-6H-quinolin-5-one, 2-(3-Methoxy-phenyl)-6-methyl-7,8-dihydro-6H-quinolin-5-one, 2-Adamantan-1-yl-6-ethyl-8-methyl-7,8-dihydro-6H-quinolin-5-one, 2-Ethoxy-7-furan-2-yl-7,8-dihydro-6H-quinolin-5-one, 2-Adamantan-1-yl-6,6-dimethyl-7,8-dihydro-6H-quinolin-5-one, (cis,trans) 2-Adamantan-1-yl-6-ethyl-8-methyl-7,8-dihydro-6H-quinolin-5-one and 2-adamantan-1-yl-8-ethyl-6-methyl-7,8-dihydro-6H-quinolin-5-one, cis,trans 6-Ethyl-2-hexyl-6,8-dimethyl-7,8-dihydro-6H-quinolin-5-one, 2-Cyclohexylmethyl-7,7-tetramethylene-7,8-dihydro-6H-quinolin-5-one 2-Hexyl-7-phenyl-7,8-dihydro-6H-quinolin-5-one, 2-Cyclohexyl-7-isopropyl-7,8-dihydro-6H-quinolin-5-one, 2-Cyclohexyl-6-ethyl-6-methyl-7,8-dihydro-6H-quinolin-5-one, 2-(3-Methoxy-phenyl)-6,6,8-trimethyl-7,8-dihydro-6H-quinolin-5-one, cis,trans 6-Ethyl-2-(3-methoxy-phenyl)-8-methyl-7,8-dihydro-6H-quinolin-5-one and 8-ethyl-2-(3-methoxy-phenyl)-6-methyl-7,8-dihydro-6H-quinolin-5-one, cis 2-(3-Methoxy-phenyl)-6,8-dimethyl-7,8-dihydro-6H-quinolin-5-one, 2-(3-Methoxy-phenyl)-6,6-dimethyl-7,8-dihydro-6H-quinolin-5-one, 2-Hexyl-cis,trans-6,8-dimethyl-7,8-dihydro-6H-quinolin-5-one, 2-Hexyl-7-propyl-7,8-dihydro-6H-quinolin-5-one, 6-Ethyl-2-hexyl-7,8-dihydro-6H-quinolin-5-one, 2-Hexyl-6,6,8-trimethyl-7,8-dihydro-6H-quinolin-5-one, 2-Hexyl-6,6-dimethyl-7,8-dihydro-6H-quinolin-5-one, cis,trans-8-Ethyl-2-hexyl-6-methyl-7,8-dihydro-6H-quinolin-5-one and cis,trans-6-ethyl-2-hexyl-8-methyl-7,8-dihydro-6H-quinolin-5-one, 2-Hexyl-7-isopropyl-7,8-dihydro-6H-quinolin-5-one, 2-(3-Methoxy-phenyl)-7,7-tetramethylene-7,8-dihydro-6H-quinolin-5-one, 2-(4-Methoxy-phenyl)-6-propyl-7,8-dihydro-6H-quinolin-5-one, 2-(3-Methoxy-phenyl)-6-propyl-7,8-dihydro-6H-quinolin-5-one, 2-(4-Methoxy-phenyl)-6,6,8-trimethyl-7,8-dihydro-6H-quinolin-5-one, 2-(4-Methoxy-phenyl)-7,7-tetramethylene-7,8-dihydro-6H-quinolin-5-one, 2-Hexyl-7-(3-methoxy-phenyl)-7,8-dihydro-6H-quinolin-5-one,
2-Hexyl-6,6-dimethyl-7,8-dihydro-6H-quinolin-5-one,
2-Benzyl-7,7-tetramethylene-7,8-dihydro-6H-quinolin-5-one,
2-Benzyl-6-propyl-7,8-dihydro-6H-quinolin-5-one,
2-Benzyl-6-ethyl-7,8-dihydro-6H-quinolin-5-one,
2-Benzyl-7-propyl-7,8-dihydro-6H-quinolin-5-one,
7-Ethyl-2-(4-methoxy-phenyl)-7,8-dihydro-6H-quinolin-5-one,
2-(4-Methoxy-phenyl)-6,8-dimethyl-7,8-dihydro-6H-quinolin-5-one,
2-(4-Methoxy-phenyl)-8-methyl-6-propyl-7,8-dihydro-6H-quinolin-5-one,
2-Benzyl-6,6-dimethyl-7,8-dihydro-6H-quinolin-5-one,
2-Benzyl-6,6,8-trimethyl-7,8-dihydro-6H-quinolin-5-one,
2-Benzyl-7-ethyl-7,8-dihydro-6H-quinolin-5-one,
(cis,trans) 2-Benzyl-6-ethyl-8-methyl-7,8-dihydro-6H-quinolin-5-one and 2-benzyl-8-ethyl-6-methyl-7,8-dihydro-6H-quinolin-5-one,
2-Cyclohexylmethyl-7,7-dimethyl-7,8-dihydro-6H-quinolin-5-one,
2-Cyclohexylmethyl-7-ethyl-7,8-dihydro-6H-quinolin-5-one,
2-Cyclohexylmethyl-6,6-dimethyl-7,8-dihydro-6H-quinolin-5-one,
2-Cyclohexylmethyl-6-ethyl-7,8-dihydro-6H-quinolin-5-one,
7-Isopropyl-2-pyridin-3-yl-7,8-dihydro-6H-quinolin-5-one,
5-Oxo-2-phenylethynyl-5,6,7,8-tetrahydro-quinoline-3-carbonitrile,
2-Biphenyl-4-yl-7,8-dihydro-6H-quinolin-5-one,
2-Hexylamino-7,7-dimethyl-5-oxo-5,6,7,8-tetrahydro-quinoline-3-carbonitrile,
2-(4-Methoxy-phenylamino)-7,7-dimethyl-7,8-dihydro-6H-quinolin-5-one,
7,7-Dimethyl-5-oxo-2-[(tetrahydro-furan-2-ylmethyl)-amino]-5,6,7,8-tetrahydro-quinoline-3-carbonitrile,
2-Cyclopentylamino-7,7-dimethyl-5-oxo-5,6,7,8-tetrahydro-quinoline-3-carbonitrile,
2-(2-Methoxy-ethylamino)-5-oxo-5,6,7,8-tetrahydro-quinoline-3-carbonitrile,
2-(Benzyl-methyl-amino)-5-oxo-5,6,7,8-tetrahydro-quinoline-3-carbonitrile,
5-Oxo-2-[(tetrahydro-furan-2-ylmethyl)-amino]-5,6,7,8-tetrahydro-quinoline-3-carbonitrile,
2-Cyclohexylamino-5-oxo-5,6,7,8-tetrahydro-quinoline-3-carbonitrile,
5-Oxo-2-[(pyridin-2-ylmethyl)-amino]-5,6,7,8-tetrahydro-quinoline-3-carbonitrile,
2-Azepan-1-yl-5-oxo-5,6,7,8-tetrahydro-quinoline-3-carbonitrile,
2-(Cyclohexyl-methyl-amino)-7,8-dihydro-6H-quinolin-5-one,
2-Phenylamino-7,8-dihydro-6H-quinolin-5-one,
2-(Cyclohexyl-methyl-amino)-7,7-dimethyl-7,8-dihydro-6H-quinolin-5-one,
2-(Benzyl-methyl-amino)-7,7-dimethyl-5-oxo-5,6,7,8-tetrahydro-quinoline-3-carbonitrile,
7,7-Dimethyl-5-oxo-2-[(pyridin-3-ylmethyl)-amino]-5,6,7,8-tetrahydro-quinoline-3-carbonitrile,
7,7-Dimethyl-5-oxo-2-(4-phenyl-piperazin-1-yl)-5,6,7,8-tetrahydro-quinoline-3-carbonitrile,
2-Azepan-1-yl-7,7-dimethyl-7,8-dihydro-6H-quinolin-5-one,
2-(4-Phenyl-piperazin-1-yl)-7,8-dihydro-6H-quinolin-5-one,
2-Phenylethynyl-7,8-dihydro-6H-quinolin-5-one,
7,7-Dimethyl-2-(1-phenyl-ethylamino)-7,8-dihydro-6H-quinolin-5-one,
2-(3,5-Dimethoxy-benzylamino)-7,8-dihydro-6H-quinolin-5-one,
2-(3,5-Difluoro-benzylamino)-7,8-dihydro-6H-quinolin-5-one,
2-Biphenyl-4-yl-5-oxo-5,6,7,8-tetrahydro-quinoline-3-carbonitrile,
5-Oxo-2-(5-phenyl-thiophen-2-yl)-5,6,7,8-tetrahydro-quinoline-3-carbonitrile,
5-Oxo-2-(1-phenyl-ethylamino)-5,6,7,8-tetrahydro-quinoline-3-carbonitrile,
2-(3-Fluoro-benzylamino)-7,8-dihydro-6H-quinolin-5-one,
3-[(5-Oxo-5,6,7,8-tetrahydro-quinolin-2-ylamino)-methyl]-benzonitrile,
2-Phenylamino-6,7,8,9,9a,10-hexahydro-5aH-benzo[g]quinolin-5-one,
2-(1-Phenyl-ethylamino)-6,7,8,9,9a,10-hexahydro-5aH-benzo[g]quinolin-5-one,
2-(Cyclohexyl-methyl-amino)-6,7,8,9,9a,10-hexahydro-5aH-benzo[g]quinolin-5-one,
2-(4-Phenyl-piperazin-1-yl)-6,7,8,9,9a,10-hexahydro-5aH-benzo[g]quinolin-5-one,
6-Ethyl-2-(2-methoxy-phenyl)-6-methyl-7,8-dihydro-6H-quinolin-5-one hydrochloride,
2-Benzyl-7,8-dihydro-6H-quinolin-5-one,
7,7-Dimethyl-2-styryl-7,8-dihydro-6H-quinolin-5-one,
2-Pyridin-3-ylethynyl-7,8-dihydro-6H-quinolin-5-one,
2-m-Tolylethynyl-7,8-dihydro-6H-quinolin-5-one,
2-(3-Hydroxy-phenylethynyl)-7,8-dihydro-6H-quinolin-5-one,
2-(3-Methoxy-phenylethynyl)-7,8-dihydro-6H-quinolin-5-one,
2-(3-Fluoro-phenylethynyl)-7,8-dihydro-6H-quinolin-5-one,
2-(3-Chloro-phenylethynyl)-7,8-dihydro-6H-quinolin-5-one,
2-(3-Bromo-phenylethynyl)-7,8-dihydro-6H-quinolin-5-one,
3-(5-Oxo-5,6,7,8-tetrahydro-quinolin-2-ylethynyl)-benzonitrile,
2-Thiazol-5-ylethynyl-7,8-dihydro-6H-quinolin-5-one,
2-Oxazol-5-ylethynyl-7,8-dihydro-6H-quinolin-5-one,
2-(3-Methoxy-4-pyridin-3-yl-phenyl)-7,8-dihydro-6H-quinolin-5-one,
2-(3-Methoxy-4-pyridin-2-yl-phenyl)-7,8-dihydro-6H-quinolin-5-one,
2-Phenylethynyl-6,7,8,9,9a,10-hexahydro-5aH-benzo[g]quinolin-5-one,
2-Bromo-6,7,8,9,9a,10-hexahydro-5aH-benzo[g]quinolin-5-one,
2-Chloro-3-fluoro-6,7,8,9,9a,10-hexahydro-5aH-benzo[g]quinolin-5-one,
3-(5-Oxo-5,5a,6,7,8,9,9a,10-octahydro-benzo[g]quinolin-2-yl)-benzonitrile,
2-Pyridin-3-yl-6,7,8,9,9a,10-hexahydro-5aH-benzo[g]quinolin-5-one,
2-Piperidin-1-yl-6,7,8,9,9a,10-hexahydro-5aH-benzo[g]quinolin-5-one,
4-Chloro-5-oxo-2-(4-phenyl-piperazin-1-yl)-5,6,7,8-tetrahydro-quinoline-3-carbonitrile,
4-Bromo-5-oxo-2-(4-phenyl-piperazin-1-yl)-5,6,7,8-tetrahydro-quinoline-3-carbonitrile, 4-Methoxy-5-oxo-2-(4-phenyl-piperazin-1-yl)-5,6,7,8-tetrahydro-quinoline-3-carbonitrile,
4-Ethoxy-5-oxo-2-(4-phenyl-piperazin-1-yl)-5,6,7,8-tetrahydro-quinoline-3-carbonitrile,
4-Hydroxymethoxy-5-oxo-2-(4-phenyl-piperazin-1-yl)-5,6,7,8-tetrahydro-quinoline-3-carbonitrile,
4-Hydroxymethoxy-7,7-dimethyl-5-oxo-2-(4-phenyl-piperazin-1-yl)-5,6,7,8-tetrahydro-quinoline-3-carbonitrile,
4-Ethoxy-7,7-dimethyl-5-oxo-2-(4-phenyl-piperazin-1-yl)-5,6,7,8-tetrahydro-quinoline-3-carbonitrile,
4-Methoxy-7,7-dimethyl-5-oxo-2-(4-phenyl-piperazin-1-yl)-5,6,7,8-tetrahydro-quinoline-3-carbonitrile,
4-Chloro-7,7-dimethyl-5-oxo-2-(4-phenyl-piperazin-1-yl)-5,6,7,8-tetrahydro-quinoline-3-carbonitrile,
4-Bromo-7,7-dimethyl-5-oxo-2-(4-phenyl-piperazin-1-yl)-5,6,7,8-tetrahydro-quinoline-3-carbonitrile,
4-Bromo-7,7-dimethyl-5-oxo-2-(4-phenyl-piperidin-1-yl)-5,6,7,8-tetrahydro-quinoline-3-carbonitrile,
4-Chloro-7,7-dimethyl-5-oxo-2-(4-phenyl-piperidin-1-yl)-5,6,7,8-tetrahydro-quinoline-3-carbonitrile,
4-Methoxy-7,7-dimethyl-5-oxo-2-(4-phenyl-piperidin-1-yl)-5,6,7,8-tetrahydro-quinoline-3-carbonitrile,
4-Ethoxy-7,7-dimethyl-5-oxo-2-(4-phenyl-piperidin-1-yl)-5,6,7,8-tetrahydro-quinoline-3-carbonitrile,
4-(2-Hydroxy-ethoxy)-7,7-dimethyl-5-oxo-2-(4-phenyl-piperidin-1-yl)-5,6,7,8-tetrahydro-quinoline-3-carbonitrile,
3-Chloro-7,7-dimethyl-2-(4-phenyl-piperidin-1-yl)-7,8-dihydro-6H-quinolin-5-one,
3-Bromo-7,7-dimethyl-2-(4-phenyl-piperidin-1-yl)-7,8-dihydro-6H-quinolin-5-one,
3-Fluoro-7,7-dimethyl-2-(4-phenyl-piperidin-1-yl)-7,8-dihydro-6H-quinolin-5-one,
3-Methoxy-7,7-dimethyl-2-(4-phenyl-piperidin-1-yl)-7,8-dihydro-6H-quinolin-5-one,
7,7-Dimethyl-3-nitro-2-(4-phenyl-piperidin-1-yl)-7,8-dihydro-6H-quinolin-5-one,
7,7-Dimethyl-3-nitro-2-(4-phenyl-piperazin-1-yl)-7,8-dihydro-6H-quinolin-5-one,
3-Fluoro-7,7-dimethyl-2-(4-phenyl-piperazin-1-yl)-7,8-dihydro-6H-quinolin-5-one,
3-Bromo-7,7-dimethyl-2-(4-phenyl-piperazin-1-yl)-7,8-dihydro-6H-quinolin-5-one,
3-Chloro-7,7-dimethyl-2-(4-phenyl-piperazin-1-yl)-7,8-dihydro-6H-quinolin-5-one,
3-Methoxy-7,7-dimethyl-2-(4-phenyl-piperazin-1-yl)-7,8-dihydro-6H-quinolin-5-one,
2-[4-(4-Methoxy-phenyl)-piperazin-1-yl]-7,7-dimethyl-5-oxo-5,6,7,8-tetrahydro-quinoline-3-carbonitrile,
2-[4-(4-Fluoro-phenyl)-piperazin-1-yl]-7,7-dimethyl-5-oxo-5,6,7,8-tetrahydro-quinoline-3-carbonitrile,
2-(5-m-Tolyl-thiazol-2-yl)-7,8-dihydro-6H-quinolin-5-one,
2-[5-(3-Hydroxy-phenyl)-thiazol-2-yl]-7,8-dihydro-6H-quinolin-5-one,
2-[5-(3-Methoxy-phenyl)-thiazol-2-yl]-7,8-dihydro-6H-quinolin-5-one,
2-[5-(3-Fluoro-phenyl)-thiazol-2-yl]-7,8-dihydro-6H-quinolin-5-one,
2-[5-(3-Chloro-phenyl)-thiazol-2-yl]-7,8-dihydro-6H-quinolin-5-one,
2-[5-(3-Bromo-phenyl)-thiazol-2-yl]-7,8-dihydro-6H-quinolin-5-one,
3-[2-(5-Oxo-5,6,7,8-tetrahydro-quinolin-2-yl)-thiazol-5-yl]-benzonitrile,
2-[5-(3,5-Dimethoxy-phenyl)-thiazol-2-yl]-7,8-dihydro-6H-quinolin-5-one,
2-[2-(3,5-Dimethoxy-phenyl)-vinyl]-7,8-dihydro-6H-quinolin-5-one,
2-[5-(3-Fluoro-5-methyl-phenyl)-thiazol-2-yl]-7,8-dihydro-6H-quinolin-5-one,
3-Fluoro-5-[2-(5-oxo-5,6,7,8-tetrahydro-quinolin-2-yl)-thiazol-5-yl]-benzonitrile,
2-[5-(3-Fluoro-5-methoxy-phenyl)-thiazol-2-yl]-7,8-dihydro-6H-quinolin-5-one,
2-[5-(3-Fluoro-5-pyridin-2-yl-phenyl)-thiazol-2-yl]-7,8-dihydro-6H-quinolin-5-one,
2-[5-(3-Fluoro-5-pyridin-3-yl-phenyl)-thiazol-2-yl]-7,8-dihydro-6H-quinolin-5-one,
2-Adamantan-1-yl-6,7,8,9,9a,10-hexahydro-5aH-benzo[g]quinolin-5-one,
7,7-Dimethyl-2-pyridin-3-ylethynyl-7,8-dihydro-6H-quinolin-5-one,
7,7-Dimethyl-2-m-tolylethynyl-7,8-dihydro-6H-quinolin-5-one,
2-(3-Hydroxy-phenylethynyl)-7,7-dimethyl-7,8-dihydro-6H-quinolin-5-one,
2-(3-Methoxy-phenylethynyl)-7,7-dimethyl-7,8-dihydro-6H-quinolin-5-one,
2-(3-Fluoro-phenylethynyl)-7,7-dimethyl-7,8-dihydro-6H-quinolin-5-one,
2-(3-Chloro-phenylethynyl)-7,7-dimethyl-7,8-dihydro-6H-quinolin-5-one,
2-(3-Bromo-phenylethynyl)-7,7-dimethyl-7,8-dihydro-6H-quinolin-5-one,
3-(7,7-Dimethyl-5-oxo-5,6,7,8-tetrahydro-quinolin-2-ylethynyl)-benzonitrile,
7,7-Dimethyl-2-thiazol-5-ylethynyl-7,8-dihydro-6H-quinolin-5-one,
7,7-Dimethyl-2-oxazol-5-ylethynyl-7,8-dihydro-6H-quinolin-5-one,
2-(3-Methoxy-4-pyridin-3-yl-phenyl)-7,7-dimethyl-7,8-dihydro-6H-quinolin-5-one,
2-(3-Methoxy-4-pyridin-2-yl-phenyl)-7,7-dimethyl-7,8-dihydro-6H-quinolin-5-one,
2-[5-(3-Fluoro-5-pyridin-4-yl-phenyl)-thiazol-2-yl]-7,8-dihydro-6H-quinolin-5-one,
2-[5-(3-Fluoro-5-morpholin-4-yl-phenyl)-thiazol-2-yl]-7,8-dihydro-6H-quinolin-5-one,
2-[5-(3-Fluoro-5-piperidin-1-yl-phenyl)-thiazol-2-yl]-7,8-dihydro-6H-quinolin-5-one
7,7-Dimethyl-2-(5-m-tolyl-thiazol-2-yl)-7,8-dihydro-6H-quinolin-5-one,
2-[5-(3-Hydroxy-phenyl)-thiazol-2-yl]-7,7-dimethyl-7,8-dihydro-6H-quinolin-5-one,
2-[5-(3-Methoxy-phenyl)-thiazol-2-yl]-7,7-dimethyl-7,8-dihydro-6H-quinolin-5-one,
2-[5-(3-Fluoro-phenyl)-thiazol-2-yl]-7,7-dimethyl-7,8-dihydro-6H-quinolin-5-one,
2-[5-(3-Chloro-phenyl)-thiazol-2-yl]-7,7-dimethyl-7,8-dihydro-6H-quinolin-5-one,
2-[5-(3-Bromo-phenyl)-thiazol-2-yl]-7,7-dimethyl-7,8-dihydro-6H-quinolin-5-one,
3-[2-(7,7-Dimethyl-5-oxo-5,6,7,8-tetrahydro-quinolin-2-yl)-thiazol-5-yl]-benzonitrile,
2-[5-(3,5-Dimethoxy-phenyl)-thiazol-2-yl]-7,7-dimethyl-7,8-dihydro-6H-quinolin-5-one,
2-[2-(3,5-Dimethoxy-phenyl)-vinyl]-7,7-dimethyl-7,8-dihydro-6H-quinolin-5-one,
2-[5-(3-Fluoro-5-methyl-phenyl)-thiazol-2-yl]-7,7-dimethyl-7,8-dihydro-6H-quinolin-5-one, 3-[2-(7,7-Dimethyl-5-oxo-5,6,7,8-tetrahydro-quinolin-2-yl)-thiazol-5-yl]-5-fluoro-benzonitrile,
2-[5-(3-Fluoro-phenyl)-thiazol-2-yl]-7,8-dihydro-6H-quinolin-5-one,
2-[5-(3-Fluoro-5-methoxy-phenyl)-thiazol-2-yl]-7,7-dimethyl-7,8-dihydro-6H-quinolin-5-one,
2-[5-(3-Fluoro-5-pyridin-2-yl-phenyl)-thiazol-2-yl]-7,7-dimethyl-7,8-dihydro-6H-quinolin-5-one,
2-[5-(3-Fluoro-5-pyridin-3-yl-phenyl)-thiazol-2-yl]-7,7-dimethyl-7,8-dihydro-6H-quinolin-5-one,
2-[5-(3-Fluoro-5-pyridin-4-yl-phenyl)-thiazol-2-yl]-7,7-dimethyl-7,8-dihydro-6H-quinolin-5-one,
2-[5-(3-Fluoro-5-morpholin-4-yl-phenyl)-thiazol-2-yl]-7,7-dimethyl-7,8-dihydro-6H-quinolin-5-one,
2-[5-(3-Fluoro-5-piperidin-1-yl-phenyl)-thiazol-2-yl]-7,7-dimethyl-7,8-dihydro-6H-quinolin-5-one,
2-(5-m-Tolyl-[1,3,4]oxadiazol-2-yl)-7,8-dihydro-6H-quinolin-5-one,
2-(5-m-Tolyl-oxazol-2-yl)-7,8-dihydro-6H-quinolin-5-one,
2-(1-m-Tolyl-1H-imidazol-4-yl)-7,8-dihydro-6H-quinolin-5-one,
2-(5-m-Tolyl-isoxazol-3-yl)-7,8-dihydro-6H-quinolin-5-one,
2-[5-(3-Fluoro-phenyl)-oxazol-2-yl]-7,8-dihydro-6H-quinolin-5-one,
2-[1-(3-Fluoro-phenyl)-1H-imidazol-4-yl]-7,8-dihydro-6H-quinolin-5-one,
2-[5-(3-Fluoro-phenyl)-isoxazo-3-yl]-7,8-dihydro-6H-quinolin-5-one,
3-[2-(5-Oxo-5,6,7,8-tetrahydro-quinolin-2-yl)-oxazol-5-yl]-benzonitrile,
3-[1-(5-Oxo-5,6,7,8-tetrahydro-quinolin-2-yl)-1H-imidazol-4-yl]-benzonitrile,
3-[3-(5-Oxo-5,6,7,8-tetrahydro-quinolin-2-yl)-isoxazol-5-yl]-benzonitrile,
3-[2-(7,7-Dimethyl-5-oxo-5,6,7,8-tetrahydro-quinolin-2-yl)-oxazol-5-yl]-benzonitrile,
3-[1-(7,7-Dimethyl-5-oxo-5,6,7,8-tetrahydro-quinolin-2-yl)-1H-imidazol-4-yl]-benzonitrile,
3-[3-(7,7-Dimethyl-5-oxo-5,6,7,8-tetrahydro-quinolin-2-yl)-isoxazol-5-yl]-benzonitrile,
3-[2-(7,7-Dimethyl-5-oxo-5,6,7,8-tetrahydro-quinolin-2-yl)-oxazol-5-yl]-5-fluoro-benzonitrile,
3-[1-(7,7-Dimethyl-5-oxo-5,6,7,8-tetrahydro-quinolin-2-yl)-1H-imidazol-4-yl]-5-fluoro-benzonitrile,
3-[3-(7,7-Dimethyl-5-oxo-5,6,7,8-tetrahydro-quinolin-2-yl)-isoxazol-5-yl]-5-fluoro-benzonitrile,
7,7-Dimethyl-2-(5-pyridin-3-yl-thiazol-2-yl)-7,8-dihydro-6H-quinolin-5-one,
2-(5-Pyridin-3-yl-thiazol-2-yl)-7,8-dihydro-6H-quinolin-5-one,
2-(3-Methoxy-4-pyridin-2-yl-phenylamino)-7,7-dimethyl-7,8-dihydro-6H-quinolin-5-one,
2-(3-Methoxy-4-pyridin-3-yl-phenylamino)-7,7-dimethyl-7,8-dihydro-6H-quinolin-5-one,
2-(3-Fluoro-4-pyridin-2-yl-phenylamino)-7,7-dimethyl-7,8-dihydro-6H-quinolin-5-one,
7,7-Dimethyl-2-(pyridin-2-ylamino)-7,8-dihydro-6H-quinolin-5-one,
2-(3-Methoxy-phenylamino)-7,7-dimethyl-7,8-dihydro-6H-quinolin-5-one,
2-(Indan-2-ylamino)-7,7-dimethyl-5-oxo-5,6,7,8-tetrahydro-quinoline-3-carbonitrile,
7,7-Dimethyl-5-oxo-2-phenylamino-5,6,7,8-tetrahydro-quinoline-3-carbonitrile,
2-(4-Methoxy-phenylamino)-7,7-dimethyl-5-oxo-5,6,7,8-tetrahydro-quinoline-3-carbonitrile,
2-(4-Methoxy-phenylamino)-7,7-dimethyl-3-nitro-7,8-dihydro-6H-quinolin-5-one,
2-(1,3-Dihydro-isoindol-2-yl)-7,7-dimethyl-5-oxo-5,6,7,8-tetrahydro-quinoline-3-carbonitrile,
2-(3,4-Dihydro-1H-isoquinolin-2-yl)-7,7-dimethyl-5-oxo-5,6,7,8-tetrahydro-quinoline-3-carbonitrile,
2-(Adamantan-1-ylamino)-7,7-dimethyl-5-oxo-5,6,7,8-tetrahydro-quinoline-3-carbonitrile,
7,7-Dimethyl-3-morpholin-4-yl-2-(4-phenyl-piperidin-1-yl)-7,8-dihydro-6H-quinolin-5-one,
[4-(7,7-Dimethyl-5-oxo-5,6,7,8-tetrahydro-quinolin-2-ylamino)-2-methoxy-phenyl]-acetonitrile,
2-(3-Fluoro-4-pyridin-3-yl-phenylamino)-7,7-dimethyl-7,8-dihydro-6H-quinolin-5-one,
[4-(7,7-Dimethyl-5-oxo-5,6,7,8-tetrahydro-quinolin-2-ylamino)-2-fluoro-phenyl]-acetonitrile,
2-(3-Methoxy-4-pyridin-2-yl-phenylamino)-7,8-dihydro-6H-quinolin-5-one,
2-(3-Methoxy-4-pyridin-3-yl-phenylamino)-7,8-dihydro-6H-quinolin-5-one,
[2-Methoxy-4-(5-oxo-5,6,7,8-tetrahydro-quinolin-2-ylamino)-phenyl]-acetonitrile,
2-(3-Fluoro-4-pyridin-2-yl-phenylamino)-7,8-dihydro-6H-quinolin-5-one,
2-(3-Fluoro-4-pyridin-3-yl-phenylamino)-7,8-dihydro-6H-quinolin-5-one,
[2-Fluoro-4-(5-oxo-5,6,7,8-tetrahydro-quinolin-2-ylamino)-phenyl]-acetonitrile,
7,7-Dimethyl-2-(pyridin-3-ylamino)-7,8-dihydro-6H-quinolin-5-one,
7,7-Dimethyl-2-(pyridin-4-ylamino)-7,8-dihydro-6H-quinolin-5-one,
5-Oxo-2-(5-phenyl-thiazol-2-yl)-5,6,7,8-tetrahydro-quinoline-3-carbonitrile,
2-(3-Methoxy-4-pyridin-2-yl-phenylamino)-7,7-dimethyl-5-oxo-5,6,7,8-tetrahydro-quinoline-3-carbonitrile,
2-(3-Methoxy-4-pyridin-3-yl-phenylamino)-7,7-dimethyl-5-oxo-5,6,7,8-tetrahydro-quinoline-3-carbonitrile,
7,7-Dimethyl-5-oxo-2-(pyridin-4-ylamino)-5,6,7,8-tetrahydro-quinoline-3-carbonitrile,
7,7-Dimethyl-3-nitro-2-(pyridin-4-ylamino)-7,8-dihydro-6H-quinolin-5-one,
2-(3,5-Dimethoxy-phenylamino)-7,7-dimethyl-7,8-dihydro-6H-quinolin-5-one,
2-Benzylsulfanyl-7,7-dimethyl-3-nitro-7,8-dihydro-6H-quinolin-5-one,
2-Benzylsulfanyl-3-chloro-7,7-dimethyl-7,8-dihydro-6H-quinolin-5-one,
7,7-Dimethyl-3-nitro-2-piperidin-1-yl-7,8-dihydro-6H-quinolin-5-one,
3-Chloro-7,7-dimethyl-2-piperidin-1-yl-7,8-dihydro-6H-quinolin-5-one,
2-Cyclopentylamino-7,7-dimethyl-3-nitro-7,8-dihydro-6H-quinolin-5-one,
3-Chloro-2-cyclopentylamino-7,7-dimethyl-7,8-dihydro-6H-quinolin-5-one,
3-Chloro-2-[4-(4-methoxy-phenyl)-piperazin-1-yl]-7,7-dimethyl-7,8-dihydro-6H-quinolin-5-one,
2-[4-(4-Methoxy-phenyl)-piperazin-1-yl]-7,7-dimethyl-3-nitro-7,8-dihydro-6H-quinolin-5-one,
7,7-Dimethyl-5-oxo-2-(3,4,5,6-tetrahydro-2H-[4,4']bipyridinyl-1-yl)-5,6,7,8-tetrahydro-quinoline-3-carbonitrile, 2-[4-(4-Methoxy-phenyl)-piperidin-1-yl]-7,7-dimethyl-5-oxo-5,6,7,8-tetrahydro-quinoline-3-carbonitrile,
2-[1-(4-Methoxy-phenyl)-piperidin-4-yl]-7,7-dimethyl-5-oxo-5,6,7,8-tetrahydro-quinoline-3-carbonitrile,
7,7-Dimethyl-5-oxo-2-(6,7,8,9-tetrahydro-5H-benzocyclohepten-7-ylamino)-5,6,7,8-tetrahydro-quinoline-3-carbonitrile,
2-(4-Methoxy-cyclohexylamino)-7,7-dimethyl-3-nitro-7,8-dihydro-6H-quinolin-5-one,
2-(4-Methoxy-cyclohexylamino)-7,7-dimethyl-3-nitro-7,8-dihydro-6H-quinolin-5-one,
2-(4-Methoxy-cyclohexylamino)-7,7-dimethyl-7,8-dihydro-6H-quinolin-5-one,
2-(4-Methoxy-cyclohexylamino)-7,7-dimethyl-5-oxo-5,6,7,8-tetrahydro-quinoline-3-carbonitrile,
3-[3-(7,7-Dimethyl-5-oxo-5,6,7,8-tetrahydro-quinolin-2-yl)-isoxazol-5-yl]-benzonitrile,
2-Benzylsulfanyl-5-oxo-5,6,7,8-tetrahydro-quinoline-3-carbonitrile,
2-(2-Methoxyphenyl)-7,8-dihydro-6H-quinolin-5-one,
2-Benzyloxy-7,8-dihydro-6H-quinolin-5-one,
2-Phenyl-7-7-pentamethylene-7,8-dihydro-6H-quinoline-5-one,
2-(2-Methoxy-phenyl)-7,7-dimethyl-7,8-dihydro-6H-quinolin-5-one,
6-Ethyl-2-phenyl-7,8-dihydro-6H-quinolin-5-one,
cis,trans-6-Ethyl-2-(2-methoxy-phenyl)-8-methyl-7,8-dihydro-6H-quinolin-5-one and
cis,trans-8-Ethyl-2-(2-methoxy-phenyl)-6-methyl-7,8-dihydro-6H-quinolin-5-one,
6,6,8-Trimethyl-2-phenyl-7,8-dihydro-6H-quinolin-5-one,
2-(3-Methoxy-benzyl)-6,6,8-trimethyl-7,8-dihydro-6H-quinolin-5-one,
6-Ethyl-2-(2-methoxy-phenyl)-7,8-dihydro-6H-quinolin-5-one,
2-(2-Methoxy-phenyl)-6,6-dimethyl-7,8-dihydro-6H-quinolin-5-one,
6,6-Dimethyl-2-phenyl-7,8-dihydro-6H-quinolin-5-one hydrochloride, and
2-Benzylsulfanyl-7,7-dimethyl-5-oxo-5,6,7,8-tetrahydro-quinoline-3-carbonitrile

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms, inclusive, (i.e., methyl, ethyl, propyl, and isopropyl), straight and branched forms thereof.

As used herein and as far as it is not defined in a different manner elsewhere in this description or the accompanied claims, the term "$C_{1-6}$alkyl" represents straight or branched chain alkyl groups having 1, 2, 3, 4, 5 or 6 carbon atoms; the term "$C_{2-6}$alkenyl" represents straight or branched chain alkenyl groups having 2, 3, 4, 5 or 6 carbon atoms; the term "cyclo$C_{3-12}$alkyl" represents monocyclic or bicyclic, or tricyclic alkyl groups having 3, 4, 5, 6, 7, 8, 9, 10, 11 or 12 carbon atoms including cyclopropyl, cyclobutyl, cyclopentyl, cyclohexyl, bicyclo[2.2.1]heptyl and adamantanyl; the term "aryl" represents phenyl or naphthyl, or phenyl substituted by one or more substituents selected independently from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, and pyridyl; the term "biaryl" represents biphenylene, preferably 4,4'-biphenylene, wherein one or both phenyl rings may optionally be substituted independently by one or more of, the substituents independently selected from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, and pyridyl; the term "heteroaryl" represents an aromatic 5-6 membered ring comprising one to four heteroatoms selected from oxygen, sulfur and nitrogen, and a 5-6 membered bicyclic ring comprising one to four heteroatoms selected from oxygen, sulfur and nitrogen fused with a benzene ring or a 5-6 membered ring comprising one to four heteroatoms selected from oxygen, sulfur and nitrogen, wherein the heteroaryl is optionally substituted by one or more substituents selected independently from a halogen, trifluoromethyl, $C_{1-6}$alkyl, $C_{2-6}$alkenyl, $C_{1-6}$alkoxy, amino, hydroxy, nitro, cyano, $C_{1-6}$alkoxycarbonyl, $C_{1-6}$alkylamino, di-$C_{1-6}$alkylamino, cyanomethyl, piperidinyl, morpholinyl, pyridyl, and aryl; heteroaryl may be furyl, thiophenyl, pyrrolyl, oxazolyl, isoxazolyl, thiazolyl, imidazolyl, tetrazolyl, pyridinyl, pyrimidyl, benzofuryl, benzothiophenyl, indolyl, benzimidazolyl, benzoxazolyl, benzothiazolyl, quinolyl and isoquinolyl; and the term "halogen" represents fluorine, chlorine, bromine and iodine.

The compounds of the present invention are named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, and "rt" for room temperature).

The term "analog" or "derivative" is used herein in the conventional pharmaceutical sense, to refer to a molecule that structurally resembles a reference molecule (such as 1-aminocyclohexane), but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

In addition, using methods known to those skilled in the art, analogs and derivatives of the compounds of the invention can be created which have improved therapeutic efficacy in controlling dementia, i.e., higher potency and/or selectivity at a specific targeted receptor type, either greater or lower ability to penetrate mammalian blood-brain barriers (e.g., either higher or lower blood-brain barrier permeation rate), fewer side effects, etc.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Compounds of the present invention may be in the form of pharmaceutically acceptable salts. "Pharmaceutically acceptable salts" refers to those salts which possess the biological effectiveness and properties of the parent compound and which are not biologically or otherwise undesirable. The nature of the salt or isomer is not critical, provided that it is non-toxic and does not substantially interfere with the desired pharmacological activity.

It will be appreciated by those skilled in the art that compounds of the invention having a chiral center may exist in and be isolated in optically active and racemic forms. Some compounds may exhibit polymorphism. It is to be understood that the present invention ecompasses any racemic, optically-active, polymorphic, tautomeric, or stereoisomeric form, or mixture thereof, of a compound of the invention, which possesses the useful properties described herein.

The following Schemes 1-2 describe the preparation of compounds of Formula IA of the present invention. All of the starting materials are prepared by procedures described in these schemes, by procedures well known to one of ordinary skill in organic chemistry or can be obtained commercially.

All of the compounds of the present invention are prepared by procedures described in these charts or by procedures analogous thereto, which would be well known to one of ordinary skill in organic chemistry. All of the variables used in the schemes are as defined below or as in the claims.

Compounds of general Formula IA were obtained, as shown in Scheme 1, by reacting appropriately functionalized cyclohexane-1,3-dione derivatives 1 with N,N-dimethylformamide dimethyl acetal and, subsequently, 2-cyano-thioacetamide to form the corresponding 5-oxo-2-thioxo-1,2,5,6,7,8-hexahydro-quinoline-3-carbonitrile derivative 3. Alkylation of 3 with alkyl halides under basic conditions led to 2-alkylsulfanyl-5-oxo-5,6,7,8-tetrahydro-quinoline-3-carbonitriles of Formula IA. The introduction of an amino-substituent was achieved by reacting 2-methylsulfanyl-5-oxo-5,6,7,8-tetrahydro-quinoline-3-carbonitriles 4 with a primary of secondary amine derivative to give amino substituted derivatives of Formula IA.

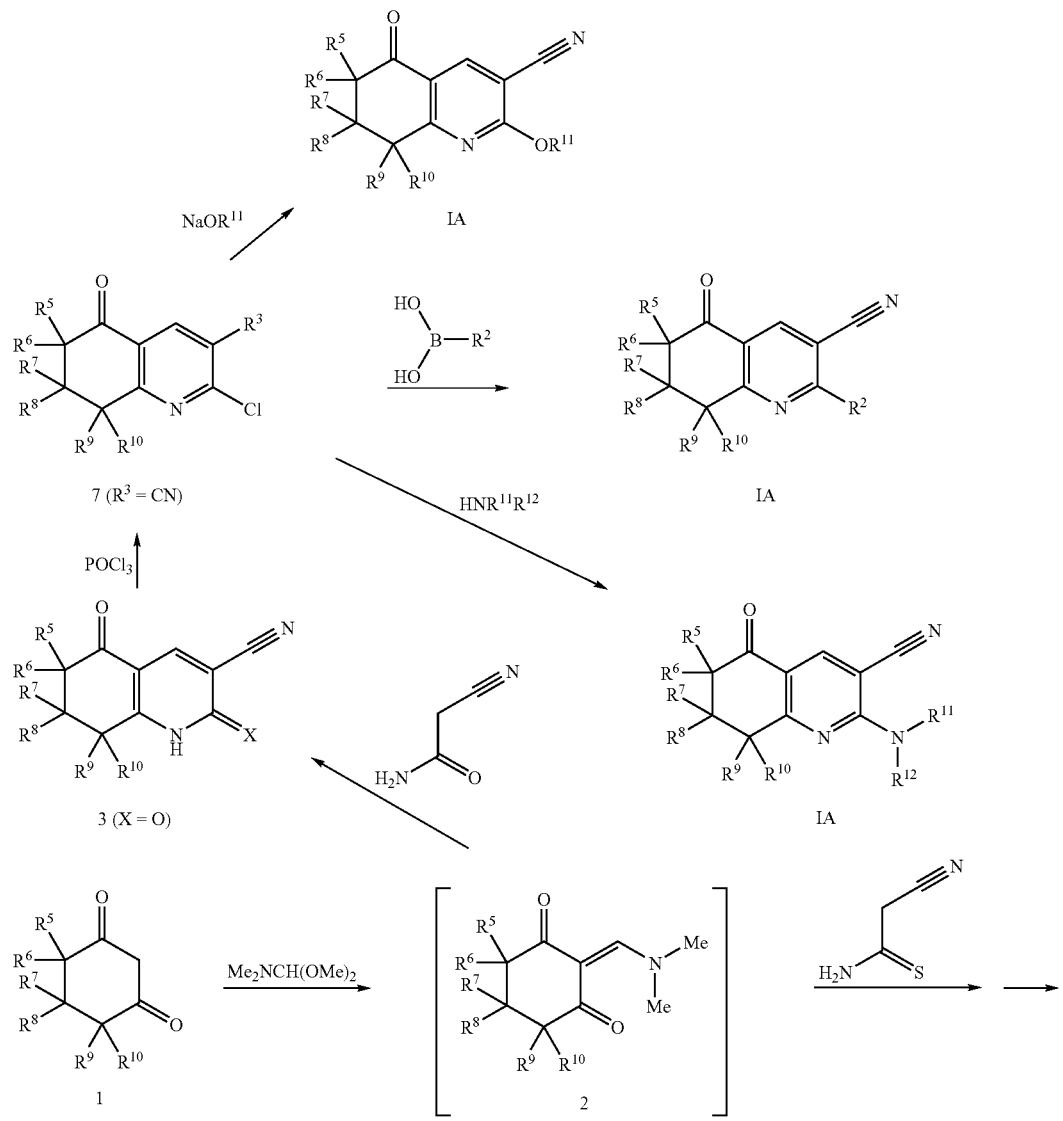

Scheme 1
Synthesis of 3-cyano-substituted 7,8-dihydro-6H-quinolin-5-ones

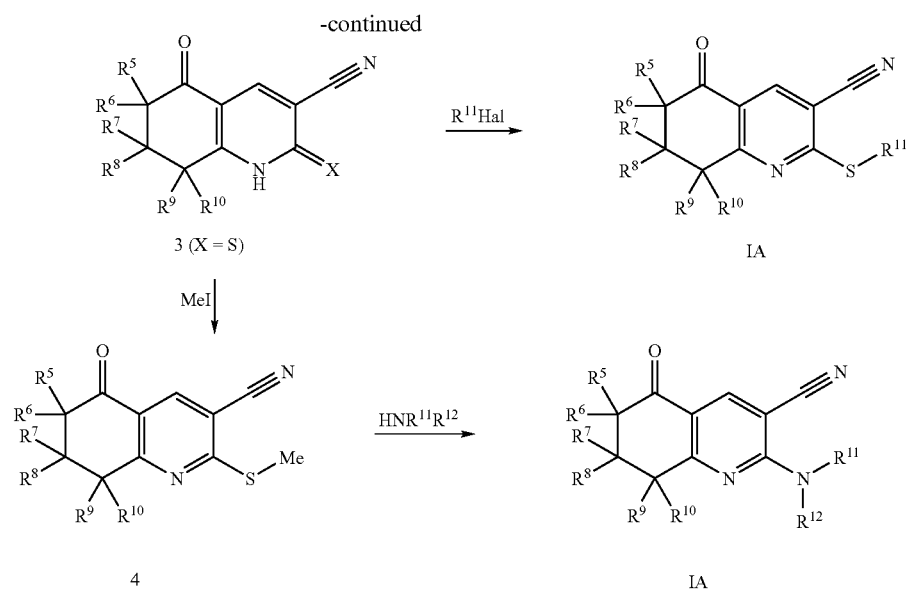

A synthetic procedure toward 3-unsubstituted 7,8-dihydro-6H-quinolin-5-ones with the general Formula IA is given in Scheme 2. The reaction of appropriately functionalized cyclohexane-1,3-dione derivatives 1 with ammonium acetate/acetic acid in benzene gave the corresponding 3-amino-cyclohex-2-enone derivatives 5. Compound 5 was then reacted with ethyl propiolate and cyclization was achieved with phosphoryl chloride gave the 2-chloro-substituted quinolin-5-one derivatives 7. Substitution of the chloro-substituent with either alkoxide or a primary amine yielded compounds of Formula IA bearing an amino or ether linker. Alternatively, compound 5 can also be treated with appropriately functionalized propenones in the presence of Pd/C to give additional 3-unsubstituted compounds corresponding to the general Formula IA.

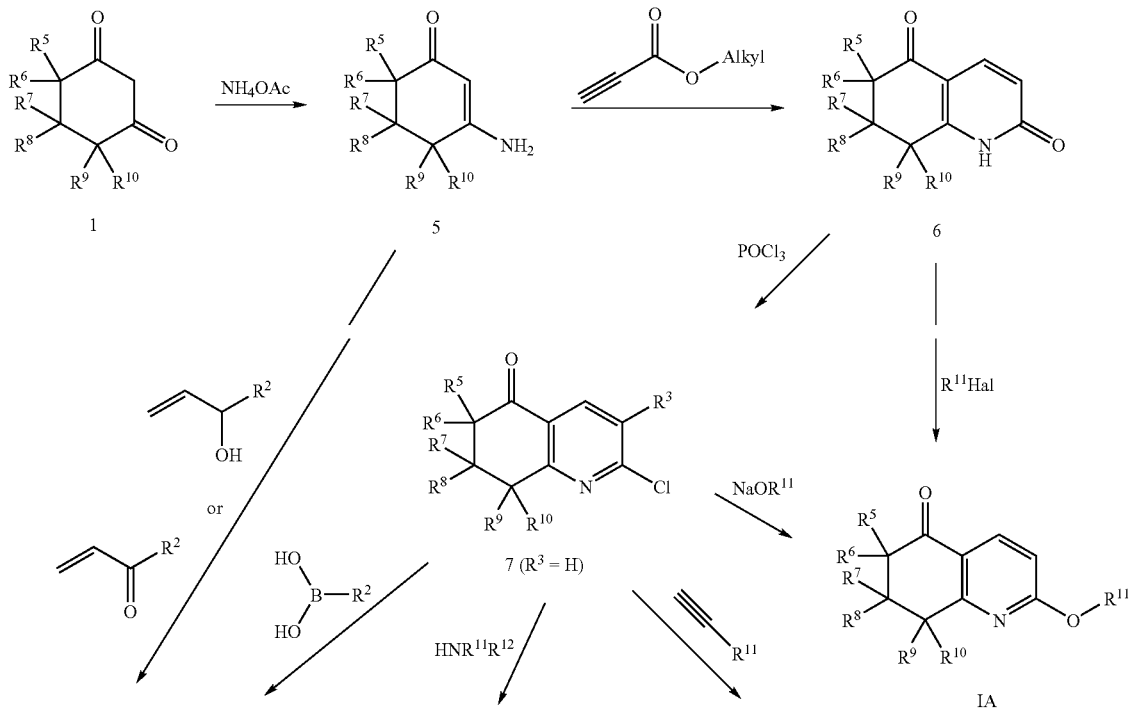

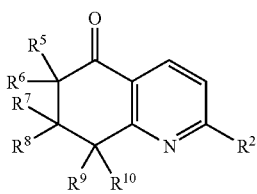

IA

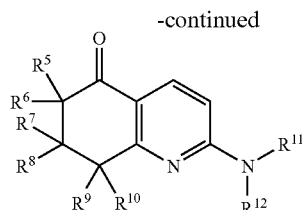

IA

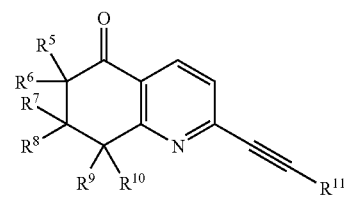

IA

It will be apparent to those skilled in the art that the described synthetic procedures are merely representative in nature and that alternative synthetic processes are known to one of ordinary skill in organic chemistry.

Experimental Part

The compounds and their preparation of the present invention will be better understood in connection with the following examples, which are intended as an illustration of and not a limitation upon the scope of the invention.

Hereinafter, "DMF" is defined as N,N-dimethylformamide, "HCl" as hydrochloric acid, "DMSO" as dimethylsulfoxide and "TMS" as tetramethylsilane.

Preparation 1

7,7-Dimethyl-5-oxo-2-thioxo-1,2,5,6,7,8-hexahydroquinoline-3-carbonitrile

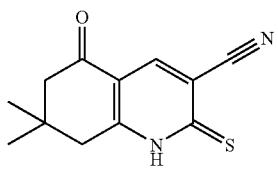

The title compound was obtained according to (Abu-Shanab, F. A.; Redhouse, A. D.; Thompson, J. R.; Wakefield, B. J. *Synthesis*. 1995, 557) as a yellow solid in 52% yield.

Preparation 2

5-Oxo-2-thioxo-1,2,5,6,7,8-hexahydroquinoline-3-carbonitrile

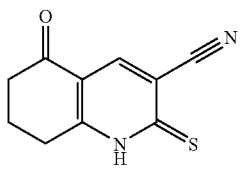

Prepared in 52% yield from cyclohexane-1,3-dione in analogy to the procedure described for 7,7-dimethyl-5-oxo-2-thioxo-1,2,5,6,7,8-hexahydroquinoline-3-carbonitrile synthesis.

Preparation 3

7,7-Dimethyl-2-methylsulfanyl-5-oxo-5,6,7,8-tetrahydroquinoline-3-carbonitrile

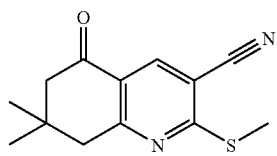

In analogy to the procedure described in Example 1, 7,7-dimethyl-5-oxo-2-thioxo-1,2,5,6,7,8-hexahydroquinoline-3-carbonitrile was treated with iodomethane to give the title compound in 89% yield.

Physical characteristics are as follows:
$^1$H NMR (CDCl$_3$, TMS) δ: 1.12, 2.54, 2.68, 3.03, 8.32.

Preparation 4

3-Amino-5,5-dimethylcyclohex-2-en-1-one

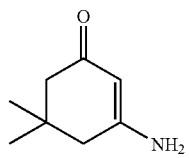

The title compound was prepared according to (Baraldi, P. G.; Simoni, D.; Manfredini, S.; *Synthesis* 1983, (11) 902-903) as a colorless solid in 76% yield.

Preparation 5

7,7-Dimethyl-7,8-dihydro-1H,6H-quinoline-2,5-dione

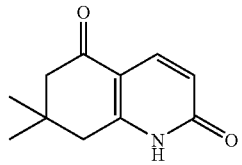

In analogy to (Pettit, G. R.; Fleming, W. C.; Paull, K. D. *J. Org. Chem.* 1968, 33 (3) 1089-1092), 3-amino-5,5-dimethylcyclohex-2-en-1-one was reacted with ethyl propio-late to give the title compound as a light brown solid in 78.5% yield.

Physical characteristics are as follows:

$^1$H NMR (CDCl$_3$, TMS) δ: 1.14, 2.42, 2.82, 6.47, and 8.04.

Preparation 6

2-Chloro-7,7-dimethyl-7,8-dihydro-6H-quinolin-5-one

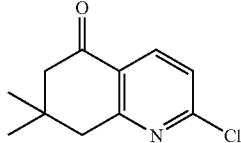

In analogy to (Shanazarov, A. K.; Kuzovkin, V. A.; Chistjakov, V. V.; Granik, V. G. *Khim. Geterotsikl. Soedin.* 1991, (1) 86-92) 7,7-dimethyl-7,8-dihydro-1H,6H-quinoline-2,5-dione was treated with phosphoryl chloride (POCl$_3$) to give the title compound as a gray solid in 60% yield.

Physical characteristics are as follows:

$^1$H NMR (CDCl$_3$, TMS) δ: 1.11, 2.54, 3.01, 7.30, and 8.30.

Preparation 7

3-Amino-5-ethylcyclohex-2-en-1-one

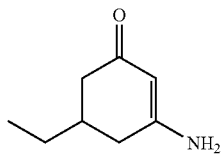

In close analogy to (Baraldi, P. G.; Simoni, D.; Manfredini, S.; *Synthesis* 1983, (11) 902-903) 5-ethylcyclohexane-1,3-dione was reacted with ammonium acetate to give the title compound.

Physical characteristics are as follows:

$^1$H NMR (CDCl$_3$, TMS) δ: 0.93 (t, 6.5 Hz, 3H); 1.42 (m, 2H); 1.88-2.44 (m, 5H); 4.62 (br s, 2H) and 5.23 ppm (s, 1H).

Preparation 8

3-Amino-6-propylcyclohex-2-en-1-one

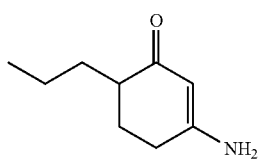

In close analogy to (Baraldi, P. G.; Simoni, D.; Manfredini, S.; Synthesis 1983, (11) 902-903) 4-propylcyclohexane-1,3-dione was reacted with ammonium acetate to give the title compound as a colorless solid.

Physical characteristics are as follow:

$^1$H NMR (CDCl3, TMS) δ: 0.91 (t, 7 Hz, 3H); 1.25-1.90 (m, 5H); 1.98-2.18 (m, 2H); 2.35 (t, 6 Hz, 2H; 4.50 (br s, 2H) and 5.19 ppm (s, 1H).

Preparation 9

3-Amino-5-isopropylcyclohex-2-en-1-one

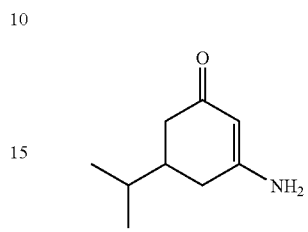

In analogy to (Baraldi, P. G.; Simoni, D.; Manfredini, S.; *Synthesis* 1983, (11) 902-903) 5-isopropylcyclohexane-1,3-dione was reacted with ammonium acetate to give the title compound as a colorless solid.

Physical characteristics are as follows:

$^1$H NMR (CDCl3, TMS) δ: 0.91 (d, 6.5 Hz); 1.48-1.65 (m, 1H); 1.84-2.39 (m, 5H); 5.04 (br s, 2H) and 5.22 ppm (s, 1H).

Preparation 10

3-Amino-6,6-dimethylcyclohex-2-en-1-one

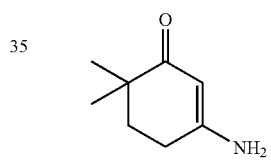

In analogy to (Baraldi, P. G.; Simoni, D.; Manfredini, S.; Synthesis 1983, (11) 902-903) 4,4-dimethylcyclohexane-1,3-dione was reacted with ammonium acetate to give the title compound as a colorless solid.

Physical characteristics are as follows:

Mp 153-154-° C.; 1H NMR (DMSO-D6, TMS) δ: 0.94 (s, 6H); 1.64 (t, 6.5 Hz, 2H); 2.28 (t, 6.5 Hz, 2H); 4.79 (s, 1H) and 6.58 ppm (br s, 2H).

Preparation 11

3-Amino-6-ethyl-6-methylcyclohex-2-en-1-one

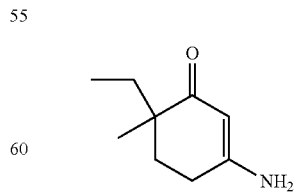

In analogy to (Baraldi, P. G.; Simoni, D.; Manfredini, S.; Synthesis 1983, (11) 902-903) 4-ethyl-4-methylcyclohexane-1,3-dione was reacted with ammonium acetate to give the title compound as a colorless solid.

Physical characteristics are as follows:

$^1$H NMR (CDCl3, TMS) δ: 0.83 (t, 6.5 Hz, 3H); 1.06 (s, 3H); 1.40-1.80 (m, 3H); 1.85-2.00 (m, 1H); 2.35 (t, 6.5 Hz, 2H); 4.31 (br s, 2H) and 5.14 ppm (s, 1H).

Preparation 12

3-Amino-5-phenylcyclohex-2-en-1-one

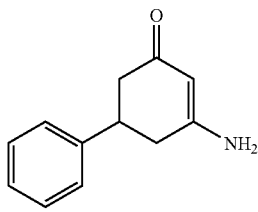

In analogy to (Baraldi, P. G.; Simoni, D.; Manfredini, S.; *Synthesis* 1983, (11) 902-903) 5-phenylcyclohexan-1,3-dione was reacted with ammonium acetate to give the title compound as a colorless solid.

Physical characteristics are as follows:

$^1$H NMR (CDCl$_3$, TMS) δ: 2.40-2.75 (m, 4H); 3.28-3.45 (m, 1H); 4.58 (br s, 2H); 5.34 (s, 1H) and 7.23-7.42 ppm (m, 5H).

Preparation 13

3-Amino-4,6,6-trimethylcyclohex-2-en-1-one

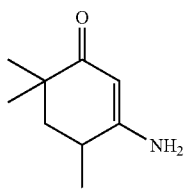

In close analogy to (Baraldi, P. G.; Simoni, D.; Manfredini, S.; Synthesis 1983, (11) 902-903) 4,4,6-trimethylcyclohexane-1,3-dione was reacted with ammonium acetate to give the title compound as a colorless solid.

Physical characteristics are as follows:

$^1$H NMR (CDCl3, TMS) δ: 1.10 (s, 6H); 1.20 (d, 6 Hz, 3H); 1.60-1.79 (m, 2H); 2.60-2.80 (m, 1H); 4.60 (br s, 2H) and 5.10 ppm (s, 1H).

Preparation 14

7-Phenyl-7,8-dihydro-1H,6H-quinoline-2,5-dione

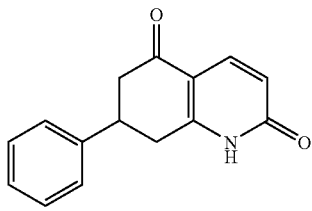

In analogy to (Pettit, G. R.; Fleming, W. C.; Paull, K. D. *J. Org. Chem.* 1968, 33 (3) 1089-1092), 3-amino-5-phenylcyclohex-2-en-1-one reacted with ethyl propiolate to give the title compound as a colorless solid.

Physical characteristics are as follows:

Mp 273-274° C.; $^1$H NMR (CDCl$_3$, TMS) δ: 2.68-3.95 (m, 2H); 3.17 (d, 8 Hz, 2H); 3.40-3.60 (m, 1H); 6.46 (d, 9 Hz, 1H); 7.25-7.42 (m, 5H) and 8.07 ppm (d, 9 Hz, 1H); Anal. Found ($C_{15}H_{13}NO_2$) (%): C, 74.9; H, 5.5; N, 5.8.

Preparation 15

2-Chloro-7-phenyl-7,8-dihydro-6H-quinolin-5-one

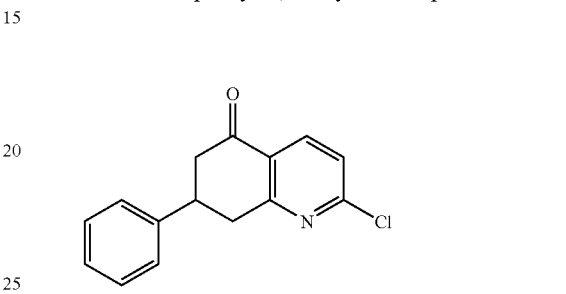

In analogy to (Shanazarov, A. K.; Kuzovkin, V. A.; Chistjakov, V. V.; Granik, V. G. *Khim. Geterotsikl. Soedin.* 1991, (1) 86-92) 7-phenyl-7,8-dihydro-1H,6H-quinoline-2,5-dione was treated with phosphoryl chloride (POCl$_3$) to give after chromatographical separation the title compound as a colorless solid.

Physical characteristics are as follows:

$^1$H NMR (CDCl$_3$, TMS) δ: 2.80-3.00 (m, 2H); 3.20-3.60 (m, 3H); 7.25-7.45 (m, 6H); 8.27 ppm (d, 8 Hz, 1H).

Preparation 16

3-Amino-5-(4-dimethylamino-phenyl)-cyclohex-2-en-1-one

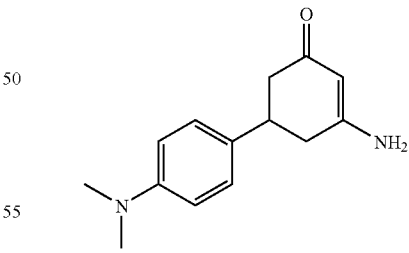

In close analogy to (Baraldi, P. G.; Simoni, D.; Manfredini, S.; Synthesis 1983, (11) 902-903) 5-(4-dimethylamino-phenyl)-cyclohexane-1,3-dione was reacted with ammonium acetate to give the title compound as a colorless solid.

Physical characteristics are as follows:

$^1$H NMR (CDCl3, TMS) δ: 2.35-2.70 (m, 4H); 2.93 (s, 6H); 3.18-3.34 (m, 1H); 4.77 (br s, 2H); 5.32 (1s, H); 6.71 (d, 9 Hz, 2H) and 7.12 ppm (d, 9 Hz, 2H).

Preparation 17

9-Amino-spiro[4.5]dec-8-en-7-one

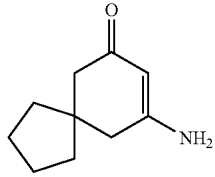

In analogy to (Baraldi, P. G.; Simoni, D.; Manfredini, S.; Synthesis 1983, (11) 902-903 spiro[4.5]decane-7,9-dione was reacted with ammonium acetate to give the title compound as a colorless solid.
Physical characteristics are as follows:
$^1$NMR (CDCl3, TMS) δ: 1.45-1.70 (m, 8H); 2.25 (s, 2H); 2.28 (s, 2H); 4.46 (br s, 2H) and 5.22 ppm (s, 1H).

Preparation 18

4-Amino-spiro[5.5]undec-3-en-2-one

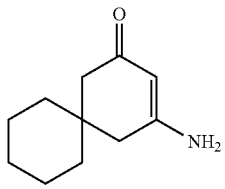

In analogy to (Baraldi, P. G.; Simoni, D.; Manfredini, S.; Synthesis 1983, (11) 902-903) spiro[5.5]undecane-2,4-dione was reacted with ammonium acetate to give the title compound as a colorless solid.
Physical characteristics are as follows:
$^1$H NMR (CDCl3, TMS) δ: 1.46-1.68 (m, 8H); 2.25 (s, 2H); 2.28 (m, 1H) 4.62 (br s, 2H) and 5.22 ppm (s, 1H).

Preparation 19

7,7-Pentamethylene-7,8-dihydro-1H,6H-quinoline-2,5-dione

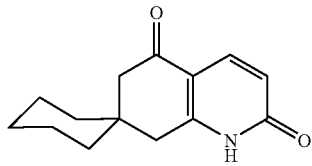

In analogy to (Pettit, G. R.; Fleming, W. C.; Paull, K. D. *J. Org. Chem.* 1968, 33 (3) 1089-1092), 4-amino-spiro[5.5]undec-3-en-2-one reacted with ethyl propiolate to give the title compound as a colorless solid.
Physical characteristics are as follows:
Mp 273-274° C.; $^1$H NMR (CDCl$_3$, TMS) δ: 1.49 (m, 10H); 2.52 (s, 2H); 2.84 (s, 2H); 6.47 (d, 9 Hz, 1H); 8.01 (d, 9 Hz, 1H) and 12.80 ppm (br s, 1H); Anal. Found (C$_{14}$H$_{17}$NO$_2$) (%): C, 72.1; H, 7.4; N, 5.9.

Preparation 20

3-Amino-4a,5,6,7,8,8a-hexahydro-4H-naphthalen-1-one

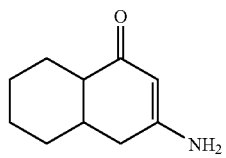

In analogy to (Baraldi, P. G.; Simoni, D.; Manfredini, S.; *Synthesis* 1983, (11) 902-903) hexahydro-naphthalene-1,3-dione (prepared from 1-cyclohex-1-enyl-ethanone according to (Chuang; Tien. *Chem. Ber.* 1936; 69; 25-29) was reacted with ammonium acetate to give the title compound as a colorless solid.
Physical characteristics are as follows:
Mp 208-210° C.; $^1$H NMR (DMSO-D$_6$, TMS) δ: 0.75-1.35 (m, 4H); 1.4-1.9 (m, 5H); 1.9-2.3 (m, 3H); 4.88 (s, 1H); 6.43 (br s, 2H).

Preparation 21

6,7,8,9,9a,10-Hexahydro-1H,5aH-benzo[g]quinoline-2,5-dione

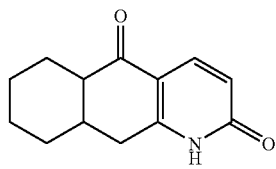

In close analogy to (Pettit, G. R.; Fleming, W. C.; Paull, K. D. *J. Org. Chem.* 1968, 33 (3) 1089-1092), 3-amino-4a,5,6,7,8,8a-hexahydro-4H-naphthalen-1-one was reacted with methyl propiolate to give the title compound as a colorless solid.
Physical characteristics are as follows:
Mp 301-303° C.; $^1$H NMR (DMSO-D$_6$, TMS) δ: 1.0-1.3 (m, 4H); 1.6-1.65 (m, 4H); 2.04 (dt, 1H); 2.17 (d, 1H); 2.62-2.72 (m, 2H); 6.21 (d, 1H); 7.73 (d, 1H); 11.92 (br s, 1H).

Preparation 22

2-Chloro-2,5a,6,7,8,9,9a,10-octahydro-1H-benzo[g]quinolin-5-one

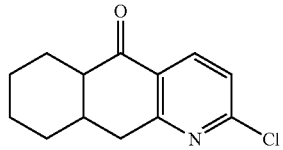

In close analogy to (Shanazarov, A. K.; Kuzovkin, V. A.; Chistjakov, V. V.; Granik, V. G. *Khim. Geterotsikl. Soedin.* 1991, (1) 86-92) 6,7,8,9,9a,10-hexahydro-1H,5aH-benzo[g]quinoline-2,5-dione was treated with phosphoryl chloride (POCl$_3$) to give after chromatographical separation the title compound as a colorless solid.

Physical characteristics are as follows:

Mp 111-113° C.; $^1$H NMR (DMSO-D$_6$, TMS) δ: 1.10-1.35 (m, 4H); 1.65-1.92 (m, 4H); 2.20 (d, 1H); 2.33 (dt, 1H); 2.85-3.00 (m, 2H); 7.47 (d, 1H); 8.14 (d, 1H). MS 236 (M+1).

Example 1

2-Butylsulfanyl-7,7-dimethyl-5-oxo-5,6,7,8-tetrahydroquinoline-3-carbonitrile

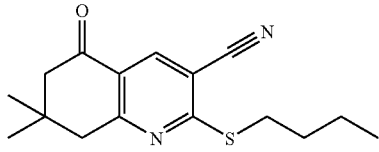

To a solution of 7,7-dimethyl-5-oxo-2-thioxo-1,2,5,6,7,8-hexahydroquinoline-3-carbonitrile (0.5 g, 2.2 mmol) in DMF (4 ml) was added 10% aqueous potassium hydroxide (1.23 ml), followed by dropwise addition of 1-bromobutane (0.24 ml, 2.2 mmol). The mixture was stirred at room temperature for 12 h, then water (12 ml) was added. The product was extracted with diethyl ether. The extract was washed with water and dried over sodium sulfate. Filtration and concentration under reduced pressure afforded the residue which was purified by flash chromatography on silica gel (petroleum ether-ethyl acetate, 10:1) to give the title compound (0.41 g, 59%) as a colorless solid.

Physical characteristics are as follows:

Mp 50-52° C.; $^1$H NMR (CDCl$_3$, TMS) δ: 0.97, 1.12, 1.49, 1.74, 2.53, 3.01, 3.32, and 8.31; Anal. Found (C$_{16}$H$_{20}$N$_2$OS*1.5H$_2$O) (%): C, 61.0; H, 7.0; N, 8.5.

Example 2

7,7-Dimethyl-5-oxo-2-propylsulfanyl-5,6,7,8-tetrahydroquinoline-3-carbonitrile

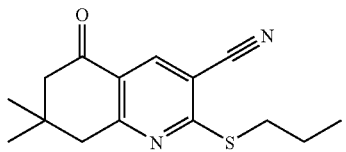

In analogy to the procedure described in Example 1, 7,7-dimethyl-5-oxo-2-thioxo-1,2,5,6,7,8-hexahydroquinoline-3-carbonitrile was treated with 1-bromopropane to give the title compound in 91% yield.

Physical characteristics are as follows:

Mp 100-102° C.; $^1$H NMR (CDCl$_3$, TMS) δ: 1.07, 1.12, 1.78, 2.53, 3.01, 3.30, and 8.31; Anal. Found (C$_{15}$H$_{18}$N$_2$OS) (%): C, 65.7; H, 6.6; N, 10.2.

Example 3

2-Isopropylsulfanyl-7,7-dimethyl-5-oxo-5,6,7,8-tetrahydroquinoline-3-carbonitrile

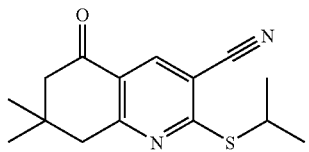

In analogy to the procedure described in Example 1, 7,7-dimethyl-5-oxo-2-thioxo-1,2,5,6,7,8-hexahydroquinoline-3-carbonitrile was treated with 2-bromopropane to give the title compound in 21% yield.

Physical characteristics are as follows:

Mp 135-136° C.; $^1$H NMR (CDCl$_3$, TMS) δ: 1.12, 1.46, 2.53, 3.01, 4.20, and 8.31; Anal. Found (C$_{15}$H$_{18}$N$_2$OS) (%): C, 65.5; H, 6.7; N, 9.8.

Example 4

7,7-Dimethyl-2-(2-methylallylsulfanyl)-5-oxo-5,6,7,8-tetrahydroquinoline-3-carbonitrile

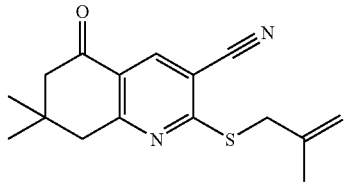

In analogy to the procedure described in Example 1, 7,7-dimethyl-5-oxo-2-thioxo-1,2,5,6,7,8-hexahydroquinoline-3-carbonitrile was treated with 3-chloro-2-methylpropene to give the title compound in 21% yield.

Physical characteristics are as follows:

Mp 78-79° C. $^1$H NMR (CDCl$_3$, TMS) δ: 1.12, 1.86, 2.54, 3.01, 4.02, 4.93, 5.10, and 8.32; Anal. Found (C$_{16}$H$_{18}$N$_2$OS) (%): C, 67.1; H, 6.3; N, 9.8.

Example 5

2-Isobutylsulfanyl-7,7-dimethyl-5-oxo-5,6,7,8-tetrahydroquinoline-3-carbonitrile

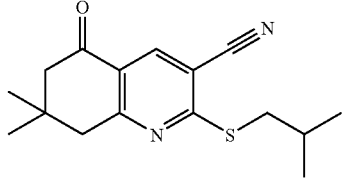

In analogy to the procedure described in Example 1, 7,7-dimethyl-5-oxo-2-thioxo-1,2,5,6,7,8-hexahydroquinoline-3-carbonitrile was treated with 1-bromo-2-methylpropane to give the title compound in 42% yield.

Physical characteristics are as follows:

Mp 75-76° C.; $^1$H NMR (CDCl$_3$, TMS) δ: 1.07, 1.12, 2.00, 2.52, 2.99, 3.23, and 8.31; Anal. Found (C$_{16}$H$_{20}$N$_2$OS) (%): C, 66.5; H, 7.0; N, 9.7.

Example 6

2-(2-Methylallylsulfanyl)-5-oxo-5,6,7,8-tetrahydro-quinoline-3-carbonitrile

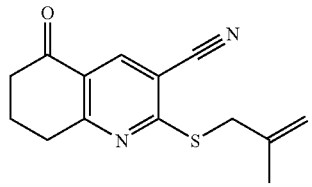

In analogy to the procedure described in Example 1, 5-oxo-2-thioxo-1,2,5,6,7,8-hexahydroquinoline-3-carbonitrile was treated with 3-chloro-2-methylpropene to give the title compound in 89% yield.

Physical characteristics are as follows:

Mp 85-86° C.; $^1$H NMR (CDCl$_3$, TMS) δ: 1.85, 2.19, 2.68, 3.12, 4.00, 4.92, 5.10, 8.34; Anal. Found (C$_{14}$H$_{14}$N$_2$OS) (%): C, 64.8; H, 5.5; N, 10.8.

Example 7

7,7-Dimethyl-5-oxo-2-piperidin-1-yl-5,6,7,8-tetrahydro-quinoline-3-carbonitrile

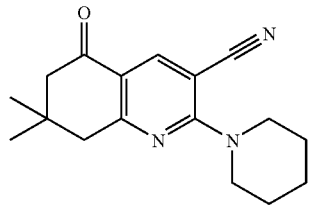

A solution of 7,7-dimethyl-2-methylsulfanyl-5-oxo-5,6,7,8-tetrahydro-quinoline-3-carbonitrile (0.25 g, 1 mmol) and piperidine (0.32 ml, 4 mmol) in dry ethanol (3 ml) was stirred at reflux for 36 h. The reaction mixture was then evaporated under reduced pressure. The residue was purified by flash chromatography on silica gel (chloroform-methanol, 50:1) to give the title compound (0.08 g, 28%) as a colorless solid.

Physical characteristics are as follows:

Mp 99-100° C.; $^1$H NMR (CDCl$_3$, TMS) δ: 1.08, 1.73, 2.45, 2.79, 3.91, and 8.33; Anal. Found (C$_{17}$H$_{21}$N$_3$O) (%): C, 71.6; H, 7.5; N, 14.4.

Example 8

2-Benzylamino-7,7-dimethyl-5-oxo-5,6,7,8-tetrahydroquinoline-3-carbonitrile hydrochloride

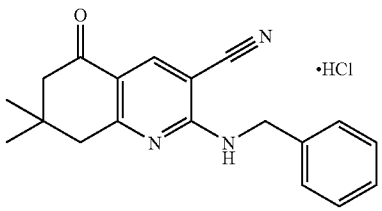

A solution of 7,7-dimethyl-2-methylsulfanyl-5-oxo-5,6,7,8-tetrahydroquinoline-3-carbonitrile (0.25 g, 1 mmol), benzylamine (0.13 g, 1.2 mmol) and sodium acetate (0.41 g, 3 mmol) in dry ethanol (3 ml) was stirred at reflux for 60 h. The reaction mixture was then evaporated under reduced pressure. The residue was purified by flash chromatography on silica gel (chloroform-methanol, 30:1) and treated with a dry HCl solution in diethyl ether to give the title compound (0.072 g, 21%) as a colorless solid.

Physical characteristics are as follows:

Mp 163-164° C.; $^1$H NMR (CDCl$_3$, TMS) δ: 1.11, 2.48, 2.95, 4.88, 7.38, and 8.38; Anal. Found (C$_{19}$H$_{19}$N$_3$O*HCl) (%): C, 66.7; H, 5.9; N, 12.3.

Example 9

2-Cyclohexyloxy-7,7-dimethyl-7,8-dihydro-6H-quinolin-5-one hydrochloride

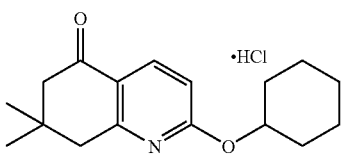

To a solution of cyclohexanol (0.2 g, 2.0 mmol) in diethyl ether (10 ml) was added sodium (0.035 g, 1.5 mmol) and it was stirred at room temperature for 2.5 h. Then 2-chloro-7,7-dimethyl-7,8-dihydro-6H-quinolin-5-one (0.21 g, 1.0 mmol) was added and the resulting mixture was stirred at 30° C. for 24 h. Water (12 ml) was added and the mixture was extracted with ethyl acetate (2×10 ml). The organic phase was washed with water (10 ml) and dried over magnesium sulphate, then it was filtered and evaporated under reduced pressure. The residue was purified by flash chromatography on silica gel (petroleum ether-ethyl acetate, 10:1) followed by treatment with a dry 0.5M HCl solution in diethyl ether to give the title compound (0.28 g, 47%) as a colorless solid.

Physical characteristics are as follows:

Mp 126-127° C.; $^1$H NMR (CDCl$_3$, TMS) δ: 1.14, 1.3-2.1, 2.53, 3.45, 5.1-5.3, 6.96, and 8.53; Anal. Found (C$_{17}$H$_{23}$NO$_2$*HCl*0.5H$_2$O) (%): C, 64.4; H, 7.5; N, 4.4.

Example 10

2-Isobutoxy-7,7-dimethyl-7,8-dihydro-6H-quinolin-5-one hydrochloride

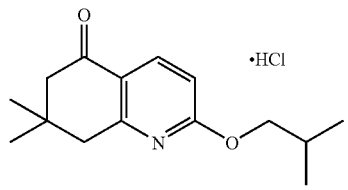

In analogy to the procedure described in Example 9, 2-chloro-7,7-dimethyl-7,8-dihydro-6H-quinolin-5-one was treated with iso-butyl alcohol to give the title compound in 35% yield.

Physical characteristics are as follows:

Mp 157-158° C.; $^1$H NMR (CDCl$_3$, TMS) δ: 1.12, 1.15, 2.28, 2.56, 3.52, 4.32, 7.06, 8.64, and 9.0-9.5; Anal. Found (C$_{15}$H$_{21}$NO$_2$*HCl) (%): C, 64.0; H, 7.8; N, 4.9.

Example 11

2-Benzyloxy-7,7-dimethyl-7,8-dihydro-6H-quinolin-5-one hydrochloride

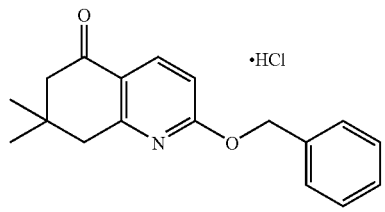

In analogy to the procedure described in Example 9, 2-chloro-7,7-dimethyl-7,8-dihydro-6H-quinolin-5-one was treated with benzyl alcohol to give the title compound in 33% yield.

Physical characteristics are as follows:

Mp 87-88° C.; $^1$H NMR (CDCl$_3$, TMS) δ: 1.15, 2.55, 3.50, 5.70, 7.07, 7.30-7.60, and 8.58; Anal. Found (C$_{18}$H$_{19}$NO$_2$*HCl*0.33 H$_2$O): C, 66.8; H, 6.2; N, 4.5.

Example 12

2-Benzylamino-7,7-dimethyl-7,8-dihydro-6H-quinolin-5-one hydrochloride

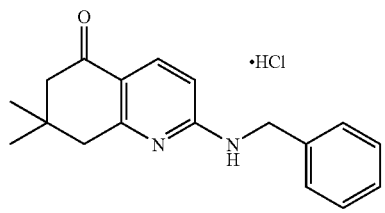

2-Chloro-7,7-dimethyl-7,8-dihydro-6H-quinolin-5-one (0.315 g, 1.5 mmol) and potassium carbonate (0.83 g, 6 mmol) were added to a solution of benzylamine (0.2 g, 1.8 mmol) in dry acetonitrile (4 ml). The mixture was stirred at reflux for 48 h. DMSO (3 ml) and sodium hydride (0.05 g) were added and heating was continued for additional 5 h. Water (10 ml) was added and the mixture was extracted with chloroform (2×10 ml). The extract was dried over sodium sulfate, filtered, and evaporated under reduced pressure. The residue was purified by flash chromatography on silica gel (chloroform-methyl alcohol, 40:1), then treated by dry HCl in diethyl ether to give the title compound (0.1 g, 21%) as a colorless solid.

Physical characteristics are as follows:

Mp 215-216° C.; $^1$H NMR (CDCl$_3$, TMS) δ: 1.14, 2.48, 3.08, 4.60, 6.64, 7.3-7.4, 8.23, and 9.67; Anal. Found (C$_{18}$H$_{20}$N$_2$O*HCl) (%): C, 68.4; H, 6.7; N, 8.5.

Example 13

7,7-Dimethyl-2-phenethyl-7,8-dihydro-6H-quinolin-5-one hydrochloride

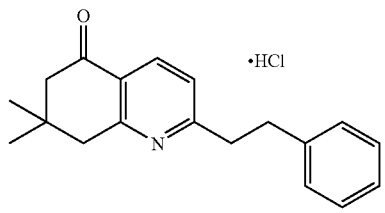

A mixture of 4 A molecular sieves (140 mg), 5-phenylpent-1-en-3-one (Martin, R.; Romea, P.; Tey, C.; Urpi, F.; Vilarrasa, J.; *SynLett.* 1997, (12) 1414-1416) (0.22 g, 1.4 mmol), 3-amino-5,5-dimethylcyclohex-2-en-1-one, and 10% Pd/C (14 mg) in toluene (4 ml) was heated at reflux for 4.5 h. It was filtered and the filtrate was evaporated under reduced pressure. The residue was purified by flash chromatography on silica gel (chloroform-methanol, 30:1), then it was treated by a dry HCl solution in diethyl ether to give the title compound (0.2 g, 45%) as a colorless solid.

Physical characteristics are as follows

Mp 173-175° C.; $^1$H NMR (CDCl$_3$, TMS) δ: 1.18, 2.63, 3.24, 3.62, 3.70, 7.15-7.30, 7.37, and 8.61; Anal. Found (C$_{19}$H$_{21}$NO*HCl) (%): C, 71.6; H, 7.0; N, 4.4.

Example 14

2-Benzyl-7,7-dimethyl-7,8-dihydro-6H-quinolin-5-one hydrochloride

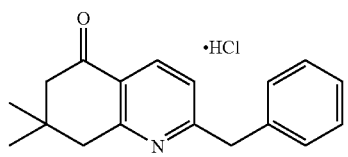

In analogy to the procedure described in Example 13, 3-amino-5,5-dimethylcyclohex-2-en-1-one was reacted with 1-phenylbut-3-en-2-one (prepared in analogy to Martin, R.;

Romea, P.; Tey, C.; Urpi, F.; Vilarrasa, J.; *SynLett.* 1997, (12) 1414-1416) to give the title compound in 33% yield.

Physical characteristics are as follows:

Mp 202-204° C.; $^1$H NMR (CDCl$_3$, TMS) δ: 1.19, 2.63, 3.65, 4.80, 7.30-7.45, 7.45, and 8.64; Anal. Found (C$_{18}$H$_{19}$NO*HCl) (%): C, 70.9; H, 6.7; N, 4.3.

Example 15

2-Benzyl-7,8-dihydro-6H-quinolin-5-one hydrochloride

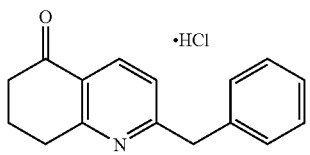

In analogy to the procedure described in Example 13, 3-aminocyclohex-2-en-1-one was reacted with 1-phenylbut-3-en-2-one to give the title compound in 50% yield.

Physical characteristics are as follows:

Mp 185-187° C.; $^1$H NMR (CDCl$_3$, TMS) δ: 2.30 (m, 2H); 2.78 (t, 6.5 Hz, 2H); 3.76 (t, 6.0 Hz, 2H); 4.75 (s, 2H); 7.20-7.50 (m, 5H); 7.50 (d, 8.0 Hz, 1H) and 8.65 ppm (d, 8.0 Hz, 1H); Anal. Found (C$_{16}$H$_{15}$NO*HCl): (%) C, 70.3; H, 5.9; N, 5.1.

Example 16

2-Phenethyl-7,8-dihydro-6H-quinolin-5-one hydrochloride

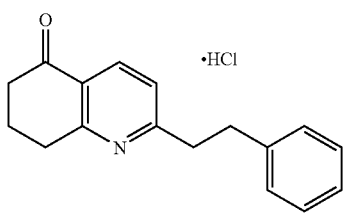

In analogy to the procedure described in Example 13, 3-aminocyclohex-2-en-1-one was reacted with 5-phenyl-pent-1-en-3-one to give the title compound in 33% yield.

Physical characteristics are as follows:

Mp 200° C. (dec.); $^1$H NMR (CDCl$_3$, TMS) δ: 2.10-2.40 (m, 2H); 2.79 (t, 6.6 Hz, 2H); 3.24 (t, 7.4 Hz, 2H); 3.60-3.80 (m, 4H); 7.20-7.40 (m, 5H); 7.35 (d, 9.0 Hz, 1H) and 8.62 ppm (d, 7.8 Hz, 1H); Anal. Found (C$_9$H$_{21}$NO*HCl*0.5H$_2$O): (%) C, 68.9; H, 6.2; N, 4.5.

Example 17

2-[2-(2-Methoxyphenyl)ethyl]-7,8-dihydro-6H-quinolin-5-one hydrochloride

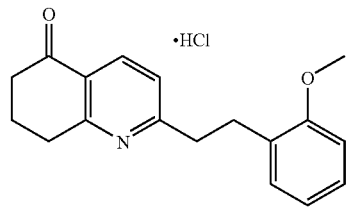

In analogy to the procedure described in Example 13, 3-aminocyclohex-2-en-1-one was reacted with 5-(2-methoxyphenyl)pent-1-en-3-one (prepared in analogy to Martin, R.; Romea, P.; Tey, C.; Urpi, F.; Vilarrasa, J.; *SynLett.* 1997, (12) 1414-1416) to give the title compound in 33% yield.

Physical characteristics are as follows:

Mp 160-162° C.; $^1$H NMR (CDCl$_3$, TMS) δ: 2.29, 2.79, 3.22, 3.66, 3.76, 3.78, 6.84, 7.16, 7.32, and 8.59; Anal. Found (C$_{18}$H$_{19}$NO$_2$*HCl): (%) C, 67.7; H, 6.3; N, 4.2.

Example 18

7,7-Dimethyl-2-styryl-7,8-dihydro-6H-quinolin-5-one hydrochloride

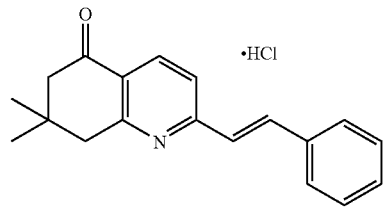

In analogy to the procedure described in Example 13, 3-amino-5,5-dimethylcyclohex-2-en-1-one was reacted with 1-phenylpenta-1,4-dien-3-one (prepared in analogy to Martin, R.; Romea, P.; Tey, C.; Urpi, F.; Vilarrasa, J.; *SynLett.* 1997, (12) 1414-1416) to give the title compound in 19% yield.

Physical characteristics are as follows:

Mp 218-220° C.; $^1$H NMR (CDCl$_3$, TMS) δ: 1.06, 2.58, 3.08, 7.49, 7.30-7.55, 7.70-7.80, 7.75, 7.92, and 8.28; Anal. Found (C$_{18}$H$_{19}$NO*HCl*0.33H$_2$O): C, 71.4; H, 6.5; N, 4.2.

Example 19

2-(Adamantan-1-yl)-7,8-dihydro-6H-quinolin-5-one hydrochloride

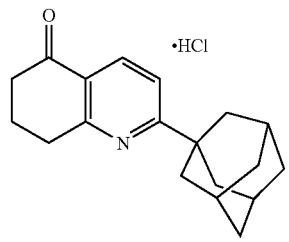

In analogy to the procedure described in Example 13, 3-aminocyclohex-2-en-1-one was reacted with 1-adamantan-1-yl-propenone (Stepanow, F. N.; Myrsina, R. A. *J. Org. Chem. USSR* (Engl. Transl.) 1966, 2, 644-647; *Zh. Org. Khim.* 1966, 2 (4) 644-648) to give the title compound in 12% yield.

Physical characteristics are as follows:

Mp 214-216° C.; $^1$H NMR (CDCl$_3$, TMS) δ: 1.80, 1.93, 2.10-2.45, 2.78, 4.05, 7.67, and 8.78; Anal. Found (C$_{19}$H$_{23}$NO*HCl): (%) C, 71.5; H, 7.6; N, 4.3.

Example 20

2-(Adamantan-1-yl)-7,7-dimethyl-7,8-dihydro-6H-quinolin-5-one hydrochloride

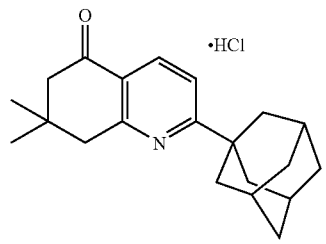

In analogy to the procedure described in Example 13, 3-amino-5,5-dimethylcyclohex-2-en-1-one was reacted with 1-adamantan-1-yl-propenone to give the title compound in 32% yield.

Physical characteristics are as follows:

Mp 210-212° C.; Anal. Found (C$_{21}$H$_{27}$NO*1.5HCl): (%) C, 69.3; H, 7.9; N, 3.7. $^1$H NMR (CDCl$_3$, TMS) δ: 1.18, 1.79, 1.93, 2.23, 2.37, 2.62, 3.90, 7.68, and 8.76.

Example 21

2-Adamantan-1-yl-6-propyl-7,8-dihydro-6H-quinolin-5-one

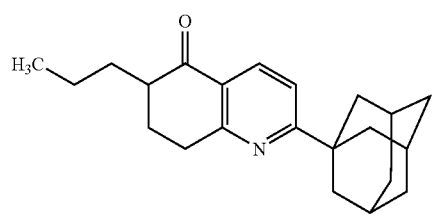

In analogy to the procedure described in Example 13, the title compound is obtained in significant yield.

Example 22

2-Benzyloxy-7-(4-chloro-phenyl)-7,8-dihydro-6H-quinolin-5-one

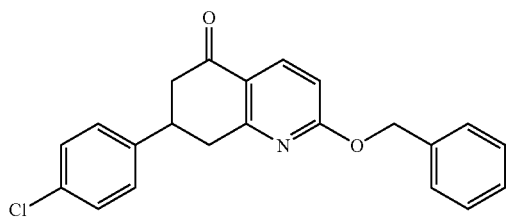

In analogy to the procedure described in Example 9, the title compound is obtained in significant yield.

Example 23

2-Isobutoxy-7-phenyl-7,8-dihydro-6H-quinolin-5-one

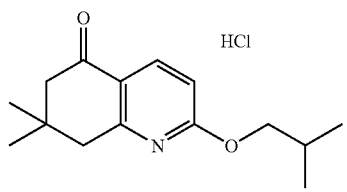

In analogy to the procedure described in Example 8, 2-chloro-7,7-dimethyl-7,8-dihydro-6H-quinolin-5-one was treated with iso-butyl alcohol to give the title compound in 35% yield.

Physical characteristics are as follows:

Mp 157-158° C.; $^1$H NMR (CDCl$_3$, TMS) δ: 1.12, 1.15, 2.28, 2.56, 3.52, 4.32, 7.06, 8.64, and 9.0-9.5; Anal. Found (C$_{15}$H$_{21}$NO$_2$*HCl) (%): C, 64.0; H, 7.8; N, 4.9.

Example 24

2-Phenoxy-7-phenyl-7,8-dihydro-6H-quinolin-5-one hydrochloride

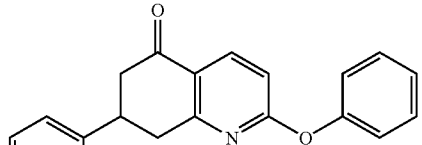

In analogy to the procedure described in Example 9, 2-chloro-7-phenyl-7,8-dihydro-6H-quinolin-5-one was treated with phenol to give the title compound as a colorless solid.

Physical characteristics are as follows:

Mp 134-135° C.; $^1$H NMR (CDCl$_3$, TMS) δ: 2.82 (dd, 17 and 12 Hz, 1H); 2.97 (dd, 17 and 4 Hz, 1H); 3.15-3.25 (m, 2H); 3.40-3.60 (m, 1H); 6.78 (d, 8.5 Hz, 1H) 7.13-7.48 (m, 10H) and 8.30 ppm (d, 8.5 Hz, 1H).

Example 25

2-Benzyloxy-7,7-pentamethylene-7,8-dihydro-6H-quinoline-5-one hydrochloride

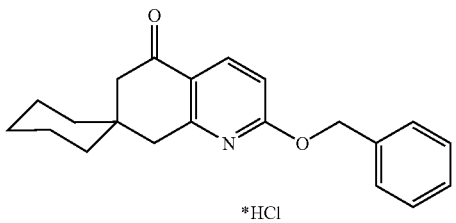

To a solution of 7,7-pentamethylene-7,8-dihydro-1H,6H-quinoline-2,5-dione (0.116 g, 0.5 mmol) in benzene (4 ml) was added silver carbonate (0.055 g, 0.2 mmol) and benzyl bromide (0.09 ml, 0.78 mmol). The mixture was stirred and heated under reflux for 8 h, then it was diluted with benzene, filtered and evaporated to dryness. The residue was treated by dry HCl solution in diethyl ether to give the title compound (0.1 g, 55%) as a colorless solid.

Physical characteristics are as follows:

Mp 276-277° C.; $^1$H NMR (CDCl$_3$, TMS) δ: 1.47 (m, 10H); 2.61 (s, 2H); 3.46 (s, 2H); 5.66 (s, 2H); 6.98 (d, 9 Hz, 1H); 7.3-7.5 (m, 5H); 7.90 (br s, 1H) and 8.45 ppm (d, 9 Hz, 1H); Anal. Found (C$_{21}$H$_{23}$NO$_2$*HCl) (%): C, 69.8; H, 6.8; N, 3.8.

Example 26

5-Oxo-2-(5-phenyl-thiophen-2-yl)-5,6,7,8-tetrahydro-quinoline-3-carbonitrile

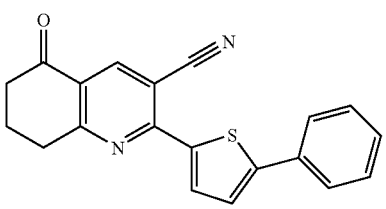

To a solution of 2-chloro-5-oxo-5,6,7,8-tetrahydro-quinoline-3-carbonitrile (300 mg, 1.46 mmol) and 5-phenyl-thiophen-2-yl-boronic acid (446 mg, 2.19 mmol) in dioxane (3 ml) under an argon atmosphere was added tetrakis(triphenylphosphine)palladium (85 mg, 0.073 mmol) and 2M aqueous K$_2$CO$_3$ (0.7 ml). The mixture was stirred at reflux till complete (TLC; hexane-EtOAc, 2:1) consumption of 2-chloro-5-oxo-5,6,7,8-tetrahydro-quinoline-3-carbonitrile. Then water was added and the mixture was extracted by dichloromethane. The extract was concentrated under reduced pressure and the residue was purified by column chromatography on silica gel (CH$_2$Cl$_2$-Hexane, 1:1), then heated under reflux in ethyl alcohol and filtered to give the title compound (220 mg, 46%) as a dark yellow solid.

Physical characteristics are as follows:

Mp 221-224° C.;

$^1$H NMR (DMSO-D$_6$, TMS) δ: 2.13 (m, 2H); 2.68 (t, 2H); 3.14 (t, 2H); 7.40 (t, 1H); 7.47 (t, 2H); 7.70 (d, 1H); 7.77 (d, 2H); 8.25 (d, 1H); 8.54 (s, 1H).

Example 27

2-Adamantan-1-yl-7,7-pentamethylene-7,8-dihydro-6H-quinoline-5-one hydrochloride

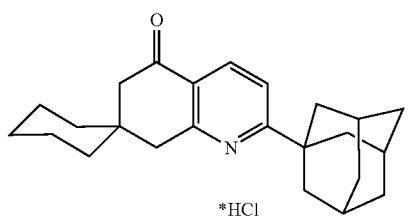

In analogy to the procedure described in Example 13, 4-amino-spiro[5.5]undec-3-en-2-one reacted with 1-adamantan-1-yl-propenone to give the title compound as a colorless solid.

Physical characteristics are as follows:

Mp 221-222° C.; $^1$H NMR (CDCl$_3$, TMS) δ: 1.47 (br s, 10H) 1.70-2.00 (m, 6H); 2.22 (br s, 3H); 2.36 (br s, 6H); 2.70 (s, 2H); 3.97 (s, 2H); 7.66 (d, 7.5 Hz, 1H) and 8.72 ppm (d, 7.5 Hz, 1H); Anal. Found (C$_{24}$H$_{31}$NO*HCl*2H$_2$O) (%): C, 68.3; H, 8.3; N, 3.1.

Example 28

2-Ethoxy-7,7-pentamethylene-7,8-dihydro-6H-quinoline-5-one

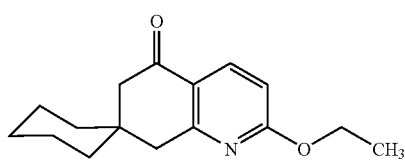

In analogy to the procedure described in Example 25, the title compound is obtained in significant yield.

Example 29

2-(2-Hydroxyethoxy)-1-yl-7-7-pentamethylene-7,8-dihydro-6H-quinoline-5-one

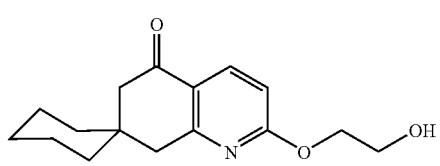

In analogy to the procedure described in Example 9, the title compound is obtained in significant yield.

Example 30

2-Isopropyl-7,7-dimethyl-7,8-dihydro-6H-quinolin-5-one

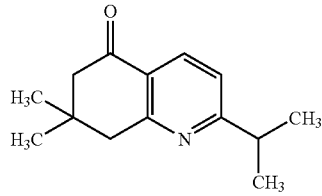

In analogy to the procedure described in Example 13, the title compound is obtained in significant yield.

Example 31

2-Benzyloxy-7-ethyl-7,8-dihydro-6H-quinolin-5-one

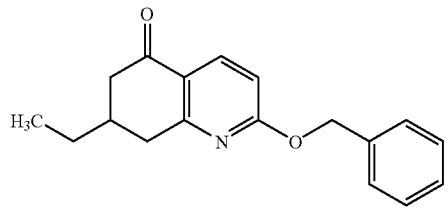

In analogy to the procedure described in Example 25, the title compound is obtained in significant yield.

Example 32

7-(4-Dimethylamino-phenyl)-2-hexyl-7,8-dihydro-6H-quinolin-5-one dihydrochloride

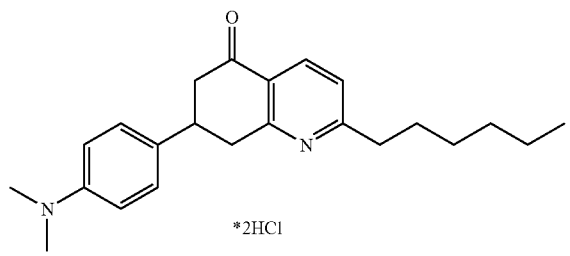

In analogy to the procedure described in Example 13, 3-amino-5-(4-dimethylamino-phenyl)-cyclohex-2-en-1-one reacted with non-1-en-3-one to give the title compound.

Physical characteristics are as follows:

Mp 195-196° C.; $^1$H NMR (CDCl$_3$, TMS) δ: 0.87 (t, 6 Hz, 3H); 1.20-1.45 (m, 6H); 1.75-1.95 (m, 2H); 3.08 (m, 2H); 3.18 (s, 6H); 3.30-3.40 (m, 2H); 3.55-3.80 (m, 2H); 4.25-4.45 (m, 1H); 7.49 (br s, 2H); 7.67 (d, 7 Hz, 1H); 7.82 (br s, 2H); 8.77 (d, 7 Hz, 1H); Anal. Found (C$_{23}$H$_{30}$N$_2$O*2HCl*H$_2$O) (%): C, 62.0; H, 7.7; N, 5.8.

Example 33

2-Cyclohexyl-7-propyl-7,8-dihydro-6H-quinolin-5-one

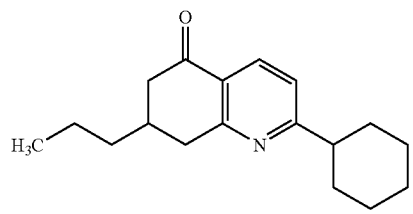

In analogy to the procedure described in Example 13, the title compound is obtained in significant yield.

Example 34

2-(4-Methoxy-phenyl)-6,6-dimethyl-7,8-dihydro-6H-quinolin-5-one

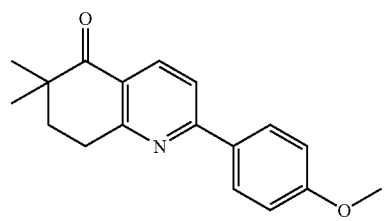

In analogy to the procedure described in Example 13, 3-amino-6,6-dimethylcyclohex-2-en-1-one reacted with 1-(4-methoxyphenyl)-propenone to give the title compound.

Physical characteristics are as follows:

Mp 158-159° C.; $^1$H NMR (CDCl$_3$, TMS) δ: 1.24 (s, 6H); 2.05 (t, 6 Hz, 2H); 3.21 (t, 6 Hz, 2H); 3.87 (s, 3H); 7.00 (d, 8.8 Hz, 2H); 7.64 (d, 8 Hz, 1H); 8.03 (d, 8.8 Hz, 2H) and 8.30 ppm (d, 8 Hz, 1H); Anal. Found (C$_{18}$H$_{19}$N$_2$O) (%): C, 76.9; H, 6.7; N, 4.7.

Example 35 cis,trans-6-Ethyl-2-(4-methoxy-phenyl)-cis,trans-6,8-dimethyl-7,8-dihydro-6H-quinolin-5-one

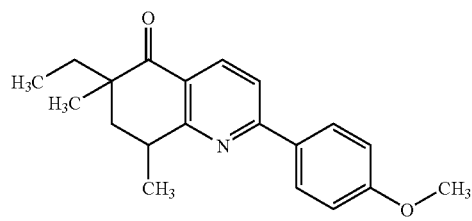

In analogy to the procedure described in Example 13, the title compound is obtained in significant yield.

Example 36

2-(3-Methoxy-phenyl)-7,7-dimethyl-7,8-dihydro-6H-quinolin-5-one

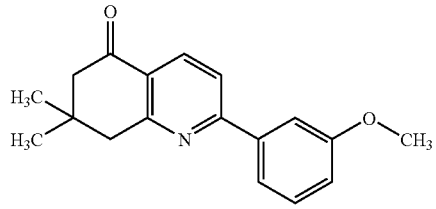

In analogy to the procedure described in Example 13, the title compound is obtained in significant yield.

Example 37

2-(3-Methoxy-phenyl)-6-ethyl-7,8-dihydro-6H-quinolin-5-one

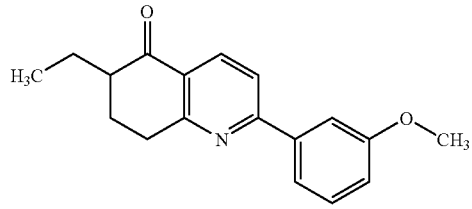

In analogy to the procedure described in Example 13, the title compound is obtained in significant yield.

Example 38

2-(3-Methoxy-phenyl)-6-methyl-7,8-dihydro-6H-quinolin-5-one

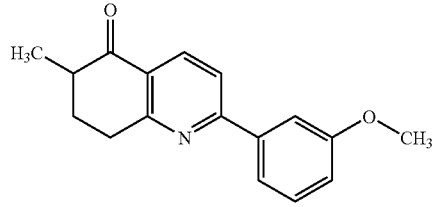

In analogy to the procedure described in Example 13, the title compound is obtained in significant yield.

Example 39

2-Adamantan-1-yl-6-ethyl-8-methyl-7,8-dihydro-6H-quinolin-5-one hydrochloride dihydrate

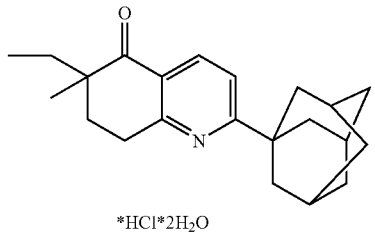

In analogy to the procedure described in Example 13, 3-amino-6-ethyl-6-methylcyclohex-2-en-1-one reacted with 1-adamantan-1-yl-propenone to give the title compound.

Physical characteristics are as follows:

Mp 131-132° C.; $^1$H NMR (CDCl$_3$, TMS) δ: 0.90 (t, 6.5 Hz, 3H); 1.21 (s, 3H); 1.55-2.10 (m, 10H); 2.22 (s, 3H); 2.36 (s, 6H); 3.80-4.15 (m, 2H); 7.66 (d, 8 Hz, 1H); 8.80 ppm (d, 8 Hz, 1H); Anal. Found (C$_{22}$H$_{29}$NO*HCl*2H$_2$O) (%): C, 67.0; H, 8.7; N, 3.3.

Example 40

2-Ethoxy-7-furan-2-yl-7,8-dihydro-6H-quinolin-5-one

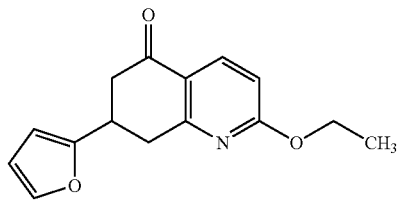

In analogy to the procedure described in Example 9, the title compound is obtained in significant yield.

Example 41

2-Adamantan-1-yl-6,6-dimethyl-7,8-dihydro-6H-quinolin-5-one hydrochloride

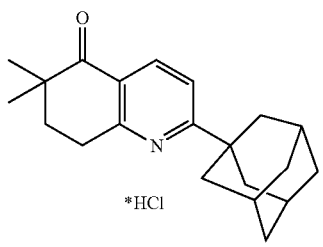

In analogy to the procedure described in Example 13, 3-amino-6,6-dimethylcyclohex-2-en-1-one reacted with 1-adamantan-1-yl-propenone to give the title compound.

Physical characteristics are as follows:

Mp 203-204° C. $^1$H NMR (CDCl$_3$, TMS) δ: 1.25 (s, 6H); 1.56 (m, 1H); 1.70-2.00 (m, 6H); 2.10 (m, 1H); 2.24 (br s, 3H); 2.38 (br s, 6H); 3.85-4.15 (m, 2H); 7.66 (d, 6 Hz, 1H); 8.78 ppm (d, 6 Hz, 1H); Anal. Found (C$_{21}$H$_{27}$NO*2HCl) (%): C, 65.5; H, 7.5; N, 3.2.

Example 42

(cis,trans) 2-Adamantan-1-yl-6-ethyl-8-methyl-7,8-dihydro-6H-quinolin-5-one and (cis,trans) 2-Adamantan-1-yl-8-ethyl-6-methyl-7,8-dihydro-6H-quinolin-5-one

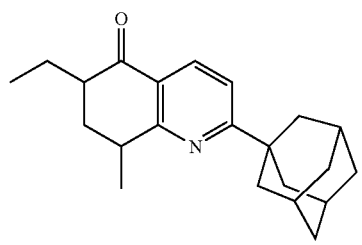

and

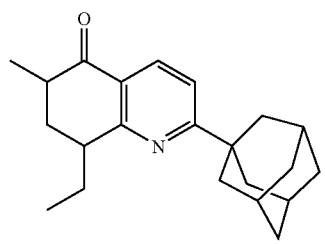

In analogy to the procedure described in Example 13, the title compound is obtained in significant yield.

Example 43 cis,trans 6-Ethyl-2-hexyl-6,8-dimethyl-7,8-dihydro-6H-quinolin-5-one

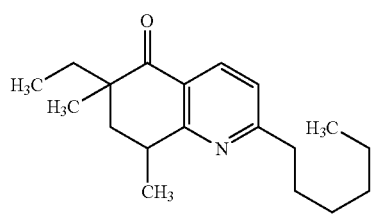

In analogy to the procedure described in Example 13, the title compound is obtained in significant yield.

Example 44

2-Cyclohexylmethyl-7,7-tetramethylene-7,8-dihydro-6H-quinolin-5-one

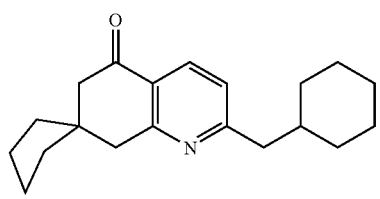

In analogy to the procedure described in Example 13, the title compound is obtained in significant yield.

Example 45

2-Hexyl-7-phenyl-7,8-dihydro-6H-quinolin-5-one

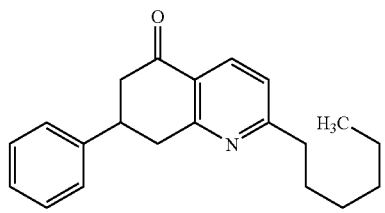

In analogy to the procedure described in Example 13, the title compound is obtained in significant yield.

Example 46

2-Cyclohexyl-7-isopropyl-7,8-dihydro-6H-quinolin-5-one

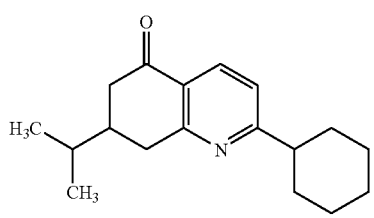

In analogy to the procedure described in Example 13, the title compound is obtained in significant yield.

Example 47

2-Cyclohexyl-6-ethyl-6-methyl-7,8-dihydro-6H-quinolin-5-one

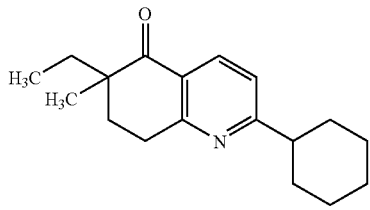

In analogy to the procedure described in Example 13, the title compound is obtained in significant yield.

Example 48

2-(3-Methoxy-phenyl)-6,6,8-trimethyl-7,8-dihydro-6H-quinolin-5-one

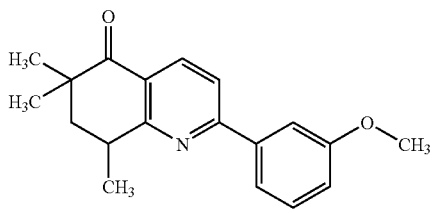

In analogy to the procedure described in Example 13, the title compound is obtained in significant yield.

Example 49 cis,trans 6-Ethyl-2-(3-methoxy-phenyl)-8-methyl-7,8-dihydro-6H-quinolin-5-one and cis,trans 8-ethyl-2-(3-methoxy-phenyl)-6-methyl-7,8-dihydro-6H-quinolin-5-one

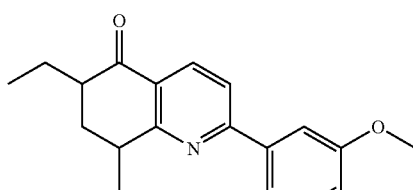

and

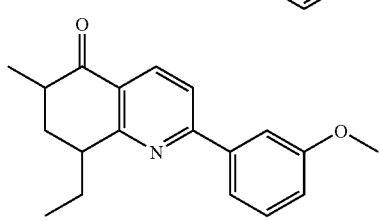

In analogy to the procedure described in Example 13, the title compound if obtained in significant yield.

Example 50 cis 2-(3-Methoxy-phenyl)-6,8-dimethyl-7,8-dihydro-6H-quinolin-5-one

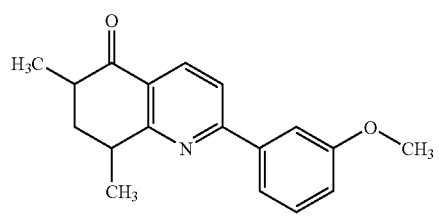

In analogy to the procedure described in Example 13, the title compound is obtained in significant yield.

Example 51

2-(3-Methoxy-phenyl)-6,6-dimethyl-7,8-dihydro-6H-quinolin-5-one

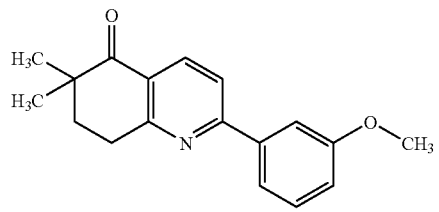

In analogy to the procedure described in Example 13, the title compound is obtained in significant yield.

Example 52

2-Hexyl-cis,trans-6,8-dimethyl-7,8-dihydro-6H-quinolin-5-one

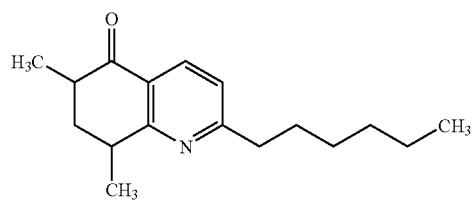

Example 53

2-Hexyl-7-propyl-7,8-dihydro-6H-quinolin-5-one

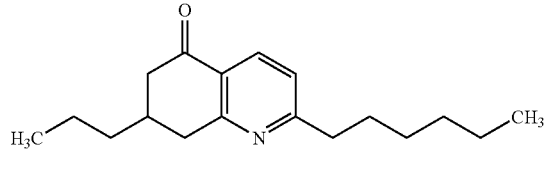

In analogy to the procedure described in Example 13, the title compound is obtained in significant yield.

Example 54

6-Ethyl-2-hexyl-7,8-dihydro-6H-quinolin-5-one

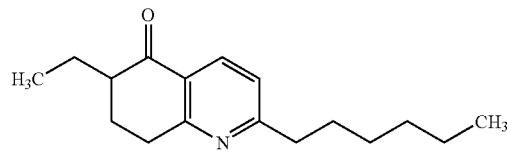

In analogy to the procedure described in Example 13, the title compound is obtained in significant yield.

Example 55

2-Hexyl-6,6,8-trimethyl-7,8-dihydro-6H-quinolin-5-one hydrochloride

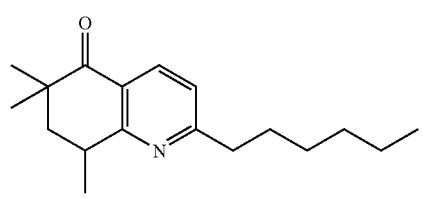

In analogy to the procedure described in Example 13, 3-amino-4,6,6-trimethylcyclohex-2-en-1-one reacted with non-1-en-3-one to give the title compound.

Physical characteristics are as follows:

Mp 199-200° C.; $^1$H NMR (CDCl$_3$, TMS) δ: 0.86 (t, 6.5 Hz, 3H); 1.17 (s, 3H); 1.29 (s, 3H); 1.23-1.55 (m, 6H); 1.75-1.90 (m, 3H); 1.88 (d, 6.5 Hz, 3H); 2.21 (dd, 14.5 and 6 Hz, 1H); 3.30-3.70 (m, 2H); 3.83-3.97 (m, 1H); 7.61 (d, 8 Hz, 1H and 8.72 ppm (d, 8 Hz, 1H); Anal. Found (C$_{18}$H$_{27}$NO*HCl) (%): C, 69.6; H, 9.3; N, 4.4.

Example 56

2-Hexyl-6,6-dimethyl-7,8-dihydro-6H-quinolin-5-one

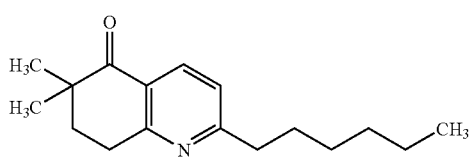

In analogy to the procedure described in Example 13, the title compound is obtained in significant yield.

Example 57 cis,trans-8-Ethyl-2-hexyl-6-methyl-7,8-dihydro-6H-quinolin-5-one and cis,trans-6-ethyl-2-hexyl-8-methyl-7,8-dihydro-6H-quinolin-5-one

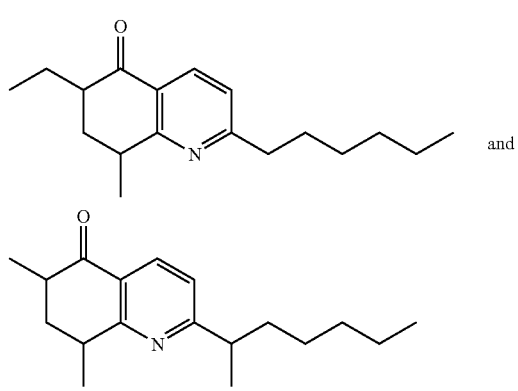

In analogy to the procedure described in Example 13, the title compound is obtained in significant yield.

Example 58

2-Hexyl-7-isopropyl-7,8-dihydro-6H-quinolin-5-one

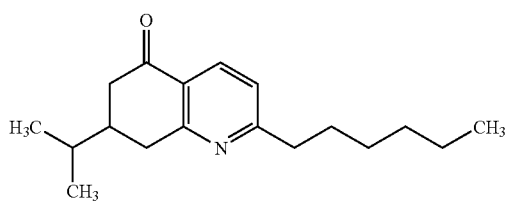

In analogy to the procedure described in Example 13, the title compound is obtained in significant yield.

Example 59

2-(3-Methoxy-phenyl)-7,7-tetramethylene-7,8-dihydro-6H-quinolin-5-one hydrochloride

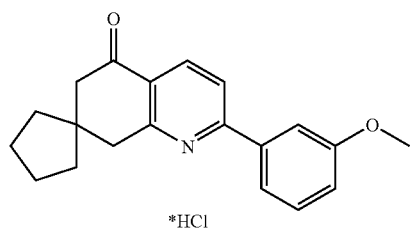

In analogy to the procedure described in Example 13, 9-amino-spiro[4.5]dec-8-en-7-one was reacted with 1-(3-methoxyphenyl)propenone to give the title compound.

Physical characteristics are as follows:

Mp 233-234° C.; $^1$H NMR (CDCl$_3$, TMS) δ: 1.45-1.95 (m, 8H); 2.77 (s, 2H); 4.04 (s, 5H); 7.20 (d, 8 Hz, 1H); 7.40-7.65 (m, 2H); 7.85-8.05 (m, 2H) and 8.70-8.87 ppm (m, 1H); Anal. Found (C$_{20}$H$_{21}$NO$_2$*HCl) (%): C, 69.0; H, 6.4; N, 3.7.

Example 60

2-(4-Methoxy-phenyl)-6-propyl-7,8-dihydro-6H-quinolin-5-one hydrochloride

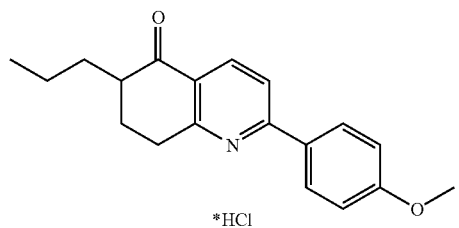

In analogy to the procedure described in Example 13, 3-amino-6-propylylcyclohex-2-en-1-one was reacted with 1-(4-methoxyphenyl)propenone to give the title compound.

Physical characteristics are as follows:

Mp 212-213° C.; $^1$H NMR (CDCl$_3$, TMS) δ: 0.97 (t, 6.6 Hz, 3H); 1.35-1.65 (m, 3H); 1.80-2.15 (m, 2H); 2.30-2.73 (m, 2H); 3.57-3.82 (m, 1H); 3.90 (s, 3H); 4.29 (dt, 19 and 6 Hz, 1H); 7.12 (d, 8 Hz, 2H); 7.91 (d, 8 Hz, 1H); 8.28 (d, 8 Hz, 2H) and 8.74 ppm (d, 8 Hz, 1H); Anal. Found (C$_{19}$H$_{21}$NO$_2$*1.5HCl) (%): C, 64.9; H, 6.4; N, 3.7.

Example 61

2-(3-Methoxy-phenyl)-6-propyl-7,8-dihydro-6H-quinolin-5-one

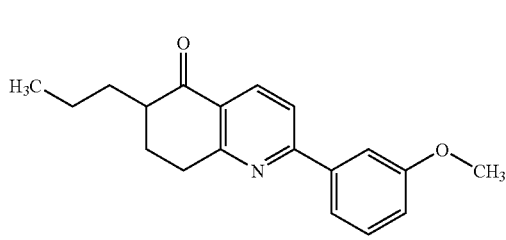

In analogy to the procedure described in Example 13, the title compound is obtained in significant yield.

Example 62

2-(4-Methoxy-phenyl)-6,6,8-trimethyl-7,8-dihydro-6H-quinolin-5-one

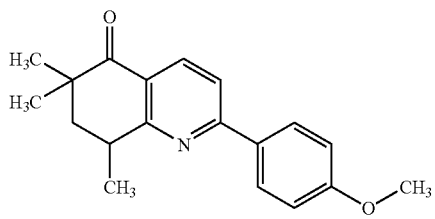

In analogy to the procedure described in Example 13, the title compound is obtained in significant yield.

Example 63

2-(4-Methoxy-phenyl)-7,7-tetramethylene-7,8-dihydro-6H-quinolin-5-one

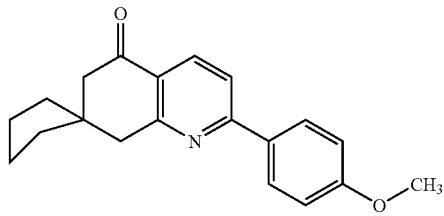

In analogy to the procedure described in Example 13, the title compound is obtained in significant yield.

Example 64

2-Hexyl-7-(3-methoxy-phenyl)-7,8-dihydro-6H-quinolin-5-one

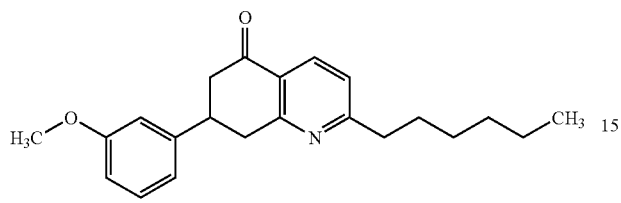

In analogy to the procedure described in Example 13, the title compound is obtained in significant yield.

Example 65

2-Hexyl-6,6-dimethyl-7,8-dihydro-6H-quinolin-5-one

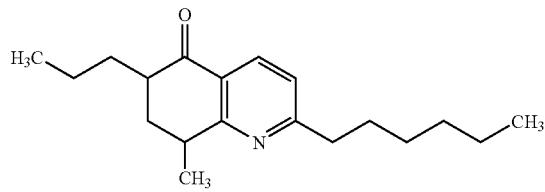

In analogy to the procedure described in Example 13, the title compound is obtained in significant yield.

Example 66

2-Benzyl-7,7-tetramethylene-7,8-dihydro-6H-quinolin-5-one hydrochloride

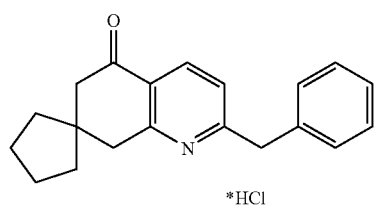

In analogy to the procedure described in Example 13, 9-amino-spiro[4.5]dec-8-en-7-one was reacted with 1-phenylbut-3-en-2-one to give the title compound.

Physical characteristics are as follows:

Mp 202-203° C.; $^1$H NMR (CDCl$_3$, TMS) δ: 1.45-1.90 (m, 8H); 2.72 (s, 2H); 3.71 (s, 2H); 4.78 (s, 2H); 7.31-7.47 (m, 6H) and 8.62 ppm (d, 8 Hz, 1H).

Example 67

2-Benzyl-6-propyl-7,8-dihydro-6H-quinolin-5-one

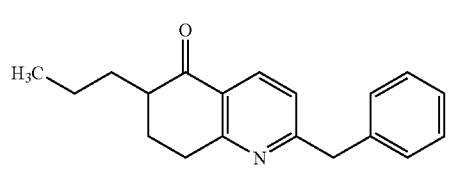

In analogy to the procedure described in Example 13, the title compound is obtained in significant yield.

Example 68

2-Benzyl-6-ethyl-7,8-dihydro-6H-quinolin-5-one

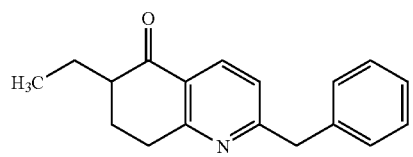

In analogy to the procedure described in Example 13, the title compound is obtained in significant yield.

Example 69

2-Benzyl-7-propyl-7,8-dihydro-6H-quinolin-5-one

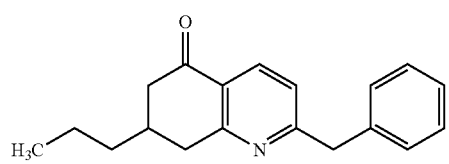

In analogy to the procedure described in Example 13, the title compound is obtained in significant yield.

Example 70

7-Ethyl-2-(4-methoxy-phenyl)-7,8-dihydro-6H-quinolin-5-one hydrochloride

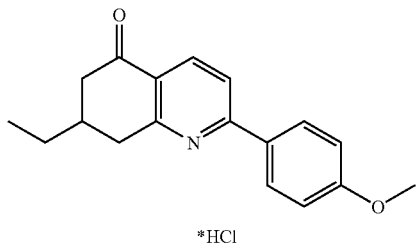

*HCl

In analogy to the procedure described in Example 13, 3-amino-5-ethylcyclohex-2-en-1-one was reacted with 1-(4-methoxyphenyl)propenone to give the title compound.

Physical characteristics are as follows:

Mp 232-233° C.; 1H NMR (CDCl3, TMS) δ: 1.06 (t, 7.4 Hz, 3H); 1.45-1.80 (m, 2H); 2.20-2.40 (m, 1H); 2.48 (dd, 16 and 12 Hz, 1H); 2.93 (d, 16 Hz, 1H); 3.32 (dd, 18 and 9 Hz, 1H); 3.91 (s, 3H); 4.40-4.58 (d, 18 Hz, 1H); 7.13 (d, 8.5 Hz, 2H); 7.90 (d, 8 Hz, 1H); 8.29 (d, 8.5 Hz, 2H) and 8.72 ppm (d, 8 Hz, 1H); Anal. Found (C18H19NO2*HCl) (%): C, 67.7; H, 6.3; N, 4.3.

Example 71

2-(4-Methoxy-phenyl)-6,8-dimethyl-7,8-dihydro-6H-quinolin-5-one

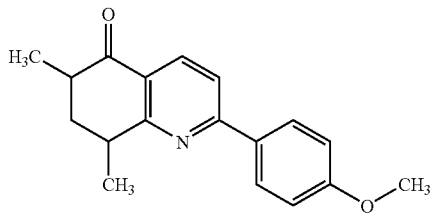

In analogy to the procedure described in Example 13, the title compound is obtained in significant yield.

Example 72

2-(4-Methoxy-phenyl)-8-methyl-6-propyl-7,8-dihydro-6H-quinolin-5-one

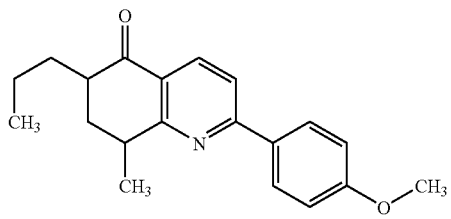

In analogy to the procedure described in Example 13, the title compound is obtained in significant yield.

Example 73

2-Benzyl-6,6-dimethyl-7,8-dihydro-6H-quinolin-5-one

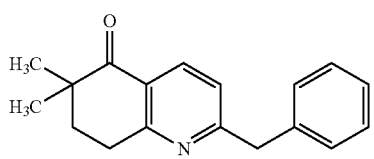

In analogy to the procedure described in Example 13, the title compound is obtained in significant yield.

Example 74

2-Benzyl-6,6,8-trimethyl-7,8-dihydro-6H-quinolin-5-one

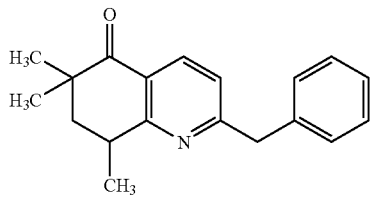

In analogy to the procedure described in Example 13, the title compound is obtained in significant yield.

Example 75

2-Benzyl-7-ethyl-7,8-dihydro-6H-quinolin-5-one

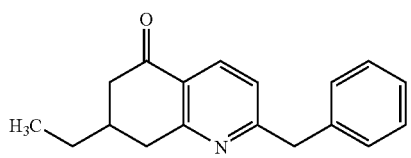

In analogy to the procedure described in Example 13, the title compound is obtained in significant yield.

Example 76

(cis,trans) 2-Benzyl-6-ethyl-8-methyl-7,8-dihydro-6H-quinolin-5-one and (cis,trans) 2-benzyl-8-ethyl-6-methyl-7,8-dihydro-6H-quinolin-5-one

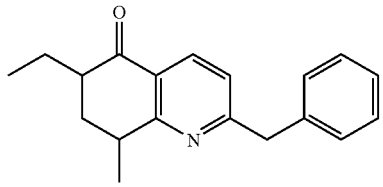

and

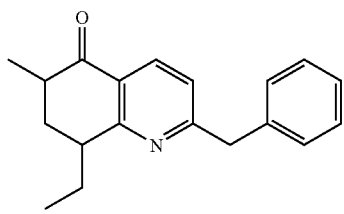

In analogy to the procedure described in Example 13, the title compound is obtained in significant yield.

Example 77

2-Cyclohexylmethyl-7,7-dimethyl-7,8-dihydro-6H-quinolin-5-one

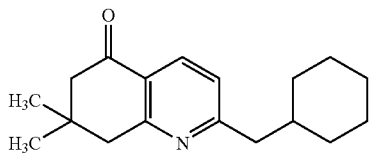

In analogy to the procedure described in Example 13, the title compound is obtained in significant yield.

Example 78

2-Cyclohexylmethyl-7-ethyl-7,8-dihydro-6H-quinolin-5-one

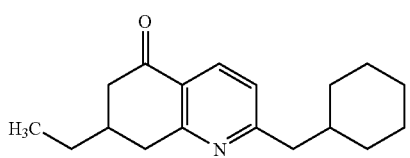

In analogy to the procedure described in Example 13, the title compound is obtained in significant yield.

Example 79

2-Cyclohexylmethyl-6,6-dimethyl-7,8-dihydro-6H-quinolin-5-one

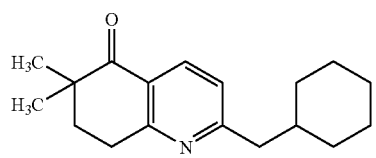

In analogy to the procedure described in Example 13, the title compound is obtained in significant yield.

Example 80

2-Cyclohexylmethyl-6-ethyl-7,8-dihydro-6H-quinolin-5-one

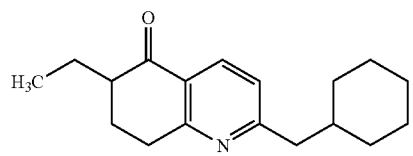

In analogy to the procedure described in Example 13, the title compound is obtained in significant yield.

Example 81

2-(3-Methoxy-benzyl)-6,6,8-trimethyl-7,8-dihydro-6H-quinolin-5-one

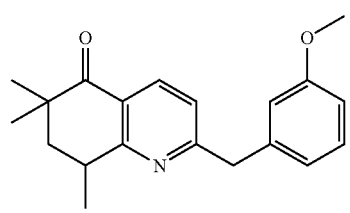

In analogy to the procedure described in Example 13, the title compound is obtained in significant yield.

Example 82

7-Isopropyl-2-pyridin-3-yl-7,8-dihydro-6H-quinolin-5-one hydrochloride

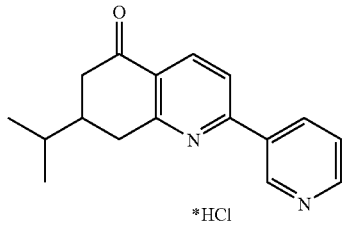

A mixture of 4 A molecular sieves (200 mg) and 1-pyridin-3-yl-prop-2-en-1-ol (270 mg, 2 mmol), 3-amino-5-isopropyl-cyclohex-2-enone (150 mg, 1 mmol), and 10% Pd/C (20 mg) in toluene (4 ml) was heated under reflux and blowing an air through a solution for 37 h. Mixture was filtered through a pad of celite and the filtrate was evaporated under reduced pressure. The residue was purified by column chromatography on silica gel (dichloromethane-methanol mixtures) then it was treated by dry HCl solution in diethyl ether to give the title compound as a colorless solid.

Physical characteristics are as follows:

Mp 130-133° C.; $^1$H NMR (CDCl$_3$, TMS) δ: 1.04 and 1.05 (both d, 6.5 Hz, 6H); 1.76 (m, 6.5 Hz, 1H); 2.01-2.23 (m, 1H); 2.48 (dd, 16.5 and 13 Hz, 1H); 2.88 (d, 16.5 Hz, 1H); 2.99 (dd, 16.5 and 13 Hz, 1H); 3.33 (d, 16.5 Hz, 1H); 7.88 (d, 6.5 Hz, 1H); 8.06 (m, 1H); 8.47 (d, 6.5 Hz, 1H); 8.82 (br. s, 1H); 9.09 (d, 6.5 Hz, 1H) and 9.60 ppm (br. s, 1H).

Example 83

2-Phenylethynyl-7,8-dihydro-6H-quinolin-5-one

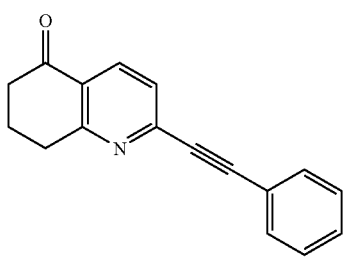

To a solution of 2-chloro-7,7-dimethyl-7,8-dihydro-6H-quinolin-5-one (0.2 g, 1.1 mmol) and ethynylbenzene (0.17 g, 1.6 mmol) in triethylamine (7 ml) under an argon atmosphere was added tetrakis(triphenylphosphine)palladium (0.02 g, 0.062 mmol). The mixture was heated at reflux for 3 h. Then it was concentrated under reduced pressure and the residue was purified by column chromatography on silica gel to give the title compound (0.04 g, 15%).

Physical characteristics are as follows:

Mp 121-122° C.; $^1$H NMR (CDCl$_3$, TMS) δ: 2.20 (m, 2H); 2.68 (t, 2H); 3.17 (t, 2H); 7.22-7.38 (m, 3H); 7.46 (d, 1H); 7.60 (d, 2H); 8.24 (d, 1H); MS 248 (M+1).

Example 84

2-Biphenyl-4-yl-7,8-dihydro-6H-quinolin-5-one

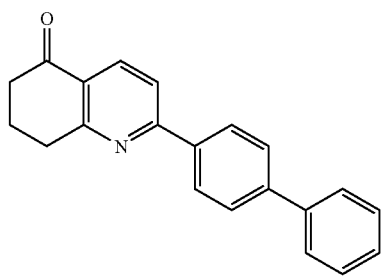

In analogy to the procedure described in Example 26, the title compound is obtained in significant yield.

Example 85

2-Hexylamino-7,7-dimethyl-5-oxo-5,6,7,8-tetrahydro-quinoline-3-carbonitrile

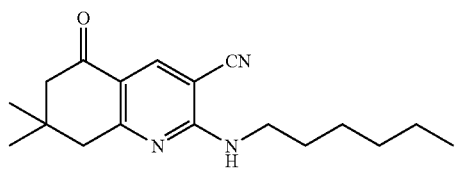

In analogy to the procedure described in Example 7 or 12, the title compound is obtained in significant yield.

Example 86

2-(4-Methoxy-phenylamino)-7,7-dimethyl-7,8-dihydro-6H-quinolin-5-one

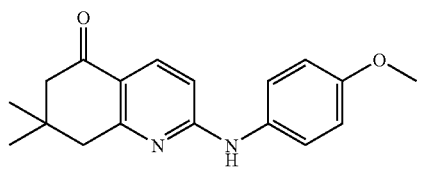

To a solution of 2-chloro-7,7-dimethyl-7,8-dihydro-6H-quinolin-5-one (0.35 g, 1.67 mmol) and 4-methoxyphenylamine (0.267 g, 2.2 mmol) in toluene (2 ml) under an argon atmosphere was added sodium tert-amylate (0.22 g, 2.0 mmol) and bis(tri-tert-butylphosphine)palladium (0.043 g, 0.084 mmol). The mixture was heated at reflux for 8 h. Then it was concentrated under reduced pressure and the residue was purified by column chromatography on silica gel to give the title compound (0.096 g, 19%) as a colorless solid.

Physical characteristics are as follows:

Mp 149-150° C.; $^1$H NMR (CDCl$_3$, TMS) δ: 1.08 (s, 6H); 2.42 (s, 2H); 2.72 (s, 2H); 3.81 (s, 3H); 6.49 (d, 1H); 6.76 (br s, 1H); 6.91 (d, 2H); 7.24 (d, 2H); 8.01 (d, 1H); MS 297 (M+1).

Example 87

7,7-Dimethyl-5-oxo-2-[(tetrahydro-furan-2-ylm-ethyl)-amino]-5,6,7,8-tetrahydro-quinoline-3-carbonitrile

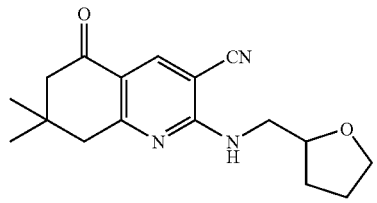

In analogy to the procedure described in Example 7 or 12, the title compound is obtained in significant yield.

Example 88

2-Cyclopentylamino-7,7-dimethyl-5-oxo-5,6,7,8-tetrahydro-quinoline-3-carbonitrile

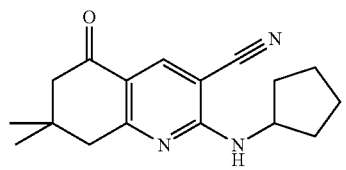

A solution of 2-chloro-7,7-dimethyl-5-oxo-5,6,7,8-tetrahydro-quinoline-3-carbonitrile (0.25 g, 1.06 mmol), cyclopentylamine (0.136 g, 1.6 mmol) and triethylamine (0.154 ml, 0.11 g, 1.1 mmol) in ethyl alcohol (3 ml) was heated at reflux for 3 h. Then water (10 ml) was added and the mixture was extracted by dichloromethane. The extract was concentrated under reduced pressure and the residue was purified by column chromatography on silica gel (CH$_2$Cl$_2$-hexane, 1:1) to give the title compound (0.145 g, 48%).

Physical characteristics are as follows:

Mp 154-156° C.; $^1$H NMR (DMSO-D$_6$, TMS) δ: 1.00 (s, 6H); 1.50-65 (m, 4H); 1.65-75 (m, 2H); 1.9-2.0 (m, 2H); 2.40 (s, 2H); 2.80 (s, 2H); 4.48 (m, 1H); 7.55 (d, 1H); 6.91 (d, 2H); 8.13 (d, 1H).

Example 89

2-(2-Methoxy-ethylamino)-5-oxo-5,6,7,8-tetrahydro-quinoline-3-carbonitrile

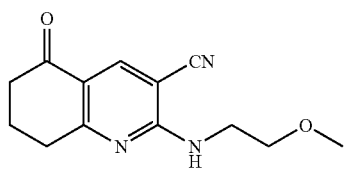

In analogy to the procedure described in Example 88, the title compound is obtained in significant yield.

Example 90

2-(Benzyl-methyl-amino)-5-oxo-5,6,7,8-tetrahydro-quinoline-3-carbonitrile

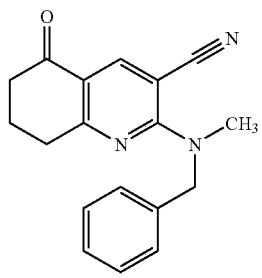

In analogy to the procedure described in Example 88, the title compound is obtained in significant yield.

Example 91

5-Oxo-2-[(tetrahydro-furan-2-ylmethyl)-amino]-5,6,7,8-tetrahydro-quinoline-3-carbonitrile

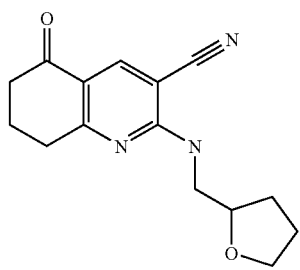

In analogy to the procedure described in Example 88, the title compound is obtained in significant yield.

Example 92

2-Cyclohexylamino-5-oxo-5,6,7,8-tetrahydro-quinoline-3-carbonitrile

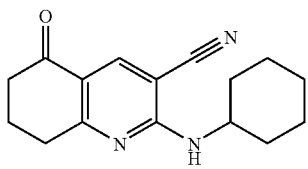

A solution of 2-chloro-5-oxo-5,6,7,8-tetrahydro-quinoline-3-carbonitrile (0.154 g, 0.75 mmol), cyclohexylamine (0.15 g, 1.5 mmol) and triethylamine (0.115 ml, 0.083 g, 0.82 mmol) in ethyl alcohol (3 ml) was heated at reflux for 3 h. Then water (10 ml) was added and the precipitated solid was filtered off and recrystallized from ethyl alcohol to give the title compound (0.12 g, 59%).

Physical characteristics are as follows:

Mp 143-145° C.; $^1$H NMR (DMSO-D$_6$, TMS) δ: 1.14 (t, 1H); 1.31 (q, 2H); 1.43 (q, 2H); 1.61 (d 1H); 1.73 (d, 2H); 1.82 (d, 2H); 2.00 (m, 2H); 2.50 (m, 2H); 2.86 (t, 2H); 3.90 (t, 4H); 4.10 (m, 1H); 7.34 (br s, 1H); 8.14 (s, 1H).

Example 93

5-Oxo-2-[(pyridin-2-ylmethyl)-amino]-5,6,7,8-tetrahydro-quinoline-3-carbonitrile

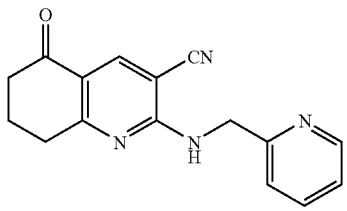

In analogy to the procedure described in Example 88, the title compound is obtained in significant yield.

Example 94

2-Azepan-1-yl-5-oxo-5,6,7,8-tetrahydro-quinoline-3-carbonitrile

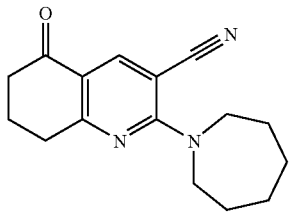

A solution of 2-chloro-5-oxo-5,6,7,8-tetrahydro-quinoline-3-carbonitrile (0.07 g, 0.34 mmol), azepane (0.07 g, 0.7 mmol) and triethylamine (0.052 ml, 0.07 g, 0.07 mmol) in ethyl alcohol (3 ml) was heated at reflux for 5 h. Then water (10 ml) was added and the precipitated solid was filtered off and recrystallized from ethyl alcohol to give the title compound (0.035 g, 38%).

Physical characteristics are as follows:

Mp 76-78° C.; $^1$H NMR (DMSO-D$_6$, TMS) δ: 1.52 (br s, 4H); 1.80 (br s, 4H); 2.02 (m, 2H); 2.50 (m, 2H); 2.86 (t, 2H); 3.90 (t, 4H); 8.16 (s, 1H).

Example 95

2-(Cyclohexyl-methyl-amino)-7,8-dihydro-6H-quinolin-5-one

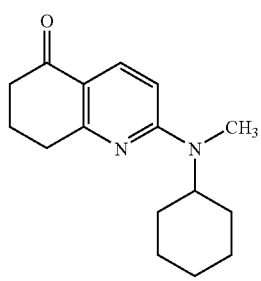

In analogy to the procedure described in Example 94, the title compound is obtained in significant yield.

Example 96

2-Phenylamino-7,8-dihydro-6H-quinolin-5-one

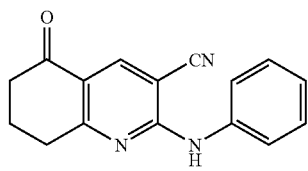

In analogy to the procedure described in Example 86, the title compound is obtained in significant yield.

Example 97

2-(Cyclohexyl-methyl-amino)-7,7-dimethyl-7,8-dihydro-6H-quinolin-5-one

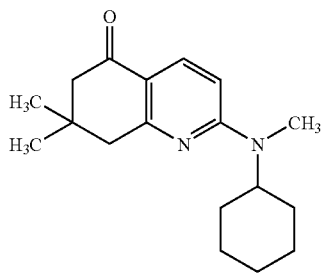

In analogy to the procedure described in Example 94, the title compound is obtained in significant yield.

Example 98

2-(Benzyl-methyl-amino)-7,7-dimethyl-5-oxo-5,6,7,8-tetrahydro-quinoline-3-carbonitrile

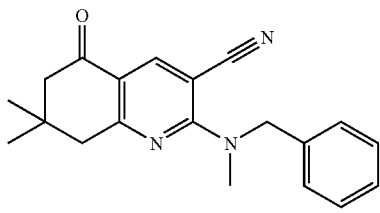

A solution of 2-chloro-7,7-dimethyl-5-oxo-5,6,7,8-tetrahydro-quinoline-3-carbonitrile (0.22 g, 0.94 mmol), benzyl (methyl)amine (0.17 g, 1.4 mmol) and triethylamine (0.14 ml, 0.1 g, 1.0 mmol) in ethyl alcohol (3 ml) was heated at reflux for 3 h. Then water (20 ml) was added and the mixture was extracted by dichloromethane. The extract was concentrated under reduced pressure and the residue was purified by column chromatography on silica gel ($CH_2Cl_2$-hexane, 1:1). The product obtained was recrystallized from ethyl alcohol to give the title compound (0.145 g, 48%).

Physical characteristics are as follows:

Mp 97-99° C.; $^1$H NMR (DMSO-$D_6$, TMS) δ: 1.00 (s, 6H); 2.43 (s, 2H); 2.80 (s, 2H); 3.23 (s, 3H); 5.03 (s, 2H); 7.25-7.30 (m, 3H); 7.32-7.37 (m, 2H); 8.21 (s, 1H).

Example 99

7,7-Dimethyl-5-oxo-2-[(pyridin-3-ylmethyl)-amino]-5,6,7,8-tetrahydro-quinoline-3-carbonitrile

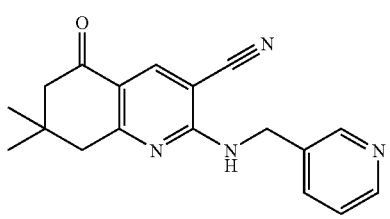

In analogy to the procedure described in Example 98, the title compound is obtained in significant yield.

Example 100

7,7-Dimethyl-5-oxo-2-(4-phenyl-piperazin-1-yl)-5,6,7,8-tetrahydro-quinoline-3-carbonitrile

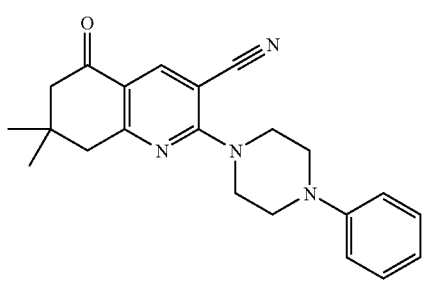

A solution of 2-chloro-7,7-dimethyl-5-oxo-5,6,7,8-tetrahydro-quinoline-3-carbonitrile (0.22 g, 0.94 mmol), 1-phenylpiperazine (0.23 g, 1.4 mmol) and triethylamine (0.14 ml, 0.1 g, 1.0 mmol) in ethyl alcohol (3 ml) was heated at reflux for 4 h. Then water (20 ml) was added and the mixture was extracted by dichloromethane. The extract was concentrated under reduced pressure and the residue was purified by column chromatography on silica gel ($CH_2Cl_2$-hexane, 1:2). The product obtained was recrystallized from ethyl alcohol to give the title compound (0.21 g, 62%).

Physical characteristics are as follows:

Mp 167-170° C.; $^1$H NMR (DMSO-$D_6$, TMS) δ: 1.00 (s, 6H); 2.45 (s, 2H); 2.84 (s, 2H); 3.33 (br s, 4H); 4.02 (br s, 4H); 6.80 (t, 1H); 6.97 (d, 2H); 7.23 (t, 2H); 8.25 (br s, 1H).

Example 101

2-Azepan-1-yl-7,7-dimethyl-7,8-dihydro-6H-quinolin-5-one

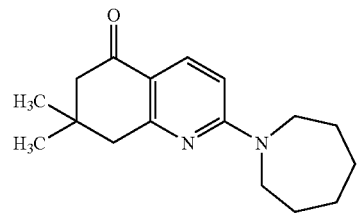

In analogy to the procedure described in Example 94, the title compound is obtained in significant yield.

Example 102

2-(4-Phenyl-piperazin-1-yl)-7,8-dihydro-6H-quinolin-5-one

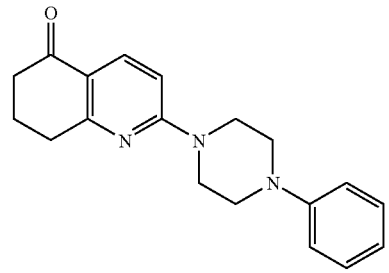

In analogy to the procedure described in Example 100, the title compound is obtained in significant yield.

Example 103

5-Oxo-2-phenylethynyl-5,6,7,8-tetrahydro-quinoline-3-carbonitrile

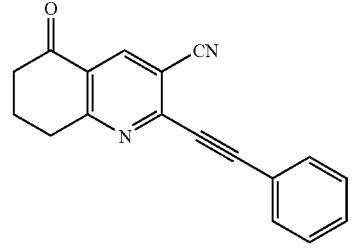

In analogy to the procedure described in Example 83, the title compound is obtained in significant yield.

Example 104

7,7-Dimethyl-2-(1-phenyl-ethylamino)-7,8-dihydro-6H-quinolin-5-one

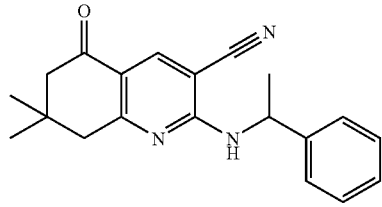

In analogy to the procedure described in Example 98, the title compound is obtained in significant yield.

Example 105

2-(3,5-Dimethoxy-benzylamino)-7,8-dihydro-6H-quinolin-5-one

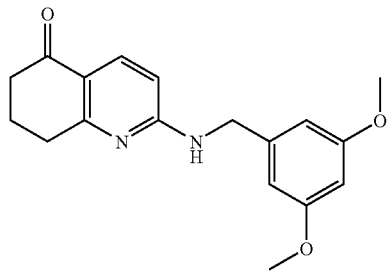

In analogy to the procedure described in Example 86, the title compound is obtained in significant yield.

Example 106

2-(3,5-Difluoro-benzylamino)-7,8-dihydro-6H-quinolin-5-one

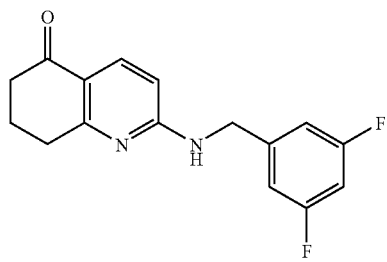

In analogy to the procedure described in Example 86, the title compound is obtained in significant yield.

Example 107

2-Biphenyl-4-yl-5-oxo-5,6,7,8-tetrahydro-quinoline-3-carbonitrile

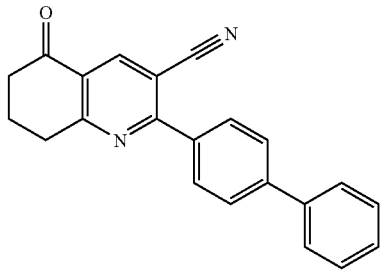

In analogy to the procedure described in Example 26, the title compound is obtained in significant yield.

Example 108

5-Oxo-2-(1-phenyl-ethylamino)-5,6,7,8-tetrahydro-quinoline-3-carbonitrile

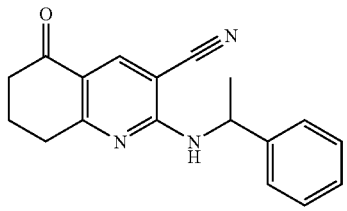

In analogy to the procedure described in Example 98, the title compound is obtained in significant yield.

Example 109

2-(3-Fluoro-benzylamino)-7,8-dihydro-6H-quinolin-5-one

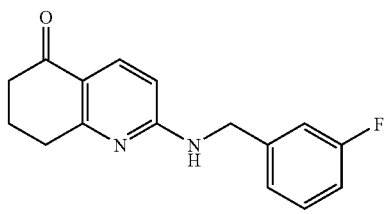

In analogy to the procedure described in Example 86, the title compound is obtained in significant yield.

Example 110

3-[(5-Oxo-5,6,7,8-tetrahydro-quinolin-2-ylamino)-methyl]-benzonitrile

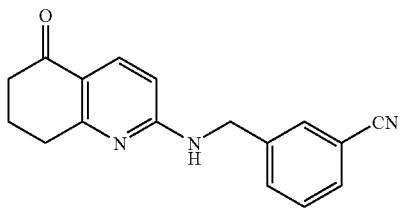

In analogy to the procedure described in Example 86, the title compound is obtained in significant yield.

Example 111

2-Phenylamino-6,7,8,9,9a,10-hexahydro-5aH-benzo[g]quinolin-5-one

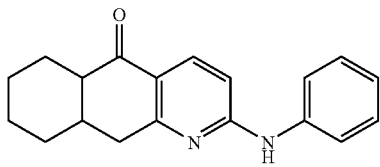

To a solution of 2-chloro-2,5a,6,7,8,9,9a,10-octahydro-1H-benzo[g]quinolin-5-one (0.4 g, 1.7 mmol) and aniline (0.204 g, 2.2 mmol) in toluene (2 ml) under an argon atmosphere was added sodium tert-amylate (0.223 g, 2.2 mmol) and bis(tri-tert-butylphosphine)palladium (0.043 g, 0.085 mmol). The mixture was heated at reflux for 8 h. Then it was concentrated under reduced pressure and the residue was purified by column chromatography on silica gel to give the title compound (0.03 g, 6%) as a colorless solid.

Physical characteristics are as follows:
Mp 214-216° C.; $^1$H NMR (DMSO-D$_6$, TMS) δ: 1.1-1.9 (m, 8H); 2.0-2.3 (m, 2H); 2.6-2.9 (m, 2H); 6.73 (d, 1H); 6.98 (t, 1H); 7.30 (t, 2H); 7.74 (d, 2H); 7.86-7.94 (m, 1H); 9.51 (br s, 1H); MS 293 (M+1).

Example 112

2-(1-Phenyl-ethylamino)-6,7,8,9,9a,10-hexahydro-5aH-benzo[g]quinolin-5-one

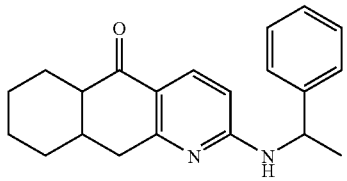

To a solution of 2-chloro-2,5a,6,7,8,9,9a,10-octahydro-1H-benzo[g]quinolin-5-one (0.4 g, 1.7 mmol) and 1-phenyl-ethylamine (0.266 g, 2.2 mmol) in toluene (2 ml) under an argon atmosphere was added sodium tert-amylate (0.223 g, 2.03 mmol) and bis(tri-tert-butylphosphine)palladium (0.043 g, 0.084 mmol). The mixture was heated at reflux for 8 h. Then it was concentrated under reduced pressure and the residue was purified by column chromatography on silica gel to give the title compound (0.13 g, 24%) as a colorless solid.

Physical characteristics are as follows:
Mp 156-158° C.; $^1$H NMR (DMSO-D$_6$, TMS) δ: 1.0-1.1 (m, 1H); 1.2-1.3 (m, 2H); 1.44 (d, 3H); 1.65-1.85 (m, 4H); 2.00 (t, 2H); 2.20 (d, 1H); 2.50-2.72 (m, 2H); 5.18 (m, 1H); 6.39 (d, 1H); 7.19 (t, 1H); 7.29 (t, 2H); 7.36 (d, 2H) 7.70 (d, 1H); 7.77 (br d, 1H); MS 321 (M+1).

Example 113

2-(Cyclohexyl-methyl-amino)-6,7,8,9,9a,10-hexahydro-5aH-benzo[g]quinolin-5-one

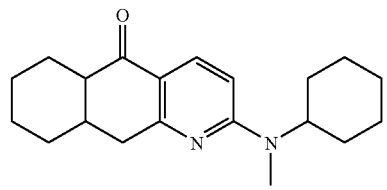

A mixture of 2-chloro-2,5a,6,7,8,9,9a,10-octahydro-1H-benzo[g]quinolin-5-one (0.29 g, 1.23 mmol) and cyclohexyl(methyl)amine (1.39 g, 12.3 mmol) was stirred at 110° C. for 9.5 h (TLC control; hexane-EtOAc, 2:1). Then the mixture was separated by column chromatography on silica gel to give the title compound (0.2 g, 52%) as a colorless oil.

Physical characteristics are as follows:
$^1$H NMR (DMSO-D$_6$, TMS) δ: 1.00-1.86 (m, 18H); 2.04 (dt, 2H); 2.21 (d, 1H); 2.60-2.75 (m, 2H); 2.93 (s, 3H); 4.43 (m, 1H); 6.57 (d, 1H); 7.82 (d, 1H); MS 313 (M+1)

Example 114

2-(4-Phenyl-piperazin-1-yl)-6,7,8,9,9a,10-hexahydro-5aH-benzo[g]quinolin-5-one

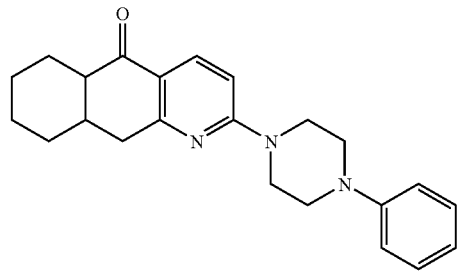

A mixture of 2-chloro-2,5a,6,7,8,9,9a,10-octahydro-1H-benzo[g]quinolin-5-one (0.29 g, 0.123 mmol) and 1-phenylpiperazine (2.0 g, 12.3 mmol) was stirred at 100° C. for 1 h (TLC control; hexane-EtOAc, 2:1). Then the mixture was separated by column chromatography on silica gel to give the title compound (0.11 g, 25%) as a pale yellow solid.

Physical characteristics are as follows:
Mp 164-166° C.; $^1$H NMR (DMSO-D$_6$, TMS) δ: 1.2-1.3 (m, 4H); 1.7-1.9 (m, 4H); 2.10 (m, 1H); 2.24 (m, 1H); 2.67-

2.80 (m, 2H); 3.25 (m, 4H); 3.85 (m, 4H); 6.77-6.83 (m, 2H); 6.98 (d, 2H); 7.24 (t, 2H); 7.88 ppm (d, 1H); MS 362 (M+1).

Example 115

2-Pyridin-3-ylethynyl-7,8-dihydro-6H-quinolin-5-one

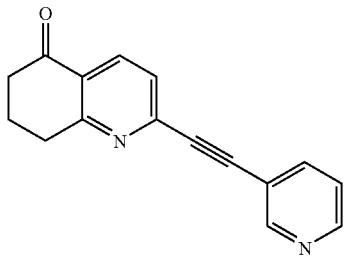

In analogy to the procedure described in Example 83, the title compound is obtained in significant yield.

Example 116

2-m-Tolylethynyl-7,8-dihydro-6H-quinolin-5-one

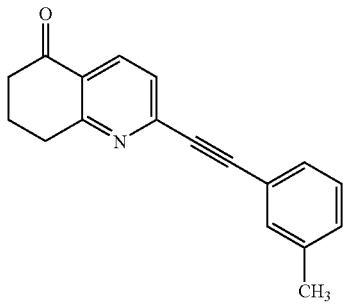

In analogy to the procedure described in Example 83, the title compound is obtained in significant yield.

Example 117

2-(3-Hydroxy-phenylethynyl)-7,8-dihydro-6H-quinolin-5-one

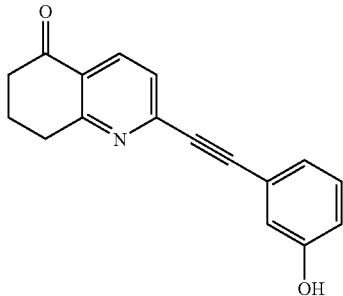

In analogy to the procedure described in Example 83, the title compound is obtained in significant yield.

Example 118

2-(3-Methoxy-phenylethynyl)-7,8-6H-quinolin-5-one

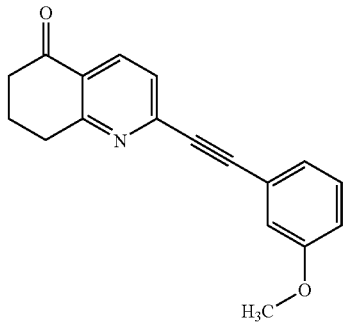

In analogy to the procedure described in Example 83, the title compound is obtained in significant yield.

Example 119

2-(3-Fluoro-phenylethynyl)-7,8-dihydro-6H-quinolin-5-one

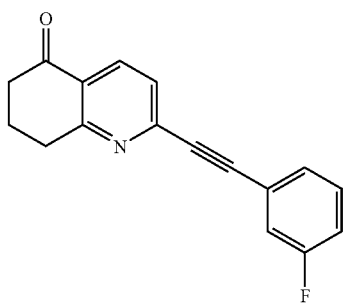

In analogy to the procedure described in Example 83, the title compound is obtained in significant yield.

Example 120

2-(3-Chloro-phenylethynyl)-7,8-dihydro-6H-quinolin-5-one

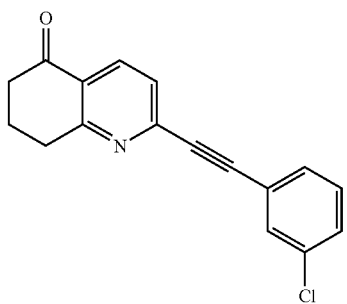

In analogy to the procedure described in Example 83, the title compound is obtained in significant yield.

Example 121

2-(3-Bromo-phenylethynyl)-7,8-dihydro-6H-quinolin-5-one

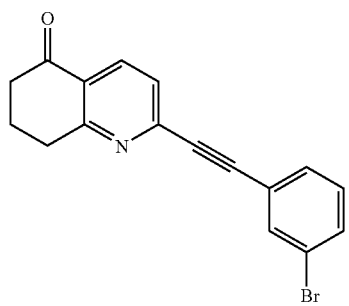

In analogy to the procedure described in Example 83, the title compound is obtained in significant yield.

Example 122

3-(5-Oxo-5,6,7,8-tetrahydro-quinolin-2-ylethynyl)-benzonitrile

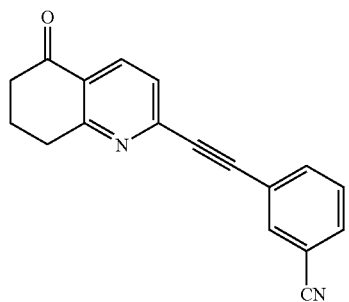

In analogy to the procedure described in Example 83, the title compound is obtained in significant yield.

Example 123

2-Thiazol-5-ylethynyl-7,8-dihydro-6H-quinolin-5-one

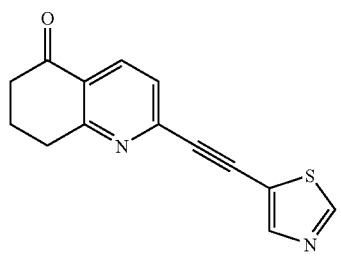

In analogy to the procedure described in Example 83, the title compound is obtained in significant yield.

Example 124

2-Oxazol-5-ylethynyl-7,8-dihydro-6H-quinolin-5-one

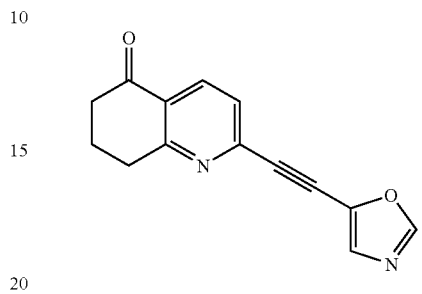

In analogy to the procedure described in Example 83, the title compound is obtained in significant yield.

Example 125

2-(2-Phenyl-oxazol-5-ylethynyl)-7,8-dihydro-6H-quinolin-5-one

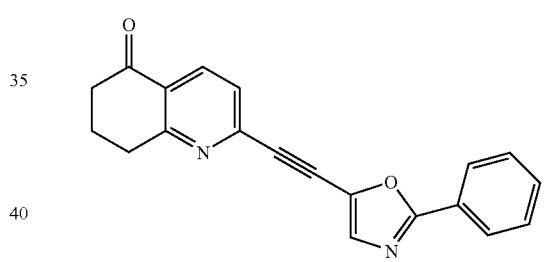

In analogy to the procedure described in Example 83, the title compound is obtained in significant yield.

Example 126

2-(2-Phenyl-thiazol-5-ylethynyl)-7,8-dihydro-6H-quinolin-5-one

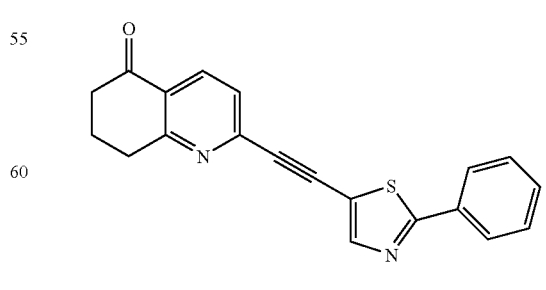

In analogy to the procedure described in Example 83, the title compound is obtained in significant yield.

Example 127

2-(3-Methoxy-4-pyridin-3-yl-phenyl)-7,8-dihydro-6H-quinolin-5-one

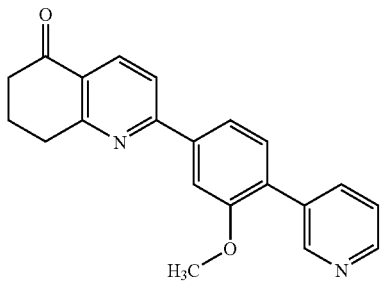

In analogy to the procedure described in Example 26, the title compound is obtained in significant yield.

Example 128

2-(3-Methoxy-4-pyridin-2-yl-phenyl)-7,8-dihydro-6H-quinolin-5-one

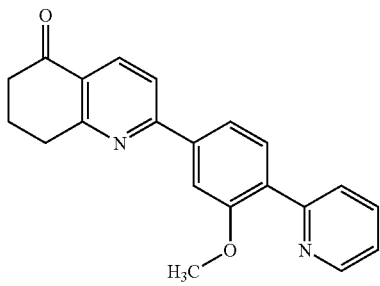

In analogy to the procedure described in Example 26, the title compound is obtained in significant yield.

Example 129

2-Phenylethynyl-6,7,8,9,9a,10-hexahydro-5aH-benzo[g]quinolin-5-one

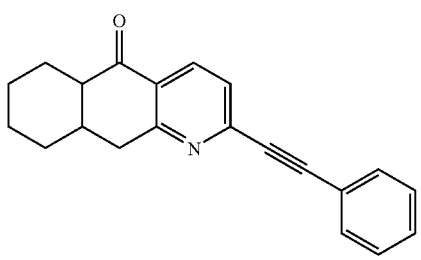

In analogy to the procedure described in Example 83, the title compound is obtained in significant yield.

Example 130

3-(5-Oxo-5,5a,6,7,8,9,9a,10-octahydro-benzo[g]quinolin-2-yl)-benzonitrile

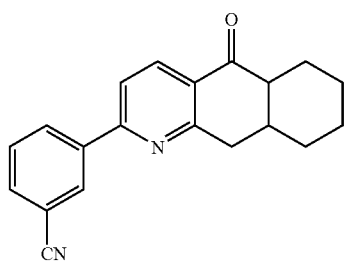

In analogy to the procedure described in Example 26, the title compound is obtained in significant yield.

Example 131

2-Pyridin-3-yl-6,7,8,9,9a,10-hexahydro-5aH-benzo[g]quinolin-5-one

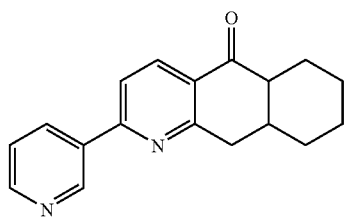

In analogy to the procedure described in Example 26, the title compound is obtained in significant yield.

Example 132

2-Piperidin-1-yl-6,7,8,9,9a,10-hexahydro-5aH-benzo[g]quinolin-5-one

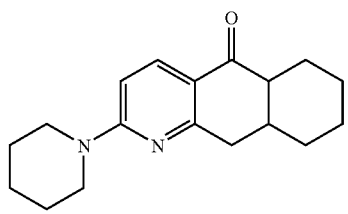

In analogy to the procedure described in Example 114, the title compound is obtained in significant yield.

Example 133

4-Chloro-5-oxo-2-(4-phenyl-piperazin-1-yl)-5,6,7,8-tetrahydro-quinoline-3-carbonitrile

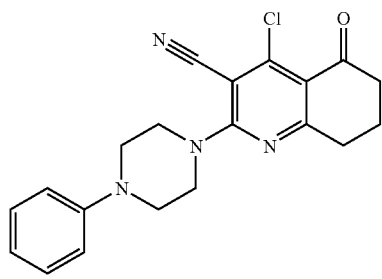

In analogy to the procedure described in Example 7 or 12, the title compound is obtained in significant yield.

Example 134

4-Bromo-5-oxo-2-(4-phenyl-piperazin-1-yl)-5,6,7,8-tetrahydro-quinoline-3-carbonitrile

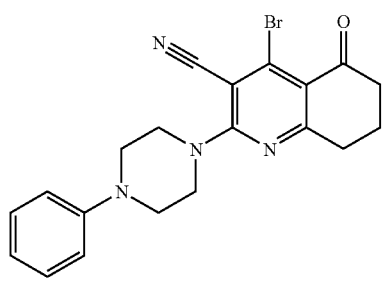

In analogy to the procedure described in Example 7 or 12, the title compound is obtained in significant yield.

Example 135

4-Methoxy-5-oxo-2-(4-phenyl-piperazin-1-yl)-5,6,7,8-tetrahydro-quinoline-3-carbonitrile

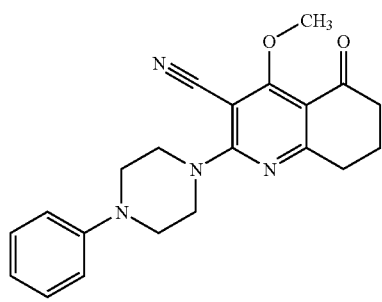

In analogy to the procedure described in Example 7 or 12, the title compound is obtained in significant yield.

Example 136

4-Ethoxy-5-oxo-2-(4-phenyl-piperazin-1-yl)-5,6,7,8-tetrahydro-quinoline-3-carbonitrile

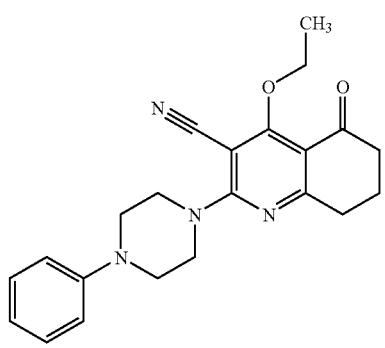

In analogy to the procedure described in Example 7 or 12, the title compound is obtained in significant yield.

Example 137

4-Ethoxy-7,7-dimethyl-5-oxo-2-(4-phenyl-piperazin-1-yl)-5,6,7,8-tetrahydro-quinoline-3-carbonitrile

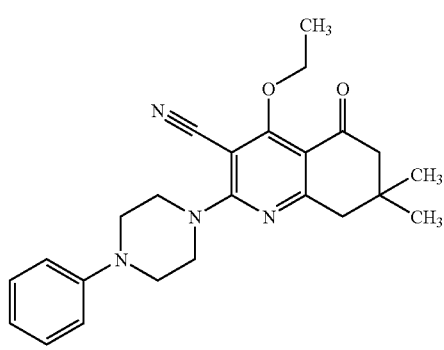

In analogy to the procedure described in Example 7 or 12, the title compound is obtained in significant yield.

Example 138

4-Methoxy-7,7-dimethyl-5-oxo-2-(4-phenyl-piperazin-1-yl)-5,6,7,8-tetrahydro-quinoline-3-carbonitrile

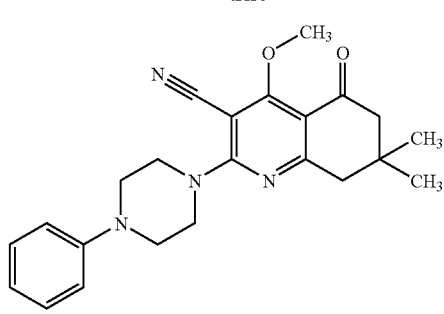

In analogy to the procedure described in Example 7 or 12, the title compound is obtained in significant yield.

Example 139

4-Chloro-7,7-dimethyl-5-oxo-2-(4-phenyl-piperazin-1-yl)-5,6,7,8-tetrahydro-quinoline-3-carbonitrile

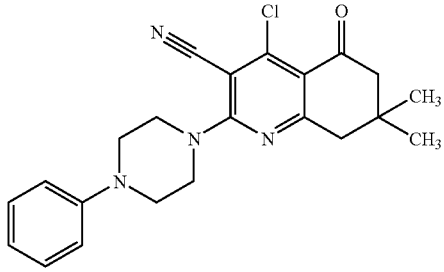

In analogy to the procedure described in Example 7 or 12, the title compound is obtained in significant yield.

Example 140

4-Bromo-7,7-dimethyl-5-oxo-2-(4-phenyl-piperazin-1-yl)-5,6,7,8-tetrahydro-quinoline-3-carbonitrile

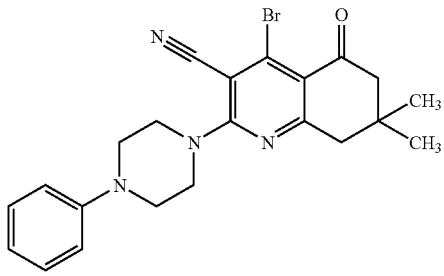

In analogy to the procedure described in Example 7 or 12, the title compound is obtained in significant yield.

Example 141

4-Bromo-7,7-dimethyl-5-oxo-2-(4-phenyl-piperidin-1-yl)-5,6,7,8-tetrahydro-quinoline-3-carbonitrile

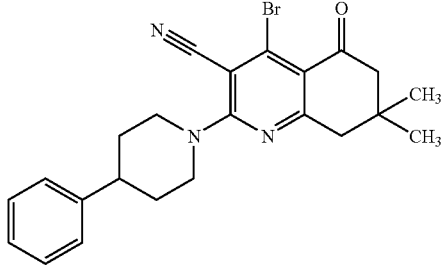

In analogy to the procedure described in Example 7 or 12, the title compound is obtained in significant yield.

Example 142

4-Chloro-7,7-dimethyl-5-oxo-2-(4-phenyl-piperidin-1-yl)-5,6,7,8-tetrahydro-quinoline-3-carbonitrile

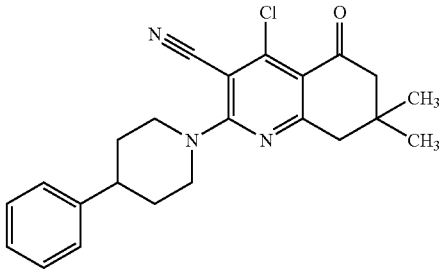

In analogy to the procedure described in Example 7 or 12, the title compound is obtained in significant yield.

Example 143

4-Methoxy-7,7-dimethyl-5-oxo-2-(4-phenyl-piperidin-1-yl)-5,6,7,8-tetrahydro-quinoline-3-carbonitrile

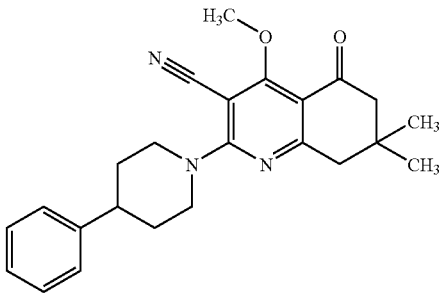

In analogy to the procedure described in Example 7 or 12, the title compound is obtained in significant yield.

Example 144

4-Ethoxy-7,7-dimethyl-5-oxo-2-(4-phenyl-piperidin-1-yl)-5,6,7,8-tetrahydro-quinoline-3-carbonitrile

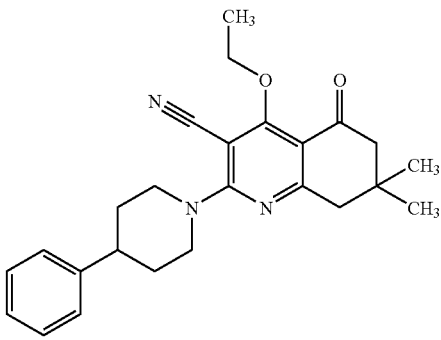

In analogy to the procedure described in Example 7 or 12, the title compound is obtained in significant yield.

Example 145

4-(2-Hydroxy-ethoxy)-7,7-dimethyl-5-oxo-2-(4-phenyl-piperidin-1-yl)-5,6,7,8-tetrahydro-quinoline-3-carbonitrile

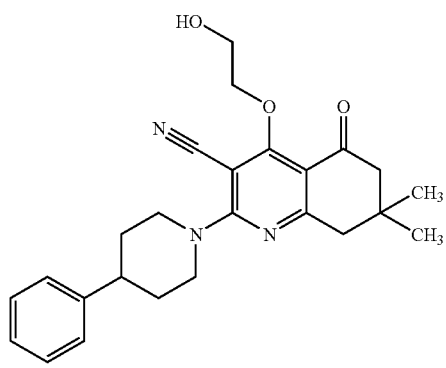

In analogy to the procedure described in Example 7 or 12, the title compound is obtained in significant yield.

Example 146

3-Chloro-7,7-dimethyl-2-(4-phenyl-piperidin-1-yl)-7,8-dihydro-6H-quinolin-5-one

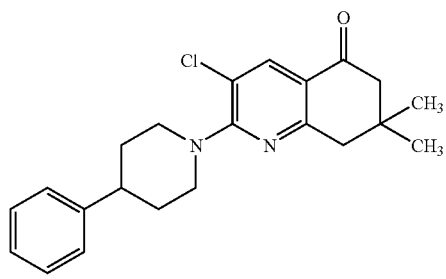

In analogy to the procedure described in Example 7 or 12, the title compound is obtained is significant yield.

Example 147

3-Bromo-7,7-dimethyl-2-(4-phenyl-piperidin-1-yl)-7,8-dihydro-6H-quinolin-5-one

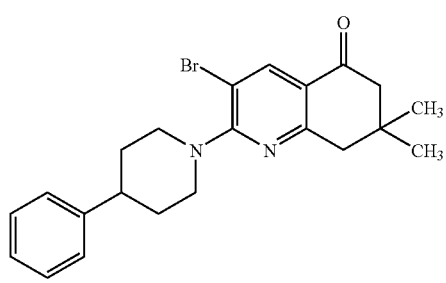

In analogy to the procedure described in Example 7 or 12, the title compound is obtained in significant yield.

Example 148

3-Fluoro-7,7-dimethyl-2-(4-phenyl-piperidin-1-yl)-7,8-dihydro-6H-quinolin-5-one

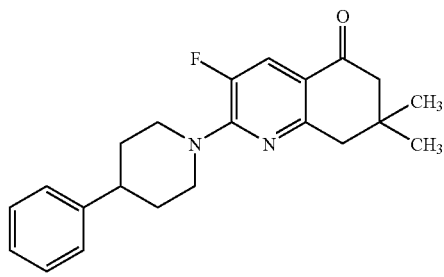

In analogy to the procedure described in Example 7 or 12, the title compound is obtained in significant yield.

Example 149

3-Methoxy-7,7-dimethyl-2-(4-phenyl-piperidin-1-yl)-7,8-dihydro-6H-quinolin-5-one

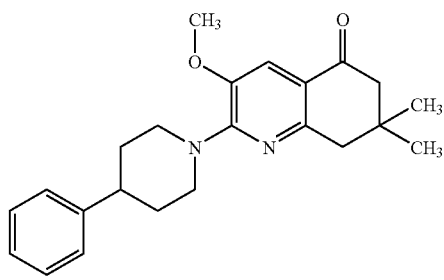

In analogy to the procedure described in Example 7 or 12, the title compound is obtained in significant yield.

Example 150

7,7-Dimethyl-3-nitro-2-(4-phenyl-piperidin-1-yl)-7,8-dihydro-6H-quinolin-5-one

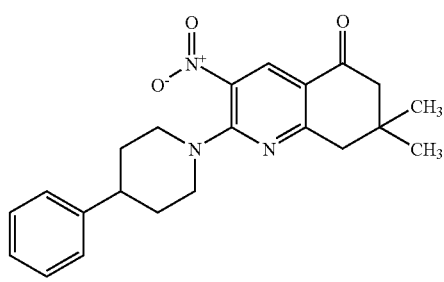

In analogy to the procedure described in Example 7 or 12, the title compound is obtained in significant yield.

Example 151

7,7-Dimethyl-3-nitro-2-(4-phenyl-piperazin-1-yl)-7,8-dihydro-6H-quinolin-5-one

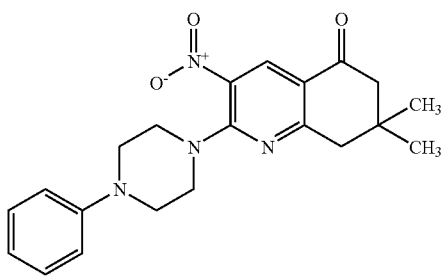

In analogy to the procedure described in Example 7 or 12, the title compound is obtained in significant yield.

Example 152

3-Fluoro-7,7-dimethyl-2-(4-phenyl-piperazin-1-yl)-7,8-dihydro-6H-quinolin-5-one

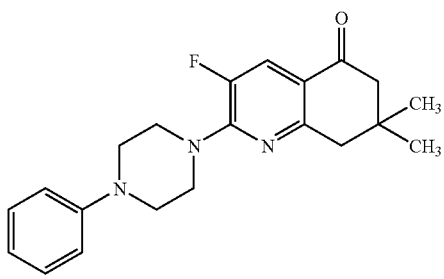

In analogy to the procedure described in Example 7 or 12, the title compound is obtained in significant yield.

Example 153

3-Bromo-7,7-dimethyl-2-(4-phenyl-piperazin-1-yl)-7,8-dihydro-6H-quinolin-5-one

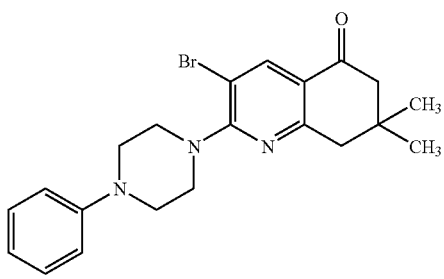

In analogy to the procedure described in Example 7 or 12, the title compound is obtained in significant yield.

Example 154

3-Chloro-7,7-dimethyl-2-(4-phenyl-piperazin-1-yl)-7,8-dihydro-6H-quinolin-5-one

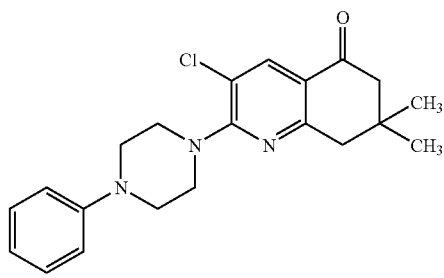

In analogy to the procedure described in Example 7 or 12, the title compound is obtained in significant yield.

Example 155

3-Methoxy-7,7-dimethyl-2-(4-phenyl-piperazin-1-yl)-7,8-dihydro-6H-quinolin-5-one

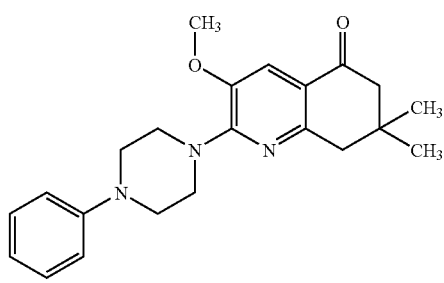

In analogy to the procedure described in Example 7 or 12, the title compound is obtained in significant yield.

Example 156

2-[4-(4-Methoxy-phenyl)-piperazin-1-yl]-7,7-dimethyl-5-oxo-5,6,7,8-tetrahydro-quinoline-3-carbonitrile

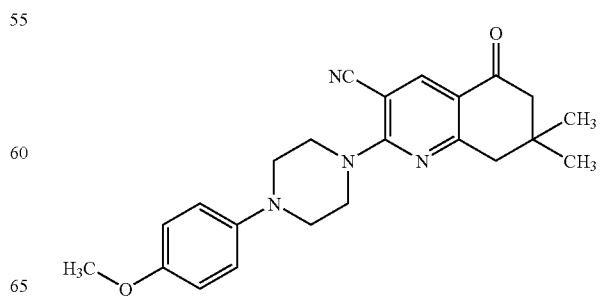

In analogy to the procedure described in Example 7 or 12, the title compound is obtained in significant yield.

Example 157

2-[4-(4-Fluoro-phenyl)-piperazin-1-yl]-7,7-dimethyl-5-oxo-5,6,7,8-tetrahydro-quinoline-3-carbonitrile

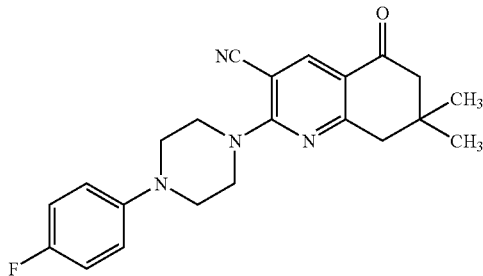

In analogy to the procedure described in Example 7 or 12, the title compound is obtained in significant yield.

Example 158

2-(5-m-Tolyl-thiazol-2-yl)-7,8-dihydro-6H-quinolin-5-one

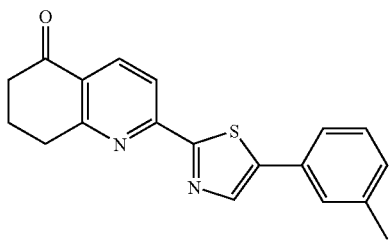

In analogy to the procedure described in Example 26, the title compound is obtained in significant yield.

Example 159

2-[5-(3-Hydroxy-phenyl)-thiazol-2-yl]-7,8-dihydro-6H-quinolin-5-one

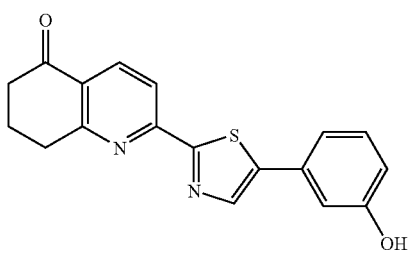

In analogy to the procedure described in Example 26, the title compound is obtained in significant yield.

Example 160

2-[5-(3-Methoxy-phenyl)-thiazol-2-yl]-7,8-dihydro-6H-quinolin-5-one

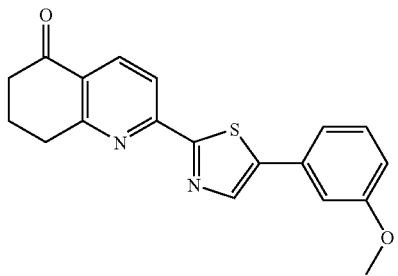

In analogy to the procedure described in Example 26, the title compound is obtained in significant yield.

Example 161

2-[5-(3-Fluoro-phenyl)-thiazol-2-yl]-7,8-dihydro-6H-quinolin-5-one

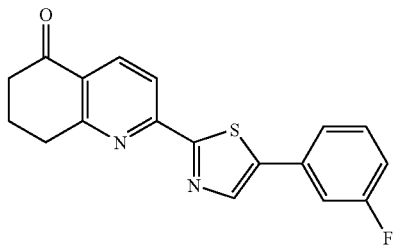

In analogy to the procedure described in Example 26, the title compound is obtained in significant yield.

Example 162

2-[5-(3-Chloro-phenyl)-thiazol-2-yl]-7,8-dihydro-6H-quinolin-5-one

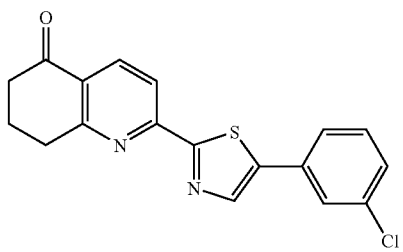

In analogy to the procedure described in Example 26, the title compound is obtained in significant yield.

Example 163

2-[5-(3-Bromo-phenyl)-thiazol-2-yl]-7,8-dihydro-6H-quinolin-5-one

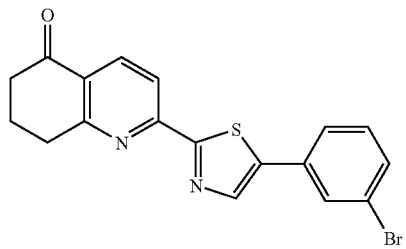

In analogy to the procedure described in Example 26, the title compound is obtained in significant yield.

Example 164

3-[2-(5-Oxo-5,6,7,8-tetrahydro-quinolin-2-yl)-thiazol-5-yl]-benzonitrile

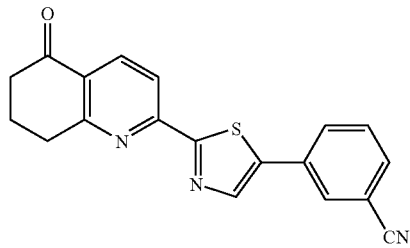

In analogy to the procedure described in Example 26, the title compound is obtained in significant yield.

Example 165

2-[5-(3,5-Dimethoxy-phenyl)-thiazol-2-yl]-7,8-dihydro-6H-quinolin-5-one

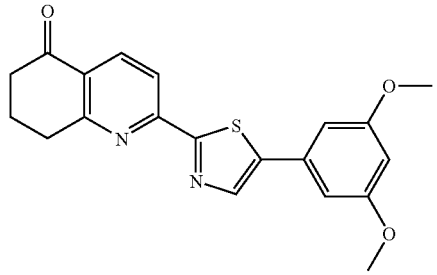

In analogy to the procedure described in Example 26, the title compound is obtained in significant yield.

Example 166

2-[2-(3,5-Dimethoxy-phenyl)-vinyl]-7,8-dihydro-6H-quinolin-5-one

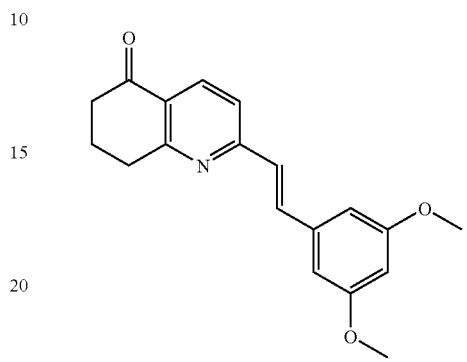

In analogy to the procedure described in Example 13, the title compound is obtained in significant yield.

Example 167

2-[5-(3-Fluoro-5-methyl-phenyl)-thiazol-2-yl]-7,8-dihydro-6H-quinolin-5-one

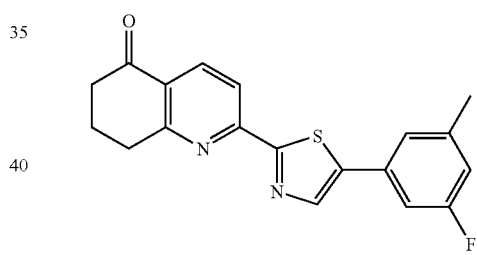

In analogy to the procedure described in Example 26, the title compound is obtained in significant yield.

Example 168

3-Fluoro-5-[2-(5-oxo-5,6,7,8-tetrahydro-quinolin-2-yl)-thiazol-5-yl]-benzonitrile

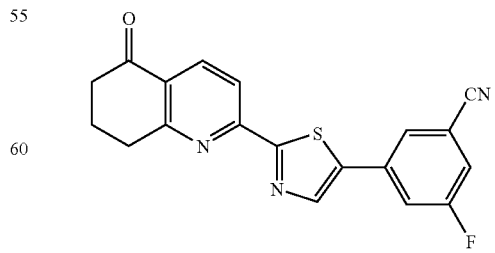

In analogy to the procedure described in Example 26, the title compound is obtained in significant yield.

Example 169

2-[5-(3-Fluoro-5-methoxy-phenyl)-thiazol-2-yl]-7,8-dihydro-6H-quinolin-5-one

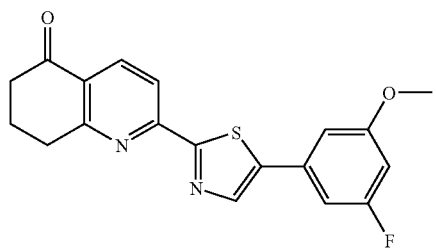

In analogy to the procedure described in Example 26, the title compound is obtained in significant yield.

Example 170

2-[5-(3-Fluoro-5-pyridin-2-yl-phenyl)-thiazol-2-yl]-7,8-dihydro-6H-quinolin-5-one

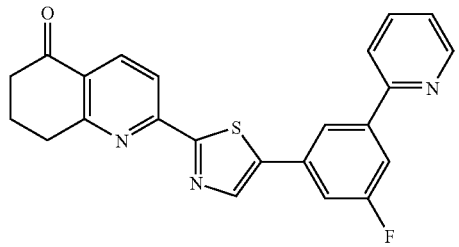

In analogy to the procedure described in Example 26, the title compound is obtained in significant yield.

Example 171

2-[5-(3-Fluoro-5-pyridin-3-yl-phenyl)-thiazol-2-yl]-7,8-dihydro-6H-quinolin-5-one

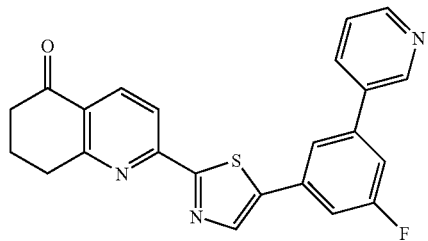

In analogy to the procedure described in Example 26, the title compound is obtained in significant yield.

Example 172

2-Adamantan-1-yl-6,7,8,9,9a,10-hexahydro-5aH-benzo[g]quinolin-5-one

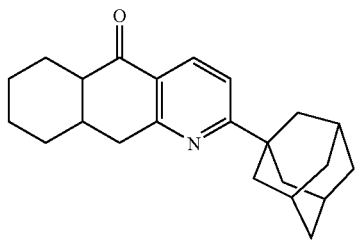

In analogy to the procedure described in Example 13, the title compound is obtained in significant yield.

Example 173

7,7-Dimethyl-2-pyridin-3-ylethynyl-7,8-dihydro-6H-quinolin-5-one

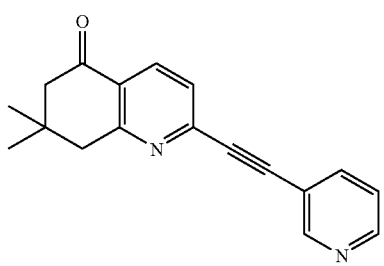

In analogy to the procedure described in Example 83, the title compound is obtained in significant yield.

Example 174

7,7-Dimethyl-2-m-tolylethynyl-7,8-dihydro-6H-quinolin-5-one

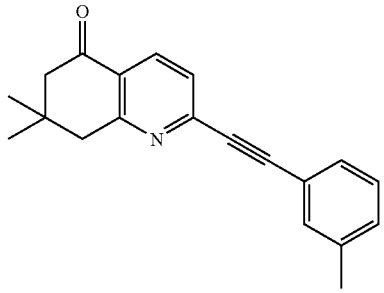

In analogy to the procedure described in Example 83, the title compound is obtained in significant yield.

Example 175

2-(3-Hydroxy-phenylethynyl)-7,7-dimethyl-7,8-dihydro-6H-quinolin-5-one

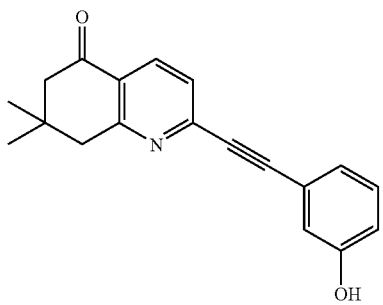

In analogy to the procedure described in Example 83, the title compound is obtained in significant yield.

Example 176

2-(3-Methoxy-phenylethynyl)-7,7-dimethyl-7,8-dihydro-6H-quinolin-5-one

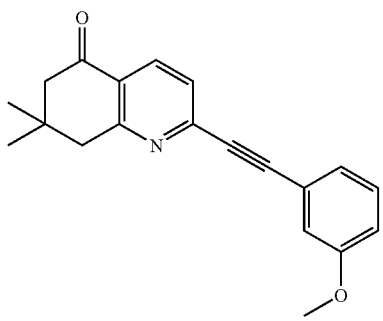

In analogy to the procedure described in Example 83, the title compound is obtained in significant yield.

Example 177

2-(3-Fluoro-phenylethynyl)-7,7-dimethyl-7,8-dihydro-6H-quinolin-5-one

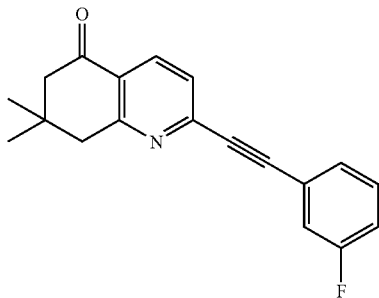

In analogy to the procedure described in Example 83, the title compound is obtained in significant yield.

Example 178

2-(3-Chloro-phenylethynyl)-7,7-dimethyl-7,8-dihydro-6H-quinolin-5-one

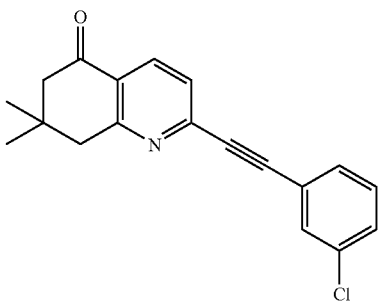

In analogy to the procedure described in Example 83, the title compound is obtained in significant yield.

Example 179

2-(3-Bromo-phenylethynyl)-7,7-dimethyl-7,8-dihydro-6H-quinolin-5-one

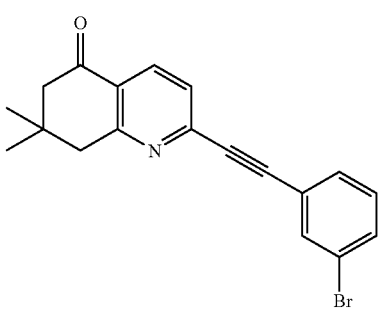

In analogy to the procedure described in Example 83, the title compound is obtained in significant yield.

Example 180

3-(7,7-Dimethyl-5-oxo-5,6,7,8-tetrahydro-quinolin-2-ylethynyl)-benzonitrile

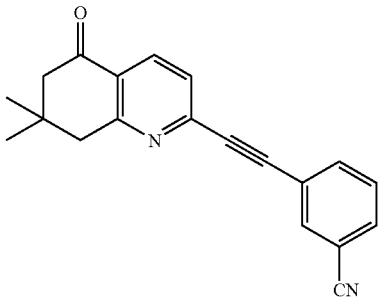

In analogy to the procedure described in Example 83, the title compound is obtained in significant yield.

Example 181

7,7-Dimethyl-2-thiazol-5-ylethynyl-7,8-dihydro-6H-quinolin-5-one

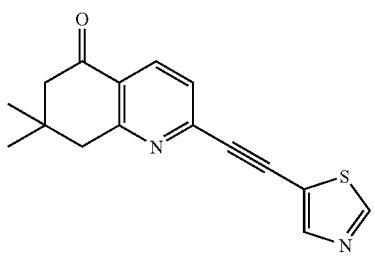

In analogy to the procedure described in Example 83, the title compound is obtained in significant yield.

Example 182

7,7-Dimethyl-2-oxazol-5-ylethynyl-7,8-dihydro-6H-quinolin-5-one

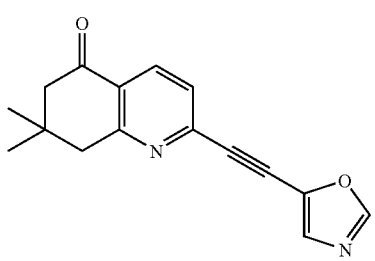

In analogy to the procedure described in Example 83, the title compound is obtained in significant yield.

Example 183

2-(3-Methoxy-4-pyridin-3-yl-phenyl)-7,7-dimethyl-7,8-dihydro-6H-quinolin-5-one

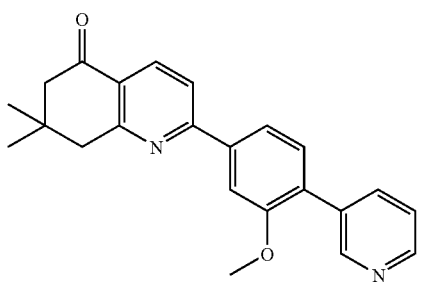

In analogy to the procedure described in Example 26, the title compound is obtained in significant yield.

Example 184

2-(3-Methoxy-4-pyridin-2-yl-phenyl)-7,7-dimethyl-7,8-dihydro-6H-quinolin-5-one

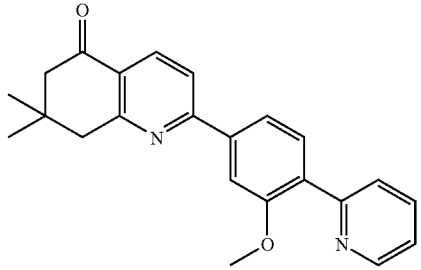

In analogy to the procedure described in Example 26, the title compound is obtained in significant yield.

Example 185

2-[5-(3-Fluoro-5-pyridin-4-yl-phenyl)-thiazol-2-yl]-7,8-dihydro-6H-quinolin-5-one

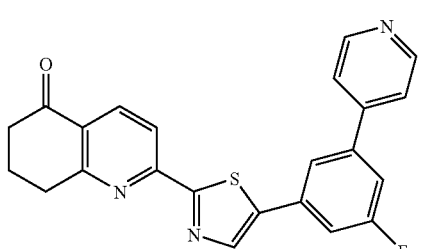

In analogy to the procedure described in Example 26, the title compound is obtained in significant yield.

Example 186

2-[5-(3-Fluoro-5-morpholin-4-yl-phenyl)-thiazol-2-yl]-7,8-dihydro-6H-quinolin-5-one

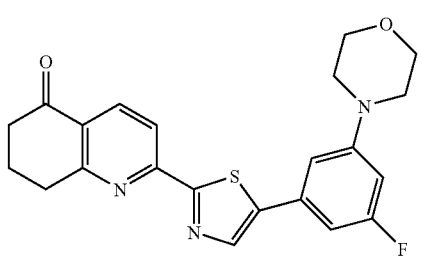

In analogy to the procedure described in Example 26, the title compound is obtained in significant yield.

Example 187

2-[5-(3-Fluoro-5-piperidin-1-yl-phenyl)-thiazol-2-yl]-7,8-dihydro-6H-quinolin-5-one

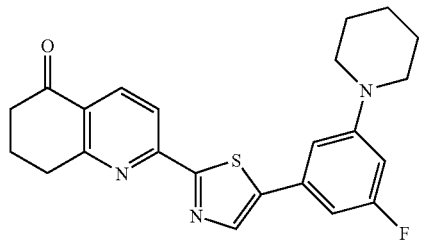

In analogy to the procedure described in Example 26, the title compound is obtained in significant yield.

Example 188

7,7-Dimethyl-2-(5-m-tolyl-thiazol-2-yl)-7,8-dihydro-6H-quinolin-5-one

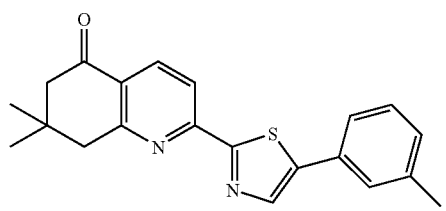

In analogy to the procedure described in Example 26, the title compound is obtained in significant yield.

Example 189

2-[5-(3-Hydroxy-phenyl)-thiazol-2-yl]-7,7-dimethyl-7,8-dihydro-6H-quinolin-5-one

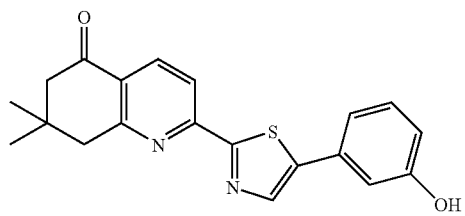

In analogy to the procedure described in Example 26, the title compound is obtained in significant yield.

Example 190

2-[5-(3-Methoxy-phenyl)-thiazol-2-yl]-7,7-dimethyl-7,8-dihydro-6H-quinolin-5-one

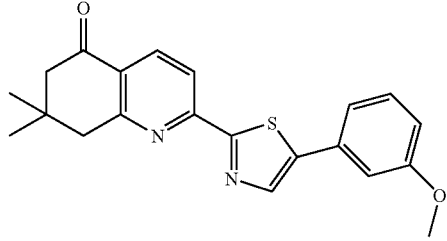

In analogy to the procedure described in Example 26, the title compound is obtained in significant yield.

Example 191

2-[5-(3-Fluoro-phenyl)-thiazol-2-yl]-7,7-dimethyl-7,8-dihydro-6H-quinolin-5-one

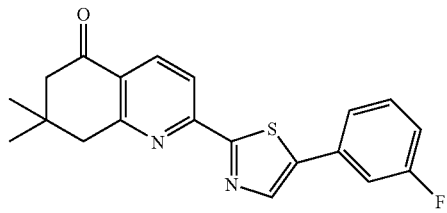

In analogy to the procedure described in Example 26, the title compound is obtained in significant yield.

Example 192

2-[5-(3-Chloro-phenyl)-thiazol-2-yl]-7,7-dimethyl-7,8-dihydro-6H-quinolin-5-one

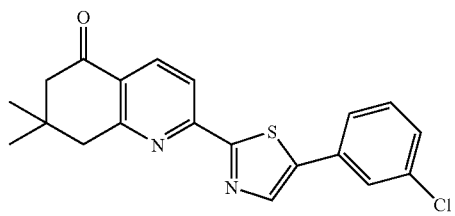

In analogy to the procedure described in Example 26, the title compound is obtained in significant yield.

Example 193

2-[5-(3-Bromo-phenyl)-thiazol-2-yl]-7,7-dimethyl-7,8-dihydro-6H-quinolin-5-one

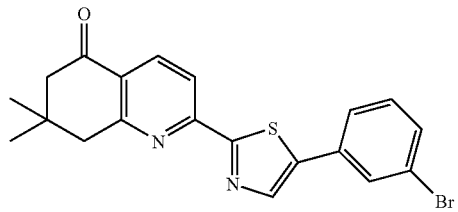

In analogy to the procedure described in Example 26, the title compound is obtained in significant yield.

Example 194

3-[2-(7,7-Dimethyl-5-oxo-5,6,7,8-tetrahydro-quinolin-2-yl)-thiazol-5-yl]-benzonitrile

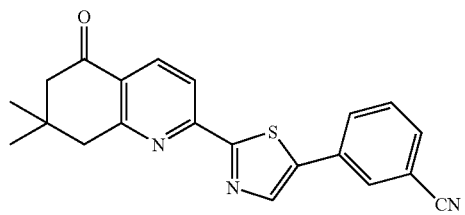

In analogy to the procedure described in Example 26, the title compound is obtained in significant yield.

Example 195

2-[5-(3,5-Dimethoxy-phenyl)-thiazol-2-yl]-7,7-dimethyl-7,8-dihydro-6H-quinolin-5-one

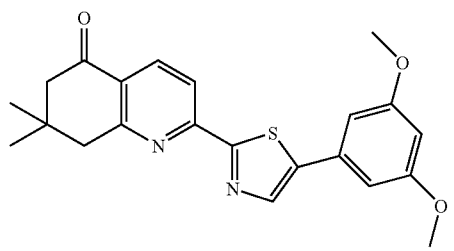

In analogy to the procedure described in Example 26, the title compound is obtained in significant yield.

Example 196

2-[2-(3,5-Dimethoxy-phenyl)-vinyl]-7,7-dimethyl-7,8-dihydro-6H-quinolin-5-one

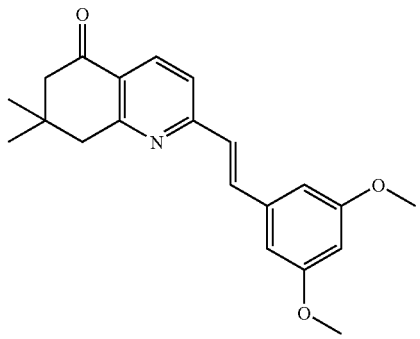

In analogy to the procedure described in Example 13, the title compound is obtained in significant yield.

Example 197

2-[5-(3-Fluoro-5-methyl-phenyl)-thiazol-2-yl]-7,7-dimethyl-7,8-dihydro-6H-quinolin-5-one

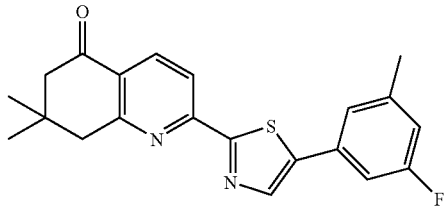

In analogy to the procedure described in Example 26, the title compound is obtained in significant yield.

Example 198

3-[2-(7,7-Dimethyl-5-oxo-5,6,7,8-tetrahydro-quinolin-2-yl)-thiazol-5-yl]-5-fluoro-benzonitrile

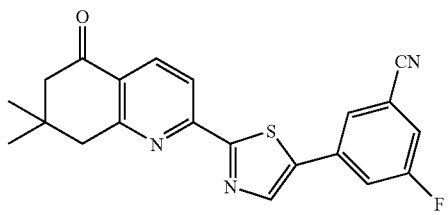

In analogy to the procedure described in Example 26, the title compound is obtained in significant yield.

Example 199

2-[5-(3-Fluoro-phenyl)-thiazol-2-yl]-7,8-dihydro-6H-quinolin-5-one

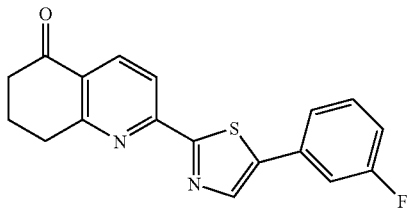

In analogy to the procedure described in Example 26, the title compound is obtained in significant yield.

Example 200

2-[5-(3-Fluoro-5-methoxy-phenyl)-thiazol-2-yl]-7,7-dimethyl-7,8-dihydro-6H-quinolin-5-one

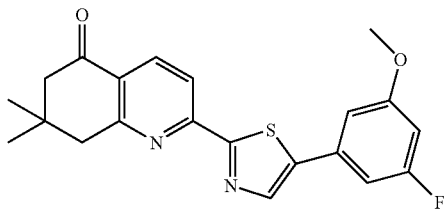

In analogy to the procedure described in Example 26, the title compound is obtained in significant yield.

Example 201

2-[5-(3-Fluoro-5-pyridin-2-yl-phenyl)-thiazol-2-yl]-7,7-dimethyl-7,8-dihydro-6H-quinolin-5-one

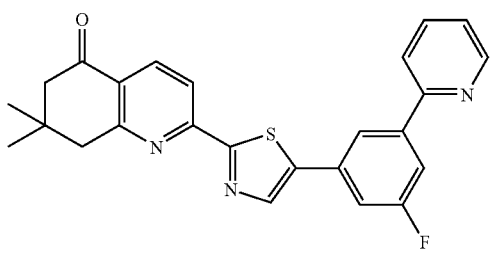

In analogy to the procedure described in Example 26, the title compound is obtained in significant yield.

Example 202

2-[5-(3-Fluoro-5-pyridin-3-yl-phenyl)-thiazol-2-yl]-7,7-dimethyl-7,8-dihydro-6H-quinolin-5-one

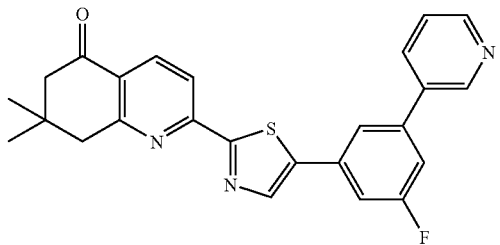

In analogy to the procedure described in Example 26, the title compound is obtained in significant yield.

Example 203

2-[5-(3-Fluoro-5-pyridin-4-yl-phenyl)-thiazol-2-yl]-7,7-dimethyl-7,8-dihydro-6H-quinolin-5-one

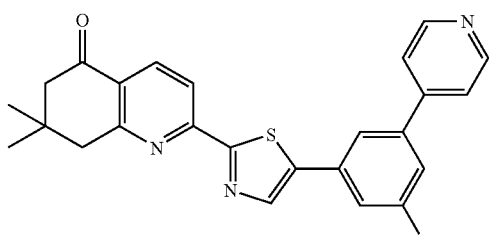

In analogy to the procedure described in Example 26, the title compound is obtained in significant yield.

Example 204

2-[5-(3-Fluoro-5-morpholin-4-yl-phenyl)-thiazol-2-yl]-7,7-dimethyl-7,8-dihydro-6H-quinolin-5-one

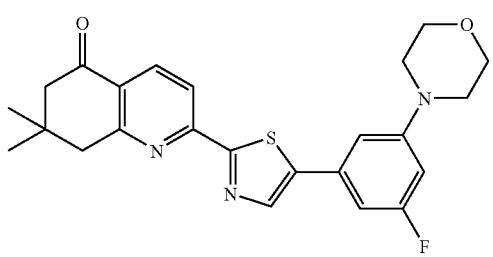

In analogy to the procedure described in Example 26, the title compound is obtained in significant yield.

Example 205

2-[5-(3-Fluoro-5-piperidin-1-yl-phenyl)-thiazol-2-yl]-7,7-dimethyl-7,8-dihydro-6H-quinolin-5-one

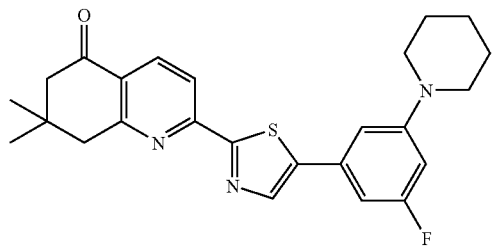

In analogy to the procedure described in Example 26, the title compound is obtained in significant yield.

Example 206

2-(5-m-Tolyl-[1,3,4]oxadiazol-2-yl)-7,8-dihydro-6H-quinolin-5-one

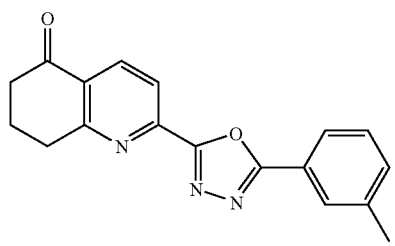

In analogy to the procedure described in Example 26, the title compound is obtained in significant yield.

Example 207

2-(5-m-Tolyl-oxazol-2-yl)-7,8-dihydro-6H-quinolin-5-one

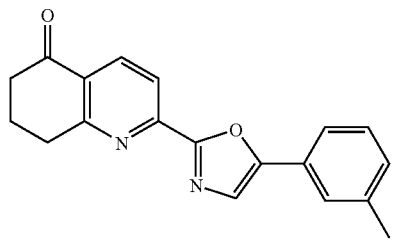

In analogy to the procedure described in Example 26, the title compound is obtained in significant yield.

Example 208

2-(1-m-Tolyl-1H-imidazol-4-yl)-7,8-dihydro-6H-quinolin-5-one

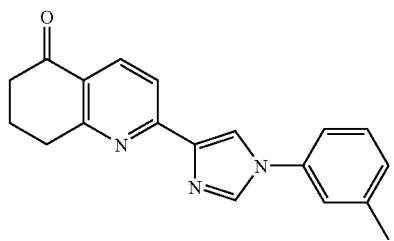

In analogy to the procedure described in Example 26, the title compound is obtained in significant yield.

Example 209

2-(5-m-Tolyl-isoxazol-3-yl)-7,8-dihydro-6H-quinolin-5-one

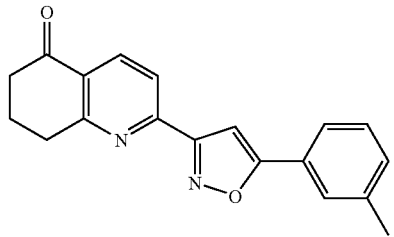

In analogy to the procedure described in Example 26, the title compound is obtained in significant yield.

Example 210

2-[5-(3-Fluoro-phenyl)-oxazol-2-yl]-7,8-dihydro-6H-quinolin-5-one

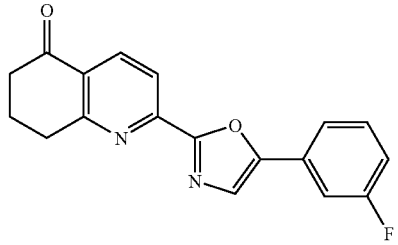

In analogy to the procedure described in Example 26, the title compound is obtained in significant yield.

Example 211

2-[1-(3-Fluoro-phenyl)-1H-imidazol-4-yl]-7,8-dihydro-6H-quinolin-5-one

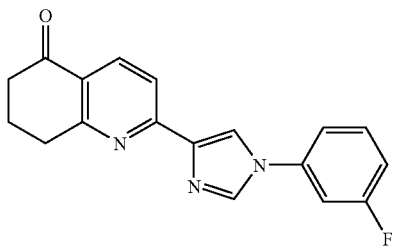

In analogy to the procedure described in Example 26, the title compound is obtained in significant yield.

Example 212

2-[5-(3-Fluoro-phenyl)-isoxazol-3-yl]-7,8-dihydro-6H-quinolin-5-one

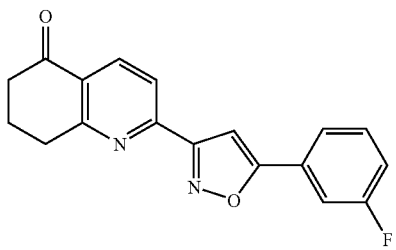

In analogy to the procedure described in Example 26, the title compound is obtained in significant yield.

Example 213

3-[2-(5-Oxo-5,6,7,8-tetrahydro-quinolin-2-yl)-oxazol-5-yl]-benzonitrile

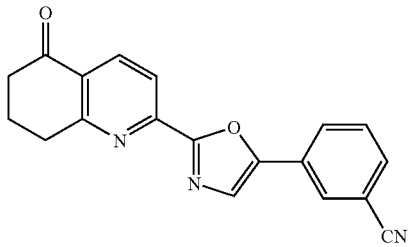

In analogy to the procedure described in Example 26, the title compound is obtained in significant yield.

Example 214

3-[1-(5-Oxo-5,6,7,8-tetrahydro-quinolin-2-yl)-1H-imidazol-4-yl]-benzonitrile

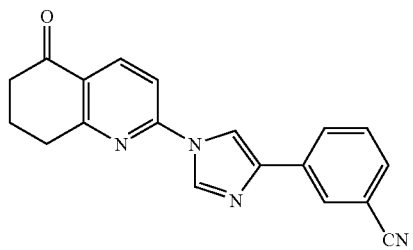

In analogy to the procedure described in Example 7 or 12, the title compound is obtained in significant yield.

Example 215

3-[3-(5-Oxo-5,6,7,8-tetrahydro-quinolin-2-yl)-isoxazol-5-yl]-benzonitrile

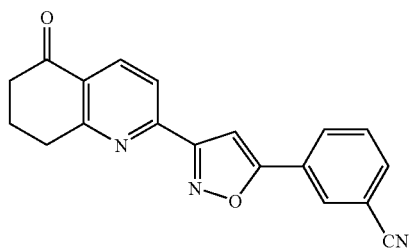

In analogy to the procedure described in Example 26, the title compound is obtained in significant yield.

Example 216

3-[2-(7,7-Dimethyl-5-oxo-5,6,7,8-tetrahydro-quinolin-2-yl)-oxazol-5-yl]-benzonitrile

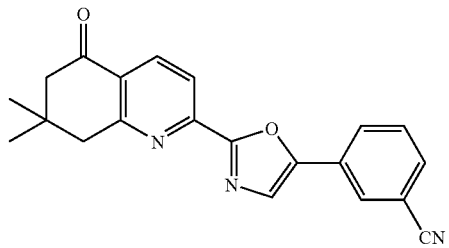

In analogy to the procedure described in Example 26, the title compound is obtained in significant yield.

Example 217

3-[1-(7,7-Dimethyl-5-oxo-5,6,7,8-tetrahydro-quinolin-2-yl)-1H-imidazol-4-yl]-benzonitrile

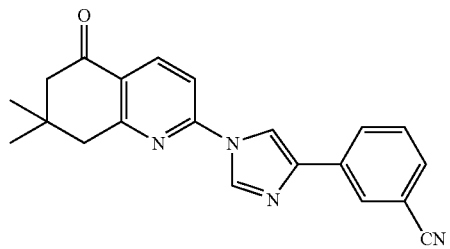

In analogy to the procedure described in Example 86 the title compound is obtained in significant yield.

Example 218

3-[3-(7,7-Dimethyl-5-oxo-5,6,7,8-tetrahydro-quinolin-2-yl)-isoxazol-5-yl]-benzonitrile

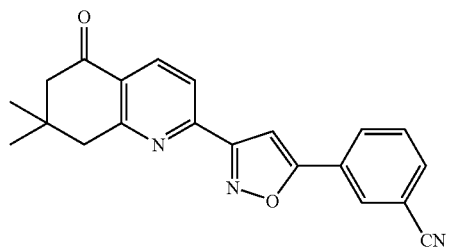

In analogy to the procedure described in Example 26, the title compound is obtained in significant yield.

Example 219

3-[2-(7,7-Dimethyl-5-oxo-5,6,7,8-tetrahydro-quinolin-2-yl)-oxazol-5-yl]-5-fluoro-benzonitrile

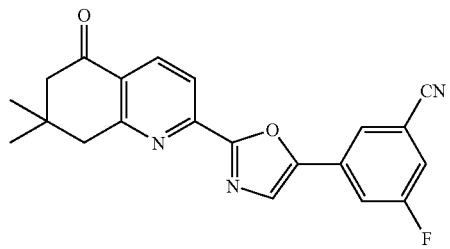

In analogy to the procedure described in Example 26, the title compound is obtained in significant yield.

Example 220

3-[1-(7,7-Dimethyl-5-oxo-5,6,7,8-tetrahydro-quinolin-2-yl)-1H-imidazol-4-yl]-5-fluoro-benzonitrile

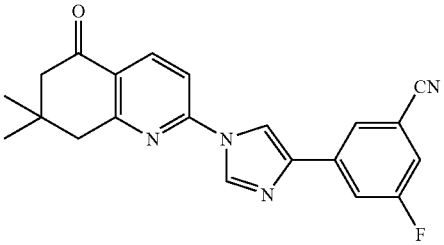

In analogy to the procedure described in Example 86 the title compound is obtained in significant yield.

Example 221

3-[3-(7,7-Dimethyl-5-oxo-5,6,7,8-tetrahydro-quinolin-2-yl)-isoxazol-5-yl]-5-fluoro-benzonitrile

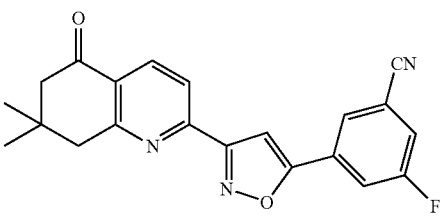

In analogy to the procedure described in Example 26, the title compound is obtained in significant yield.

Example 222

7,7-Dimethyl-2-(5-pyridin-3-yl-thiazol-2-yl)-7,8-dihydro-6H-quinolin-5-one

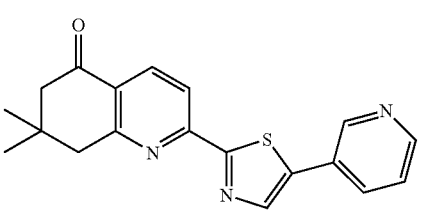

In analogy to the procedure described in Example 26, the title compound is obtained in significant yield.

Example 223

2-(5-Pyridin-3-yl-thiazol-2-yl)-7,8-dihydro-6H-quinolin-5-one

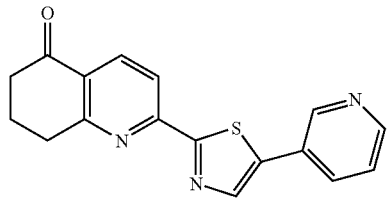

In analogy to the procedure described in Example 26, the title compound is obtained in significant yield.

Example 224

2-(3-Methoxy-4-pyridin-2-yl-phenylamino)-7,7-dimethyl-7,8-dihydro-6H-quinolin-5-one

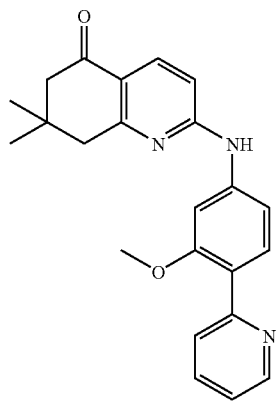

In analogy to the procedure described in Example 86, the title compound is obtained in significant yield.

Example 225

2-(3-Methoxy-4-pyridin-3-yl-phenylamino)-7,7-dimethyl-7,8-dihydro-6H-quinolin-5-one

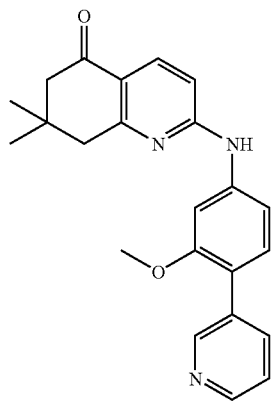

In analogy to the procedure described in Example 86, the title compound is obtained in significant yield.

Example 226

2-(3-Fluoro-4-pyridin-2-yl-phenylamino)-7,7-dimethyl-7,8-dihydro-6H-quinolin-5-one

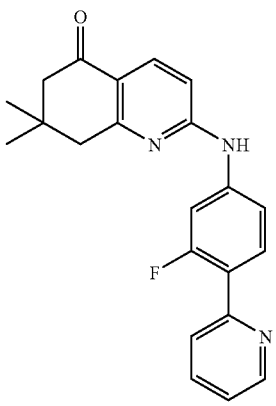

In analogy to the procedure described in Example 86, the title compound is obtained in significant yield.

Example 227

7,7-Dimethyl-2-(pyridin-2-ylamino)-7,8-dihydro-6H-quinolin-5-one

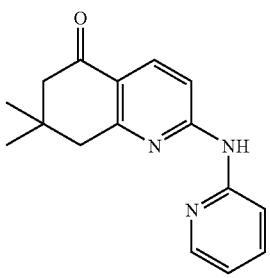

In analogy to the procedure described in Example 86, the title compound is obtained in significant yield.

Example 228

2-(3-Methoxy-phenylamino)-7,7-dimethyl-7,8-dihydro-6H-quinolin-5-one

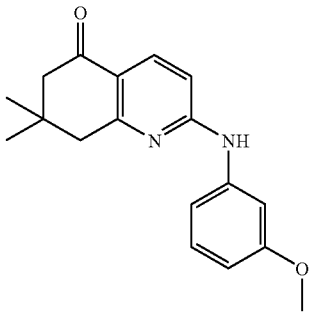

In analogy to the procedure described in Example 86, the title compound is obtained in significant yield.

Example 229

2-(Indan-2-ylamino)-7,7-dimethyl-5-oxo-5,6,7,8-tetrahydro-quinoline-3-carbonitrile

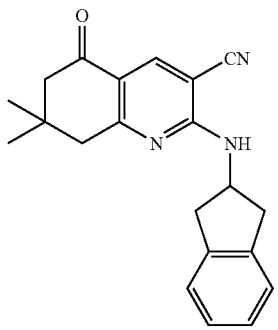

In analogy to the procedure described in Example 7 or 12, the title compound is obtained in significant yield.

Example 230

7,7-Dimethyl-5-oxo-2-phenylamino-5,6,7,8-tetrahydro-quinoline-3-carbonitrile

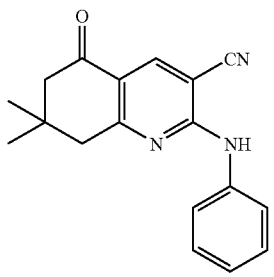

In analogy to the procedure described in Example 86, the title compound is obtained in significant yield.

Example 231

2-(4-Methoxy-phenylamino)-7,7-dimethyl-5-oxo-5,6,7,8-tetrahydro-quinoline-3-carbonitrile

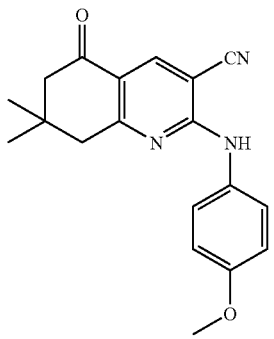

In analogy to the procedure described in Example 86, the title compound is obtained in significant yield.

Example 232

2-(4-Methoxy-phenylamino)-7,7-dimethyl-3-nitro-7,8-dihydro-6H-quinolin-5-one

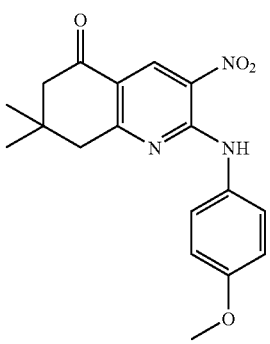

In analogy to the procedure described in Example 86, the title compound is obtained in significant yield.

Example 233

2-(1,3-Dihydro-isoindol-2-yl)-7,7-dimethyl-5-oxo-5,6,7,8-tetrahydro-quinoline-3-carbonitrile

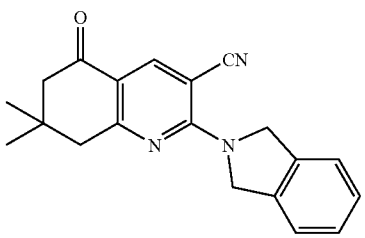

In analogy to the procedure described in Example 7 or 12, the title compound is obtained in significant yield.

Example 234

2-(3,4-Dihydro-1H-isoquinolin-2-yl)-7,7-dimethyl-5-oxo-5,6,7,8-tetrahydro-quinoline-3-carbonitrile

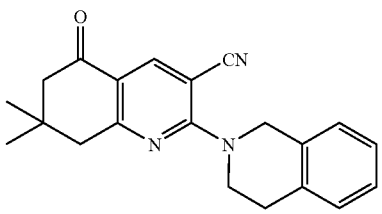

In analogy to the procedure described in Example 7 or 12, the title compound is obtained in significant yield.

Example 235

2-(Adamantan-1-ylamino)-7,7-dimethyl-5-oxo-5,6,7,8-tetrahydro-quinoline-3-carbonitrile

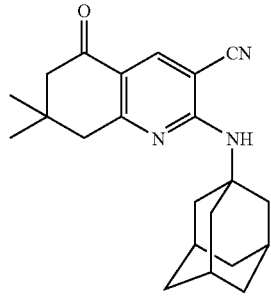

In analogy to the procedure described in Example 7 or 12, the title compound is obtained in significant yield.

Example 236

7,7-Dimethyl-3-morpholin-4-yl-2-(4-phenyl-piperidin-1-yl)-7,8-dihydro-6H-quinolin-5-one

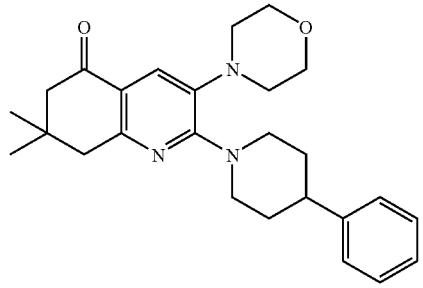

In analogy to the procedure described in Example 7 or 12, the title compound is obtained in significant yield.

Example 237

2-(3-Fluoro-4-pyridin-3-yl-phenylamino)-7,7-dimethyl-7,8-dihydro-6H-quinolin-5-one

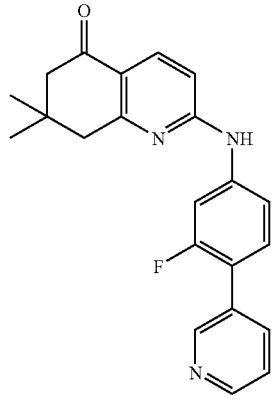

In analogy to the procedure described in Example 86, the title compound is obtained in significant yield.

Example 238

2-(3-Methoxy-4-pyridin-2-yl-phenylamino)-7,8-dihydro-6H-quinolin-5-one

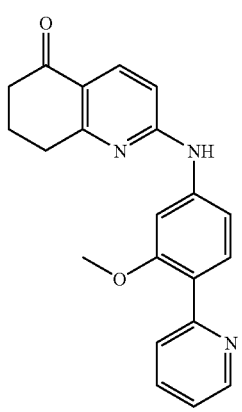

In analogy to the procedure described in Example 86, the title compound is obtained in significant yield.

Example 239

2-(3-Methoxy-4-pyridin-3-yl-phenylamino)-7,8-dihydro-6H-quinolin-5-one

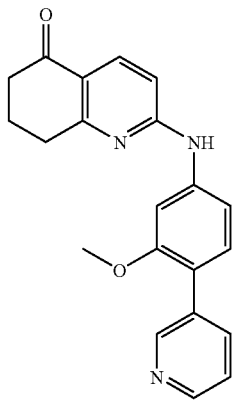

In analogy to the procedure described in Example 86, the title compound is obtained in significant yield.

Example 240

2-(3-Fluoro-4-pyridin-2-yl-phenylamino)-7,8-dihydro-6H-quinolin-5-one

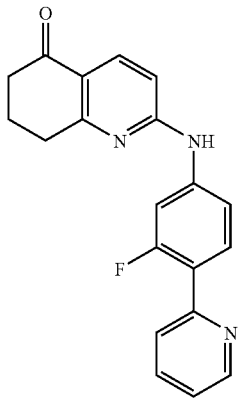

In analogy to the procedure described in Example 86, the title compound is obtained in significant yield.

Example 241

2-(3-Fluoro-4-pyridin-3-yl-phenylamino)-7,8-dihydro-6H-quinolin-5-one

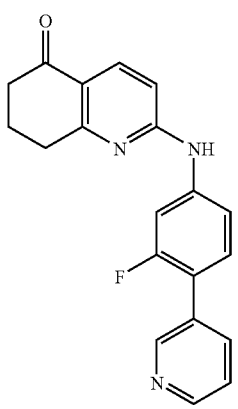

In analogy to the procedure described in Example 86, the title compound is obtained in significant yield.

Example 242

7,7-Dimethyl-2-(pyridin-3-ylamino)-7,8-dihydro-6H-quinolin-5-one

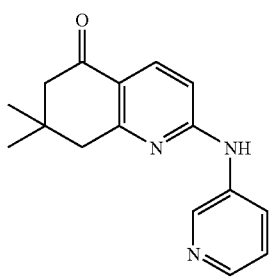

In analogy to the procedure described in Example 86, the title compound is obtained in significant yield.

Example 243

7,7-Dimethyl-2-(pyridin-4-ylamino)-7,8-dihydro-6H-quinolin-5-one

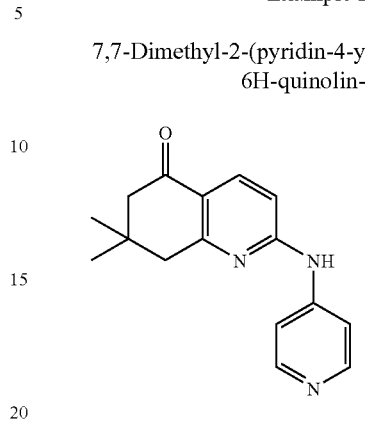

In analogy to the procedure described in Example 86, the title compound is obtained in significant yield.

Example 244

5-Oxo-2-(5-phenyl-thiazol-2-yl)-5,6,7,8-tetrahydro-quinoline-3-carbonitrile

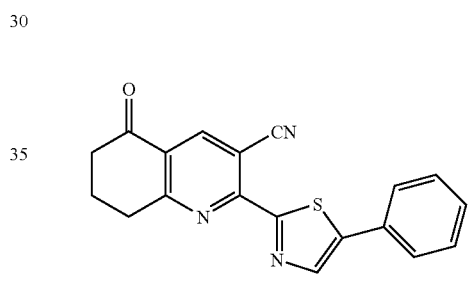

In analogy to the procedure described in Example 26, the title compound is obtained in significant yield.

Example 245

2-(3-Methoxy-4-pyridin-2-yl-phenylamino)-7,7-dimethyl-5-oxo-5,6,7,8-tetrahydro-quinoline-3-carbonitrile

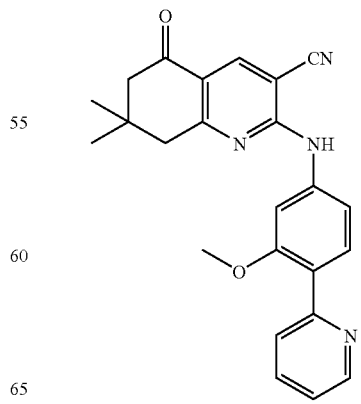

In analogy to the procedure described in Example 86, the title compound is obtained in significant yield.

Example 246

2-(3-Methoxy-4-pyridin-3-yl-phenylamino)-7,7-dimethyl-5-oxo-5,6,7,8-tetrahydro-quinoline-3-carbonitrile

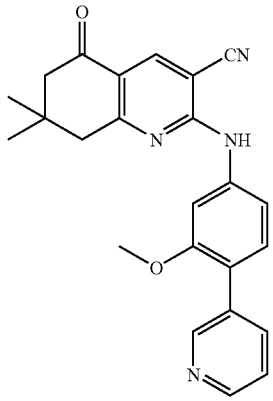

In analogy to the procedure described in Example 86, the title compound is obtained in significant yield.

Example 247

7,7-Dimethyl-5-oxo-2-(pyridin-4-ylamino)-5,6,7,8-tetrahydro-quinoline-3-carbonitrile

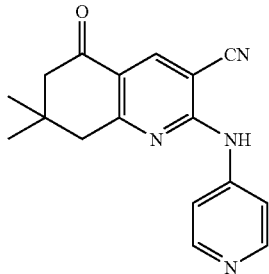

In analogy to the procedure described in Example 86, the title compound is obtained in significant yield.

Example 248

7,7-Dimethyl-3-nitro-2-(pyridin-4-ylamino)-7,8-dihydro-6H-quinolin-5-one

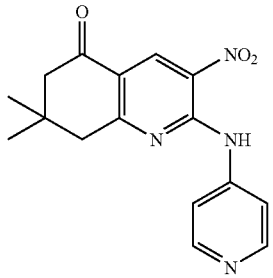

In analogy to the procedure described in Example 86, the title compound is obtained in significant yield.

Example 249

2-(3,5-Dimethoxy-phenylamino)-7,7-dimethyl-7,8-dihydro-6H-quinolin-5-one

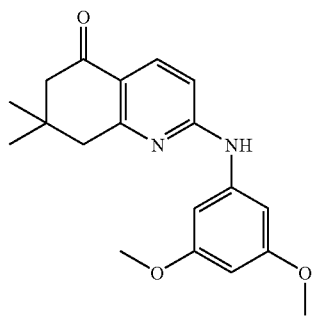

In analogy to the procedure described in Example 86, the title compound is obtained in significant yield.

Example 250

2-Benzylsulfanyl-7,7-dimethyl-3-nitro-7,8-dihydro-6H-quinolin-5-one

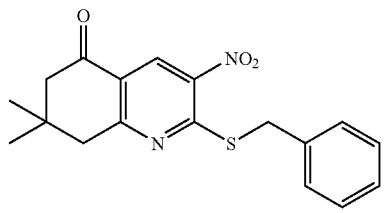

The title compound is obtained in significant yield according to the procedures shown in Scheme 1.

Example 251

2-Benzylsulfanyl-3-chloro-7,7-dimethyl-7,8-dihydro-6H-quinolin-5-one

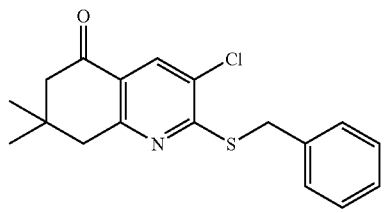

Example 252

7,7-Dimethyl-3-nitro-2-piperidin-1-yl-7,8-dihydro-6H-quinolin-5-one

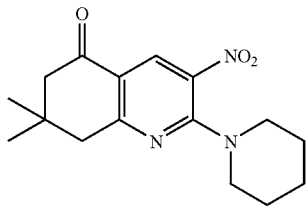

In analogy to the procedure described in Example 94 the title compound is obtained in significant yield.

Example 253

3-Chloro-7,7-dimethyl-2-piperidin-1-yl-7,8-dihydro-6H-quinolin-5-one

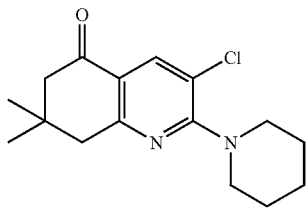

In analogy to the procedure described in Example 94, the title compound is obtained in significant yield.

Example 254

2-Cyclopentylamino-7,7-dimethyl-3-nitro-7,8-dihydro-6H-quinolin-5-one

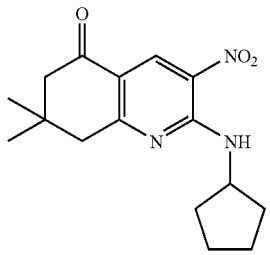

In analogy to the procedure described in Example 94, the title compound is obtained in significant yield.

Example 255

3-Chloro-2-cyclopentylamino-7,7-dimethyl-7,8-dihydro-6H-quinolin-5-one

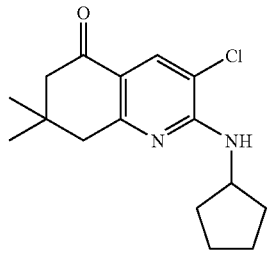

In analogy to the procedure described in Example 94, the title compound is obtained in significant yield.

Example 256

3-Chloro-2-[4-(4-methoxy-phenyl)-piperazin-1-yl]-7,7-dimethyl-7,8-dihydro-6H-quinolin-5-one

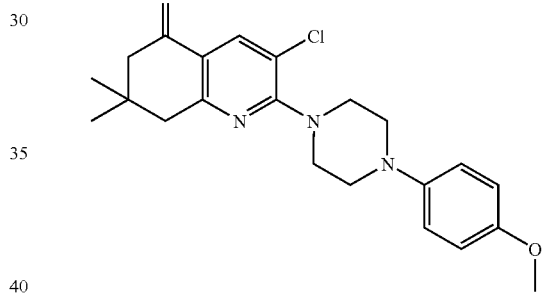

In analogy to the procedure described in Example 94, the title compound is obtained in significant yield.

Example 257

2-[4-(4-Methoxy-phenyl)-piperazin-1-yl]-7,7-dimethyl-3-nitro-7,8-dihydro-6H-quinolin-5-one

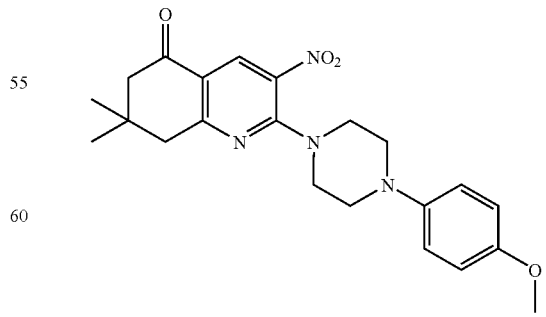

In analogy to the procedure described in Example 94, the title compound is obtained in significant yield.

Example 258

7,7-Dimethyl-5-oxo-2-(3,4,5,6-tetrahydro-2H-[4,4]bipyridinyl-1-yl)-5,6,7,8-tetrahydro-quinoline-3-carbonitrile

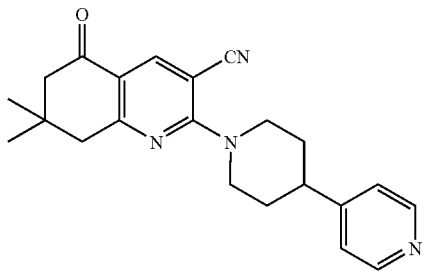

In analogy to the procedure described in Example 94, the title compound is obtained in significant yield.

Example 259

2-[4-(4-Methoxy-phenyl)-piperidin-1-yl]-7,7-dimethyl-5-oxo-5,6,7,8-tetrahydro-quinoline-3-carbonitrile

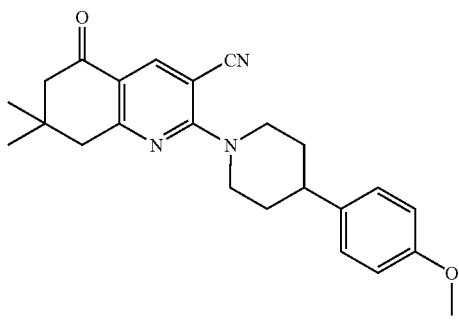

In analogy to the procedure described in Example 94, the title compound is obtained in significant yield.

Example 260

2-[1-(4-Methoxy-phenyl)-piperidin-4-yl]-7,7-dimethyl-5-oxo-5,6,7,8-tetrahydro-quinoline-3-carbonitrile

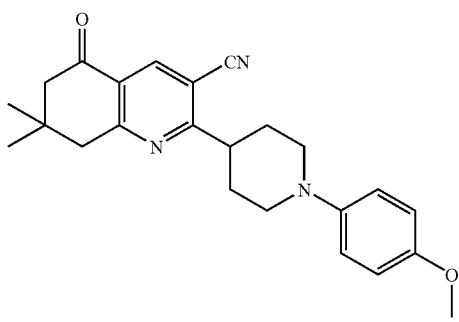

In analogy to the procedure described in Example 13, the title compounds is obtained in significant yield.

Example 261

7,7-Dimethyl-5-oxo-2-(6,7,8,9-tetrahydro-5H-benzocyclohepten-7-ylamino)-5,6,7,8-tetrahydro-quinoline-3-carbonitrile

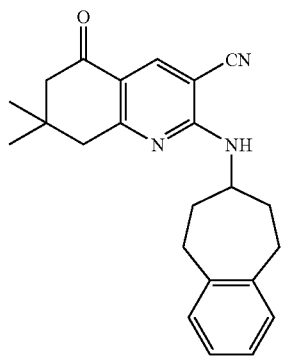

In analogy to the procedure described in Example 94, the title compound is obtained in significant yield.

Example 262

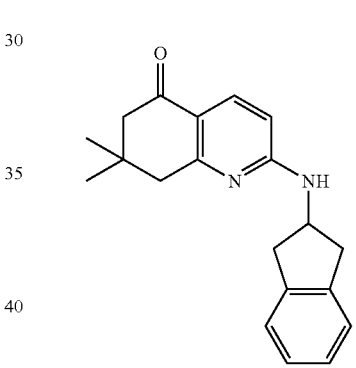

In analogy to the procedure described in Example 94, the title compound is obtained in significant yield.

Example 263

2-(4-Methoxy-cyclohexylamino)-7,7-dimethyl-3-nitro-7,8-dihydro-6H-quinolin-5-one

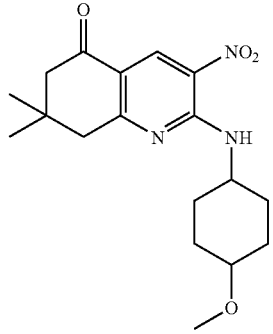

In analogy to the procedure described in Example 94, the title compound is obtained in significant yield.

Example 264

2-(4-Methoxy-cyclohexylamino)-7,7-dimethyl-7,8-dihydro-6H-quinolin-5-one

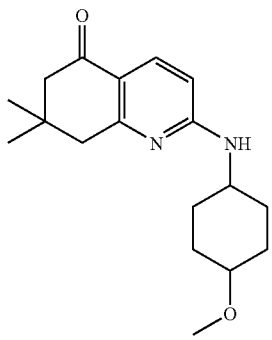

In analogy to the procedure described in Example 94, the title compound is obtained in significant yield.

Example 265

2-(4-Methoxy-cyclohexylamino)-7,7-dimethyl-5-oxo-5,6,7,8-tetrahydro-quinoline-3-carbonitrile

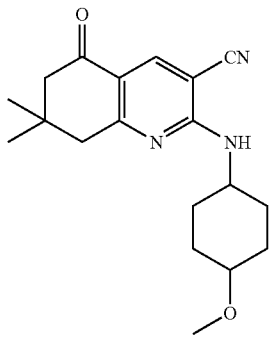

In analogy to the procedure described in Example 94, the title compound is obtained in significant yield.

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers may be separated from each other by selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric form of appropriate starting materials, provided that the reaction occurs stereoselectively. Stereoisomeric forms of Formula IA are obviously intended to be included within the scope of this invention.

Addition Salts

For therapeutic use, salts of the compounds of Formula IA are those wherein the counterion is pharmaceutically acceptable. However, salts of acids and bases which are non-pharmaceutically acceptable may also find use, for example, in the preparation and purification of pharmaceutically acceptable compounds. All salts whether pharmaceutically acceptable or not are included within the ambit of the present invention. The pharmaceutically acceptable salts as mentioned above are meant to comprise the therapeutically active non-toxic salt forms which the compounds of Formula IA are able to form. The latter can conveniently be obtained by treating the base form with such appropriate acids as inorganic acids, e.g. hydrohalic acids such as hydrochloric, hydrobromic and the like; sulfuric acid; nitric acid; phosphoric acid and the like; or organic acids such as acetic, propanoic, hydroxyacetic, 2-hydroxypropanoic, oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely, the salt form can be converted by treatment with alkali into the free base form.

Pharmaceutical Compositions

The active ingredients of the invention, together with one or more conventional adjuvants, carriers, or diluents, may be placed into the form of pharmaceutical compositions and unit dosages thereof, and in such form may be employed as solids, such as coated or uncoated tablets or filled capsules, or liquids, such as solutions, suspensions, emulsions, elixirs, or capsules filled with the same, all for oral use; in the form of suppositories or capsules for rectal administration or in the form of sterile injectable solutions for parenteral (including intravenous or subcutaneous) use. Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing one (1) to one hundred (100) milligrams of active ingredient or, more broadly, zero point five (0.5) to five hundred (500) milligrams per tablet, are accordingly suitable representative unit dosage forms.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18$^{th}$ Edition.

Method of Treating

Due to their high degree of activity and their low toxicity, together presenting a most favorable therapeutic index, the active principles of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous and subcutaneous) or in some cases even topical route, in an effective amount. Suitable dosage ranges are 1-1000 milligrams daily, preferably 10-500 milligrams daily, and especially 50-500 milligrams daily, depending as usual upon the exact mode of administration, form in which administered, the indication toward which the administration is directed, the subject involved and the body weight of the subject involved, and the preference and experience of the physician or veterinarian in charge.

The term "therapeutically effective" applied to dose or amount refers to that quantity of a compound or pharmaceutical composition that is sufficient to result in a desired activity upon administration to a living animal body in need thereof.

The active agents of the present invention may be administered orally, topically, parenterally, or mucosally (e.g., buccally, by inhalation, or rectally) in dosage unit formulations containing conventional non-toxic pharmaceutically acceptable carriers. It is usually desirable to use the oral route. The active agents may be administered orally in the form of a capsule, a tablet, or the like (see Remington's Pharmaceutical Sciences, Mack 5 Publishing Co., Easton, Pa.). The orally administered medicaments may be administered in the form of a time-controlled release vehicle, including diffusion-controlled systems, osmotic devices, dissolution-controlled matrices, and erodible/degradable matrices.

For oral administration in the form of a tablet or capsule, the active drug component can be combined with a non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like. For oral administration in liquid form, the drug components can be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) can also be added to stabilize the dosage forms.

The tablets can be coated by methods well known in the art. The compositions of the invention can be also introduced in microspheres or microcapsules, e.g., fabricated from polyglycolic acid/lactic acid (PGLA). Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known.

Drugs of the invention may also be delivered by the use of monoclonal antibodies as individual carriers to which the compound molecules are coupled. Active drugs may also be coupled with soluble polymers as targetable drug carriers. Such polymers can include polyvinyl-pyrrolidone, pyran copolymer, polyhydroxy-propyl methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

For administration by inhalation, the therapeutics according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The formulations of the invention can be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

Compositions of the present invention can also be formulated for rectal administration, e.g., as suppositories or retention enemas (e.g., containing conventional suppository bases such as cocoa butter or other glycerides).

The compositions may, if desired, be presented in a pack or dispenser device which may contain one or more unit dosage forms containing the active ingredient and/or may contain different dosage levels to facilitate dosage titration. The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

Examples of Representative Pharmaceutical Compositions

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions follow.

(a) Tablets suitable for oral administration which contain the active ingredient may be prepared by conventional tabletting techniques.

(b) For suppositories, any usual suppository base may be employed for incorporation thereinto by usual procedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

FORMULATION EXAMPLES

The following examples are again given by way of illustration only and are not to be construed as limiting.

Example 1

Tablet Formulation

A suitable formulation for a tablet containing 10 milligrams of active ingredient is as follows:

|  | mg |
|---|---|
| Active Ingredient | 10 |
| Lactose | 61 |
| Microcrystalline Cellulose | 25 |
| Talcum | 2 |
| Magnesium stearate | 1 |
| Colloidal silicon dioxide | 1 |

Example 2

Tablet Formulation

Another suitable formulation for a tablet containing 100 mg is as follows:

|  | mg |
|---|---|
| Active Ingredient | 100 |
| Polyvinylpyrrolidone, crosslinked | 10 |
| Potato starch | 20 |
| Polyvinylpyrrolidone | 19 |
| Magnesium stearate | 1 |
| Microcrystalline Cellulose | 50 |
| Film coated and colored. | |
| The film coating material consists of: | |
| Hypromellose | 10 |
| Microcryst. Cellulose | 5 |
| Talcum | 5 |
| Polyethylene glycol | 2 |
| Color pigments | 5 |

Example 3

Capsule Formulation

A suitable formulation for a capsule containing 50 milligrams of active ingredient is as follows:

|  | mg |
|---|---|
| Active Ingredient | 50 |
| Corn starch | 26 |
| Dibasic calcium phosphate | 50 |
| Talcum | 2 |
| Colloidal silicon dioxide | 2 | filled in a gelatin capsule.

Example 4

Solution for Injection

A suitable formulation for an injectable solution is as follows:

| Active Ingredient | mg | 10 |
|---|---|---|
| Sodium chloride | mg | q.s. |
| Water for Injection | mL | add 1.0 |

Example 5

Liquid Oral Formulation

A suitable formulation for 1 liter of a an oral solution containing 2 milligrams of active ingredient in one milliliter of the mixture is as follows:

|  | mg |
| --- | --- |
| Active Ingredient | 2 |
| Saccharose | 250 |
| Glucose | 300 |
| Sorbitol | 150 |
| Orange flavor | 10 |
| Colorant | q.s. |
| Purified water | add 1000 mL |

Example 6

Liquid Oral Formulation

Another suitable formulation for 1 liter of a liquid mixture containing 20 milligrams of active ingredient in one milliliter of the mixture is as follows:

|  | G |
| --- | --- |
| Active Ingredient | 20.00 |
| Tragacanth | 7.00 |
| Glycerol | 50.00 |
| Saccharose | 400.00 |
| Methylparaben | 0.50 |
| Propylparaben | 0.05 |
| Black currant-flavor | 10.00 |
| Soluble Red color | 0.02 |
| Purified water | add 1000 mL |

Example 7

Liquid Oral Formulation

Another suitable formulation for 1 liter of a liquid mixture containing 2 milligrams of active ingredient in one milliliter of the mixture is as follows:

|  | G |
| --- | --- |
| Active Ingredient | 2 |
| Saccharose | 400 |
| Bitter orange peel tincture | 20 |
| Sweet orange peel tincture | 15 |
| Purified water | add 1000 mL |

Example 8

Aerosol Formulation 180 g aerosol solution contain:

|  | G |
| --- | --- |
| Active Ingredient | 10 |
| Oleic acid | 5 |
| Ethanol | 81 |
| Purified Water | 9 |
| Tetrafluoroethane | 75 |

15 ml of the solution are filled into aluminum aerosol cans, capped with a dosing valve, purged with 3.0 bar.

Example 9

TDS Formulation 100 g solution contain:

|  | G |
| --- | --- |
| Active Ingredient | 10.0 |
| Ethanol | 57.5 |
| Propyleneglycol | 7.5 |
| Dimethylsulfoxide | 5.0 |
| Hydroxyethylcellulose | 0.4 |
| Purified water | 19.6 |

1.8 ml of the solution are placed on a fleece covered by an adhesive backing foil. The system is closed by a protective liner which will be removed before use.

Example 10

Nanoparticle Formulation 10 g of polybutylcyanoacrylate nanoparticles contain:

|  | G |
| --- | --- |
| Active Ingredient | 1.00 |
| Poloxamer | 0.10 |
| Butylcyanoacrylate | 8.75 |
| Mannitol | 0.10 |
| Sodium chloride | 0.05 |

Polybutylcyanoacrylate nanoparticles are prepared by emulsion polymerization in a water/0.1 N HCl/ethanol mixture as polymerizsation medium. The nanoparticles in the suspension are finally lyophilized under vacuum.

Pharmacology—Summary

The active principles of the present invention, and pharmaceutical compositions thereof and method of treating therewith, are characterized by unique and advantageous properties, rendering the "subject matter as a whole", as claimed herein, unobvious. The compounds and pharmaceutical compositions thereof exhibit, in standard accepted reliable test procedures, the following valuable properties and characteristics:

Methods

Binding Assays for the Characterization of mGluR5 Antagonist Properties

[$^3$H]MPEP (2-methyl-6-(phenylethynyl)pyridine) Binding to Transmembrane Allosteric Modulatory Sites of mGluR5 Receptors in Cortical Membranes Preparation of Rat Cortical Membranes:

Male Sprague-Dawley rats (200-250 g) are decapitated and their brains are removed rapidly. The cortex is dissected and homogenized in 20 volumes of ice-cold 0.32 M sucrose using a glass-Teflon homogenizer. The homogenate is centrifuged at 1000×g for 10 min. The pellet is discarded and the supernatant centrifuged at 20,000×g for 20 min. The resulting pellet is re-suspended in 20 volumes of distilled water and centrifuged for 20 min at 8000×g. Then the supernatant and the buffy coat are centrifuged at 48,000×g for 20 min in the presence of 50 mM Tris-HCl, pH 8.0. The pellet is then re-suspended and centrifuged two to three more times at 48,000×g for 20 min in the presence of 50 mM Tris-HCl, pH 8.0. All centrifugation steps are carried out at 4° C. After resuspension in 5 volumes of 50 mM Tris-HCl, pH 8.0 the membrane suspension is frozen rapidly at −80° C.

On the day of assay the membranes are thawed and washed four times by resuspension in 50 mM Tris-HCl, pH 8.0 and centrifugation at 48,000×g for 20 min. and finally re-suspended in 50 mM Tris-HCl, pH 7.4. The amount of protein in the final membrane preparation (250-500 μg/ml) is determined according to the method of Lowry (Lowry O. H. et al., 1951. J. Biol. Chem. 193, 256-275).

[$^3$H]MPEP Assay

Incubations are started by adding ($^3$H)-MPEP (50.2 Ci/mmol, 5 nM, Tocris) to vials with 125-250 μg protein (total volume 0.5 ml) and various concentrations of the agents. The incubations are continued at room temperature for 60 min (equilibrium was achieved under the conditions used). Non-specific binding is defined by the addition of unlabeled MPEP (10 μM). Incubations are terminated using a Millipore filter system. The samples are rinsed twice with 4 ml of ice cold assay buffer over glass fibre filters (Schleicher & Schuell) under a constant vacuum. Following separation and rinse, the filters are placed into scintillation liquid (5 ml Ultima Gold) and radioactivity retained on the filters is determined with a conventional liquid scintillation counter (Hewlett Packard, Liquid Scintillation Analyser).

Characterization

Specific binding is extremely high i.e. normally >85% and essentially independent of buffer (Tris or HEPES oth 50 mM) and pH (6.8-8.9). There is a clear saturable protein dependence and the chosen protein concentration used for subsequent assays (250-500 μg/ml) is within the linear portion of this dependence. Cold MPEP displaces hot ligand with an $IC_{50}$ of 18.8±4.1 nM. The Kd of ($^3$H)-MPEP of 13.6 nM is determined by Scatchard analysis and used according to the Cheng Prussoff relationship to calculate the affinity of displacers as Kd values ($IC_{50}$ of cold MPEP equates to a Ki of 13.7 nM). $B_{max}$ was 0.56 pm/mg protein. Compounds of the present invention exhibit specific affinity for transmembrane modulatory sites of mGLuR5 receptors in cortical/cerebellar membrane preparations.

Function Assay of mGluR1 Receptors in Cerebellar Granule Cells—Radioactive Assay for Changes in IP3 Levels Preparation of Cerebellar Granule Cells Cerebellar cortici are obtained from P8 postnatal Sprague Dawley rats, mechanically disrupted into small pieces with forceps and then transferred to $Ca^{2+}$ and $Mg^{2+}$ free Hank's buffered salt solution (HBSS-CMF) on ice. After three washes in HBSS-CMF, the tissue pieces are incubated 37° C. for 8 minutes in the presence of 0.25% trypsin/0.05% DNase. The enzymatic reaction is stopped with 0.016% DNAase/0.1% ovomucoid before centrifugation at 800 rpm for 5 minutes. The supernatant is replaced twice with $NaHCO_3$/HEPES-buffered basal Eagle medium (BME) plus 20 mM KCl. Cells are mechanically dissociated in 2 ml of BME by trituration through three Pasteur pipettes of successively decreasing tip diameter and then filtered through a 48 μM gauge filter. Cells are plated at a density of 150,000 cells in 50 μl in each well of poly-L-Lysin pre-coated 96 well plates (Falcon). The cells are nourished with BEM supplemented with 10% foetal calf serum, 2 mM glutamine (Biochrom), 20 mM KCl and gentamycin (Biochrom) and incubated at 36° C. with 5% $CO_2$ at 95% humidity. After 24 h, cytosine-β-D-arabinofuranoside (AraC, 10 μM) is added to the medium.

$IP_3$ Assay with [$^3$H]Myo-Inositol

After 6 DIV the culture medium is replaced completely with inositol free DMEM (ICN) containing [$^3$H]myo-inositol (Perkin Elmer) at a final concentration of 0.5 μCi/100 μl/well and incubated for a further 48 hours. The culture medium in each well is replaced with 100 μL Locke's buffer (contains in (mM) NaCl (156), KCl (5.6), $NaHCO_3$ (3.6), $MgCl_2$ (1.0), $CaCl_2$ (1.3), Glucose (5.6), HEPES (10)) with additional (20 mM Li, pH 7.4) and incubated for 15 min at 37° C. Locke's buffer is replaced with agonists/agonists/putative mGluR1 ligands in Locke's buffer and incubated for 45 min. These solutions are then replaced by 100 μL 0.1M HCl in each well and incubated for a further 10 mins on ice. The 96 well plates can be frozen at −20° C. at this stage until further analysis.

Home made resin exchange columns are prepared as follows. Empty Bio-Spin Chromatography columns (Biorad) are plugged with filter paper before filling with 1.1-1.2 ml of resin (AG1-X8 Biorad, 140-14444) suspended in 0.1M formic acid (24 g resin per 50 ml acid). The formic acid is allowed to run out before sealing the syringe tips and filling with 200-300 μL of 0.1M formic acid before storage at 4° C. On the day of assay, columns are washed with 1 ml of 0.1M formic acid followed by 1 ml of distilled water. The contents of each assay well are then added to one column and washed with 1 ml distilled water followed by 1 ml of 5 mM sodium tetraborate/60 mM sodium formate. The retained radioactive inositol phosphates are then eluted with 2*1 ml of 1M ammonium formate/0.1M formic acid into 24-well visiplates. Scintillation liquid (1.2 ml UltimaFlow AF) is added to each well and the plate sealed and vortexed before radioactivity is determined by conventional liquid scintillation counting (Microbeta, Perkin Elmer). Unless otherwise stated, all reagents are obtained from Sigma.

Compounds of the present invention have an $IC_{50}$ range of about 0.5 nM to about 100 μM (B-$IC_{50}$).

CONCLUSIONS

In conclusion, from the foregoing, it is apparent that the present invention provides novel, valuable, and unpredictable applications and uses of the compounds of the present invention, which compounds comprise the active principle according to the present invention, as well as novel pharmaceutical compositions thereof and methods of preparation thereof and of treating therewith, all possessed of the foregoing more specifically-enumerated characteristics and advantages.

The high order of activity of the active agent of the present invention and compositions thereof, as evidenced by the tests reported, is indicative of utility based on its valuable activity in human beings as well as in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug Administration, which are responsible for and authorized to pass judgment on such questions.

The instant tetrahydroquinolinones derivatives represent a novel class of Group I mGluR antagonists. In view of their potency, they will be useful therapeutics in a wide range of CNS disorders which involve excessive glutamate induced excitation.

These compounds accordingly find application in the treatment of the following disorders of a living animal body, especially a human: AIDS-related dementia, Alzheimer's disease, Creutzfeld-Jakob's syndrome, bovine spongiform encephalopathy (BSE) or other prion related infections, diseases involving mitochondrial dysfunction, diseases involving β-amyloid and/or tauopathy such as Down's syndrome, hepatic encephalopathy, Huntington's disease, motor neuron diseases such as amyotrophic lateral sclerosis (ALS), multiple sclerosis (MS), olivoponto-cerebellar atrophy, Parkinson's disease, vascular and frontal lobe dementia, eye injuries (e.g. glaucoma, retinopathy), head and spinal cord injuries, trauma, hypoglycaemia, hypoxia (e.g. perinatal), ischaemia (e.g. resulting from cardiac arrest, stroke, bypass operations or transplants), convulsions, glioma and other tumours, inner ear insult (e.g. in tinnitus, sound or drug-induced), L-dopa-induced and tardive dyskinesias.

These compounds also find application in the treatment of the following disorders of a living animal body, especially a human: addiction (nicotine, alcohol, opiate, cocaine, amphetamine obesity and others), amyotrophic lateral sclerosis (ALS), anxiety and panic disorders, attention deficit hyperactivity disorder (ADHD), restless leg syndrome and hyperactive children, autism, convulsions/epilepsy, dementia (e.g. in Alzheimer's disease, Korsakoff syndrome, vascular dementia, HIV infections), depression (including that resulting from Borna virus infection) and bipolar manic-depressive disorder, drug tolerance e.g. to opioids, dyskinesia (e.g. L-Dopa-induced, tardive dyskinesia or in Huntington's disease), fragile-X syndrome, Huntington's chorea, irritable bowel syndrome (IBS), migraine, multiple sclerosis, muscle spasms, pain (chronic and acute), Parkinson's disease, schizophrenia, spasticity, tinnitus, Tourette's syndrome, urinary incontinence and vomiting.

The method-of-treating a living animal body with a compound of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the compounds of the present invention in the manufacture of a medicament for the treatment of a living animal for inhibition of progression or alleviation of selected ailments or conditions, particularly ailments or conditions susceptible to treatment with an Group I mGluR antagonist, is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active ingredient with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or dermal use, also in accord with the foregoing.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby reference.

We claim:

1. A compound selected from those of Formula IA

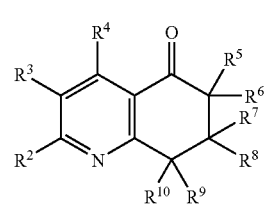

IA wherein $R^2$ represents $C_{2-6}$alkyl, cyclo$C_{3-12}$alkyl, cyclo$C_{3-12}$alkyl-$C_{1-6}$alkyl, $C_{2-6}$alkenyl, $C_{2-6}$alkynyl, aryl, biaryl, aryl-heteroaryl, heteroaryl-heteroaryl, heteroaryl-aryl, aryl$C_{1-6}$alkyl, aryl$C_{2-6}$alkenyl, aryl$C_{2-6}$alkynyl, heteroaryl, heteroaryl$C_{1-6}$alkyl, heteroaryl$C_{2-6}$alkenyl, heteroaryl$C_{2-6}$alkynyl, 2,3-dihydro-1H-indenyl, $C_{2-6}$alkoxy, hydroxy-$C_{2-6}$alkoxy, cyclo$C_{3-12}$alkoxy, cyclo$C_{3-12}$alkyl-$C_{1-6}$alkoxy, aryloxy, aryl-$C_{1-6}$alkoxy, $C_{1-6}$alkoxy$C_{1-6}$alkyl, $C_{1-6}$alkylthio, $C_{4-6}$alkenylthio, cyclo$C_{3-12}$alkylthio, cyclo$C_{3-12}$alkyl-$C_{1-6}$alkylthio, cyclo$C_{3-12}$alkyl-$C_{3-6}$alkenylthio, $C_{1-6}$alkoxy$C_{1-6}$alkylthio, $C_{1-6}$alkoxy$C_{3-6}$alkenylthio, aryl$C_{3-6}$alkenylthio, heteroaryl$C_{1-6}$alkylthio, $C_{1-6}$alkylsulfonyl, cyclo$C_{3-12}$alkyl-$C_{1-6}$alkylsulfonyl, aryl$C_{1-6}$alkylsulfonyl, $C_{1-6}$alkylamino, di-$C_{1-6}$alkylamino, cyclo$C_{3-12}$alkylamino, $C_1$-$C_6$alkoxy-cyclo$C_3$-$C_{12}$alkylamino, cyclo$C_{3-12}$alkyl-$C_{1-6}$alkylamino, di-$C_{1-6}$alkylamino-$C_{1-6}$alkyl, $C_{1-6}$alkoxy-$C_{2-6}$alkylamino, arylamino, aryl$C_{1-6}$alkylamino, N-cyclo$C_{3-12}$alkyl-N—$C_{1-6}$alkylamino, N-aryl-N—$C_{1-6}$alkylamino, N-aryl $C_{1-6}$alkyl-N—$C_{1-6}$alkylamino, 2-indanylamino, 1,2,3,4-tetrahydroisoquinolin-2-yl, tetrahydrofuryl, pyrrolidino, piperidino, 4-arylpiperidino, 4-heteroarylpiperidino, morpholino, piperazino, 4-$C_{1-6}$alkylpiperazino, 4-arylpiperazino, hexamethyleneimino, benzazepinyl, 1,3-dihydro-2H-isoindol-2-yl, heteroaryl$C_{1-6}$alkoxy, heteroarylamino, heteroaryl$C_{1-6}$alkylamino, —NHC(=O)—$R^{11}$, —NHSO$_2$—$R^{11}$, —NHC(=O)OR$^{11}$, —C(=O)NH—$R^{11}$, —$C_{1-6}$alkyl-C(=O)NH—$R^{11}$, wherein the cyclo$C_{3-12}$alkyl is optionally unsaturated and wherein one carbon atom in the cyclo$C_{3-12}$alkyl moiety may be replaced by an oxygen atom or an NR$^{12}$-moiety;

$R^3$ represents hydrogen, cyano, nitro, halogen, $C_{1-6}$alkyl, CF$_3$, heteroaryl, 2,3-dihydro-1H-indenyl, hydroxy, $C_{1-6}$alkoxy, pyrrolidino, piperidino, morpholino;

$R^4$ represents hydrogen, halogen, nitro, $C_{1-6}$alkoxy, hydroxy-$C_{2-6}$alkoxy;

$R^5$ and $R^6$ which may be the same or different, each independently represent hydrogen, hydroxy, $C_{1-6}$alkyl, cyclo$C_{3-12}$alkyl, $C_{2-6}$alkenyl, $C_{1-6}$alkoxy, $C_{1-6}$alkoxy$C_{1-6}$alkyl, $C_{1-6}$alkylthio, $C_{3-6}$alkenylthio, $C_{1-6}$alkylamino, di-$C_{1-6}$alkylamino, cyclo$C_{3-12}$alkylamino, di-$C_{1-6}$alkylamino$C_{1-6}$alkyl, aryl$C_{1-6}$alkylamino, aryl, aryl$C_{1-6}$alkyl, or aryl$C_{2-6}$alkenyl;

or one of $R^5$ and $R^6$ and one of $R^7$ and $R^8$ together represent —(CH$_2$)$_n$— with n being 3, 4 or 5, while the remaining of $R^5$ and $R^6$ as well as $R^7$ and $R^8$ are both hydrogen;

$R^7$ and $R^8$, which may be the same or different, each independently represent hydrogen, $C_{1-6}$alkyl, cycloC$_{3-12}$alkyl, C$_{2-6}$alkenyl, cycloC$_{3-12}$alkyl-C$_{1-6}$alkyl, aryl, arylC$_{1-6}$alkyl, heteroaryl, or heteroaryl-C$_{1-6}$alkyl;

or R$^7$ and R$^8$ may together represent —(CH$_2$)$_m$— with m being 4, 5 or 6;

R$^9$ and R$^{10}$, which may be the same or different, each independently represent hydrogen, C$_{1-6}$alkyl, hydroxy, or C$_{1-6}$alkoxy;

R$^{11}$ represents hydrogen, C$_{1-6}$alkyl, C$_{2-6}$alkenyl, aryl; arylC$_{1-6}$alkyl, arylC$_{2-6}$alkenyl, heteroaryl, heteroarylC$_{1-6}$alkyl, C$_{1-6}$alkylamino, di-C$_{1-6}$alkylamino, cycloC$_{3-12}$alkylamino, di-C$_{1-6}$alkylaminoC$_{1-6}$alkyl, arylamino, arylC$_{1-6}$alkylamino, arylC$_{2-6}$alkenylamino, N-aryl-N—C$_{1-6}$alkylamino, pyrrolidino, piperidino, morpholino, hexamethyleneimino, benzazepinyl, 1,3-dihydro-2H-isoindol-2-yl, cycloC$_{3-12}$alkyl, or cycloC$_{3-12}$alkylC$_{1-6}$alkyl, wherein the cycloC$_{3-12}$alkyl is optionally unsaturated and wherein one carbon atom in the cycloC$_{3-12}$alkyl moiety may be replaced by an oxygen atom or an NR$^{12}$-moiety;

R$^{12}$ represents hydrogen, C$_{1-6}$alkyl, aryl, heteroaryl, arylC$_{1-6}$alkyl or heteroarylC$_{1-6}$alkyl;

and optical isomers, pharmaceutically-acceptable acid and base addition salts, and hydrates thereof;

it being understood that:

R$^2$ may not represent unsubstituted phenyl or naphthyl;

R$^2$ may not represent substituted phenyl having at least one ortho-substituent other than hydrogen, relative to the tetrahydroquinoline ring of formula IA to which the phenyl is attached;

R$^2$ may not represent dimethylamino;

if one of R$^5$ and R$^6$ and one of R$^7$ and R$^8$ together represent —(CH$_2$)$_n$— with n being 3, 4 or 5, while the remaining of R$^5$ and R$^6$ as well as R$^7$ and R$^8$ are both hydrogen, then R$^2$ may also be halogen;

if R$^3$ and R$^4$ both represent hydrogen, then R$^2$ may not represent aryl-heteroaryl, heteroaryl-heteroaryl, arylC$_{2-6}$alkynyl, or heteroarylC$_{2-6}$alkynyl;

if R$^3$, R$^4$, R$^5$, R$^6$, R$^7$, R$^8$, R$^9$ and R$^{10}$ all represent hydrogen at the same time, then R$^2$ may not represent C$_{2-6}$alkyl;

if R$^3$ is cyano, then R$^2$ may not represent methylthio or ethylthio;

R$^7$ and R$^8$ may not represent furyl;

and the compound of Formula IA may not represent:
2-Benzyloxy-7,8-dihydro-6H-quinoline-5-one, 2-Phenoxy-7,8-dihydro-6H-quinolin-5-one, 2-(1H-Indol-3-yl)-7,8-dihydro-6H-quinolin-5-one, 2-(1H-Indol-3-yl)-7,7-dimethyl-7,8-dihydro-6H-quinolin-5-one, 2-Thiophen-2-yl-7,8-dihydro-6H-quinolin-5-one, 2-Ethoxy-7,8-dihydro-6H-quinolin-5-one, 7,7-Dimethyl-2-(6-methyl-pyridin-3-ylmethylsulfanyl)-5-oxo-5,6,7,8-tetrahydro-quinoline-3-carbonitrile, 2-(1H-Benzoimidazol-2-ylmethylsulfanyl)-7,7-dimethyl-5-oxo-5,6,7,8-tetrahydro-quinoline-3-carbonitrile, 2-(4-Methoxy-phenyl)-7,8-dihydro-6H-quinolin-5-one, 2-(4-Chloro-phenyl)-7,7-dimethyl-7,8-dihydro-6H-quinolin-5-one, 2-(4-Fluoro-phenyl)-7,8-dihydro-6H-quinolin-5-one, 2-(4-Isopropyl-phenyl)-5-oxo-5,6,7,8-tetrahydro-quinoline-3-carbonitrile, or 2-Cyclohexyl-7,8-dihydro-6H-quinolin-5-one.

2. A compound of claim 1, wherein R$^3$ represents hydrogen, cyano or nitro.

3. A compound of claim 1, wherein R$^4$ represents hydrogen.

4. A compound of claim 1, wherein R$^5$ and R$^6$, which may be the same or different, each independently represent hydrogen or C$_{1-6}$alkyl, and R$^7$ and R$^8$, which may be the same or different, each independently represent hydrogen, C$_{1-6}$alkyl or cycloC$_{3-12}$alkyl, or wherein one of R$^5$ and R$^6$ and one of R$^7$ and R$^8$ together represent —(CH$_2$)$_n$— with n being 3, 4 or 5, while the remaining of R$^5$ and R$^6$ as well as R$^7$ and R$^8$ are both hydrogen, or wherein R$^7$ and R$^8$ may together represent —(CH$_2$)$_m$— with m being 4, 5 or 6.

5. A compound of claim 4, wherein R$^5$ and R$^6$, which may be the same or different, each independently represent hydrogen, methyl, or ethyl.

6. A compound of claim 4, wherein R$^7$ and R$^8$, which may be the same or different, each independently represent hydrogen, methyl, or cyclohexyl.

7. A compound of claim 4, wherein one of R$^5$ and R$^6$ and one of R7 and R$^8$ together represent —(CH$_2$)$_n$— with n being 4, while the remaining of R$^5$ and R$^6$ ad well as R$^7$ and R$^8$ are both hydrogen.

8. A compound of claim 4, wherein R$^7$ and R$^8$ together represent —(CH$_2$)$_m$— with m being 5 or 6.

9. A compound of claim 1, wherein R$^9$ and R$^{10}$, which may be the same or different, each independently represent hydrogen or C$_{1-6}$alkyl.

10. A compound of claim 9, wherein R$^9$ and R$^{10}$, which may be the same or different, each independently represent hydrogen or methyl.

11. A compound of claim 1, wherein R$^2$ represents C$_{1-6}$alkylthio, C$_{4-6}$alkenylthio or cycloC$_{3-12}$alkylthio.

12. A compound of claim 11, wherein
R$^3$ represents hydrogen or cyano;
R$^4$ represents hydrogen, halogen, nitro or C$_{1-4}$alkoxy;
R$^5$ and R$^6$, which may be the same or different, each independently represent hydrogen or C$_{1-6}$alkyl;
R$^7$ and R$^8$, which may be the same or different, each independently represent hydrogen, C$_{1-6}$alkyl or cycloC$_{3-12}$alkyl or R$^7$ and R$^8$ may together represent —(CH$_2$)$_m$— with m being 4, 5 or 6; and
R$^9$ and R$^{10}$, which may be the same or different, each independently represent hydrogen or C$_{1-6}$alkyl.

13. A compound of claim 12, wherein R$^3$ represents cyano.

14. A compound of claim 12, wherein R$^4$ represents hydrogen.

15. A compound of claim 12, wherein R$^5$ and R$^6$, which may be the same or different, each independently represent hydrogen, methyl, or ethyl.

16. A compound of claim 12, wherein R$^7$ and R$^8$, which may be the same or different, each independently represent hydrogen, methyl, or cyclohexyl.

17. A compound of claim 12, wherein R$^7$ and R$^8$ together represent —(CH$_2$)$_m$— with m being 5 or 6.

18. A compound of claim 12, wherein R$^9$ and R$^{10}$, which may be the same or different, each independently represent hydrogen or methyl.

19. A compound of claim 1, wherein R$^2$ represents C$_{2-6}$alkoxy, cycloC$_{3-12}$alkoxy, cycloC$_{3-12}$alkyl-C$_{1-6}$alkoxy, aryloxy, aryl-C$_{1-6}$alkoxy or C$_{1-6}$alkoxyC$_{1-6}$alkyl.

20. A compound claim 19, wherein
R$^3$ represents hydrogen or cyano;
R$^4$ represents hydrogen, halogen, nitro or C$_{1-6}$alkoxy;
R$^5$ and R$^6$, which may be the same or different, each independently represent hydrogen or C$_{1-6}$alkyl;
R$^7$ and R$^8$, which may be the same or different, each independently represent hydrogen, C$_{1-6}$alkyl or cycloC$_{3-12}$alkyl or R$^7$ and R$^8$ may together represent —(CH$_2$)$_m$— with m being 4, 5 or 6; and
R$^9$ and R$^{10}$, which may be the same or different, each independently represent hydrogen or C$_{1-6}$alkyl.

21. A compound of claim 20, wherein R$^3$ represents cyano.

22. A compound of claim 20, wherein R$^4$ represents hydrogen.

23. A compound of claim 20, wherein $R^5$ and $R^6$, which may be the same or different, each independently represent hydrogen, methyl, or ethyl.

24. A compound of claim 20, wherein $R^7$ and $R^8$, which may be the same or different, each independently represent hydrogen, methyl, or cyclohexyl.

25. A compound of claim 20, wherein $R^7$ and $R^8$ together represent —$(CH_2)_m$— with m being 5 or 6.

26. A compound of claim 20, wherein $R^9$ and $R^{10}$, which may be the same or different, each independently represent hydrogen or methyl.

27. A compound of claim 1, wherein $R^2$ represents $C_{1-6}$alkylamino, di-$C_{1-6}$alkylamino, cyclo$C_{3-12}$alkylamino, cyclo$C_{3-12}$alkyl-$C_{1-6}$alkylamino, di-$C_{1-6}$alkylamino $C_{1-6}$alkyl, $C_{1-6}$alkoxy-$C_{2-6}$alkylamino, arylamino, aryl$C_{1-6}$alkylamino, N-cyclo$C_{3-12}$alkyl-N—$C_{1-6}$alkylamino, N-aryl-N—$C_{1-6}$alkylamino, N-aryl$C_{1-6}$alkyl-N—$C_{1-6}$alkylamino, wherein the aryl moieties may be unsubstituted or substituted by one or two substituents, each independently selected from methoxy, cyano, halogen, hydroxy, methyl, pyridyl, morpholinyl and piperidinyl.

28. A compound of claim 27, wherein
$R^3$ represents hydrogen or cyano;
$R^4$ represents hydrogen, halogen, nitro or $C_{1-6}$alkoxy;
$R^5$ and $R^6$, which may be the same or different, each independently represent hydrogen or $C_{1-6}$alkyl;
$R^7$ and $R^8$, which may be the same or different, each independently represent hydrogen, $C_{1-6}$alkyl or cyclo$C_{3-12}$alkyl, or $R^7$ and $R^8$ may together represent —$(CH_2)_m$— with m being 4, 5 or 6; and
$R^9$ and $R^{10}$, which may be the same or different, each independently represent hydrogen or $C_{1-6}$alkyl.

29. A compound of claim 28, wherein $R^3$ represents cyano.

30. A compound of claim 28, wherein $R^4$ represents hydrogen.

31. A compound of claim 28, wherein $R^5$ and $R^6$, which may be the same or different, each independently represent hydrogen, methyl, or ethyl.

32. A compound of claim 28, wherein $R^7$ and $R^8$, which may be the same or different, each independently represent hydrogen, methyl, or cyclohexyl.

33. A compound of claim 28, wherein $R^7$ and $R^8$ together represent —$(CH_2)_m$— with m being 5 or 6.

34. A compound of claim 28, wherein $R^9$ and $R^{10}$, which may be the same or different, each independently represent hydrogen or methyl.

35. A compound of claim 1, wherein $R^2$ represents $C_{2-6}$alkyl, cyclo$C_{3-12}$alkyl, cyclo$C_{3-12}$alkyl-$C_{1-6}$alkyl, $C_{2-6}$alkenyl or aryl$C_{1-6}$alkyl.

36. A compound of claim 35, wherein $R^2$ represents adamantyl.

37. A compound of claim 35, wherein
$R^3$ represents hydrogen, cyano, nitro or morpholino;
$R^4$ represents hydrogen, halogen, nitro or $C_{1-6}$alkoxy;
$R^5$ and $R^6$, which may be the same or different, each independently represent hydrogen or $C_{1-6}$alkyl;
$R^7$ and $R^8$, which may be the same or different, each independently represent hydrogen, $C_{1-6}$alkyl or cyclo$C_{3-12}$alkyl, or $R^7$ and $R^8$ may together represent —$(CH_2)_m$— with m being 4, 5 or 6; and
$R^9$ and $R^{10}$, which may be the same or different, each independently represent hydrogen or $C_{1-6}$alkyl.

38. A compound of claim 37, wherein $R^3$ represents hydrogen, cyano, or nitro.

39. A compound of claim 37, wherein $R^4$ represents hydrogen.

40. A compound of claim 37, wherein $R^5$ and $R^6$, which may be the same or different, each independently represent hydrogen, methyl, or ethyl.

41. A compound of claim 37, wherein $R^7$ and $R^8$, which may be the same or different, each independently represent hydrogen, methyl, or cyclohexyl.

42. A compound of claim 37, wherein $R^7$ and $R^8$ together represent —$(CH_2)_m$— with m being 5 or 6.

43. A compound of claim 37, wherein $R^9$ and $R^{10}$, which may be the same or different, each independently represent hydrogen or methyl.

44. A compound of claim 1, wherein $R^2$ represents biaryl or heteroaryl-aryl, wherein the aryl moieties may be unsubstituted or substituted by one or two substituents each independently selected from methoxy, cyano, halogen, hydroxy and methyl.

45. A compound of claim 44, wherein $R^2$ represents heteroaryl-aryl, wherein the heteroaryl moiety is selected from pyridyl, pyrimidyl, oxazolyl, oxadiazolyl, thiazolyl and imidazolyl.

46. A compound of claim 44, wherein the aryl moiety is substituted in the meta position.

47. A compound of claim 44, wherein
$R^3$ represents hydrogen, cyano or nitro;
$R^4$ represents hydrogen;
$R^5$ and $R^6$, which may be the same or different, each independently represent hydrogen or $C_{1-6}$alkyl;
$R^7$ and $R^8$, which may be the same or different, each independently represent hydrogen, $C_{1-6}$alkyl or cyclo$C_{3-12}$alkyl, or $R^7$ and $R^8$ may together represent —$(CH_2)_m$— with m being 4, 5 or 6; and
$R^9$ and $R^{10}$, which may be the same or different, each independently represent hydrogen or $C_{1-6}$alkyl.

48. A compound of claim 47, wherein $R^3$ represents hydrogen or cyano.

49. A compound of claim 47, wherein $R^4$ represents hydrogen.

50. A compound of claim 47, wherein $R^5$ and $R^6$, which may be the same or different, each independently represent hydrogen or methyl.

51. A compound of claim 47, wherein $R^7$ and $R^8$, which may be the same or different, each independently represent hydrogen, methyl, or cyclohexyl.

52. A compound of claim 47, wherein $R^7$ and $R^8$ together represent —$(CH_2)_m$— with m being 5 or 6.

53. A compound of claim 47, wherein $R^9$ and $R^{10}$, which may be the same or different, each independently represent hydrogen or methyl.

54. A compound of claim 1, wherein one of $R^5$ and $R^6$ and one of $R^7$ and $R^8$ together represent —$(CH_2)_n$— with n being 3, 4 or 5, while the remaining of $R^5$ and $R^6$ as well as $R^7$ and $R^8$ are both hydrogen, and wherein $R^2$ represents halogen, aryl, heteroaryl, arylamino, aryl$C_{1-6}$alkylamino, cyclo$C_{3-12}$alkyl, piperidino, 4-arylpiperidino, morpholino, piperazino, 4-$C_{1-6}$alkylpiperazino, or 4-arylpiperazino, wherein the aryl moieties and the heteroaryl moieties may be unsubstituted or substituted by one or two substituents, each independently selected from methoxy, cyano, halogen, hydroxy and methyl.

55. A compound of claim 54, wherein the aryl and/or heteroaryl moiety is substituted in the meta position.

56. A compound of claim 54, wherein $R^2$ represents phenylamino, phenylethylamino, adamantyl, 4-phenylpiperidino, or 4-phenylpiperazino, wherein the phenyl moiety may be unsubstituted or substituted by one or two substituents, each independently selected from methoxy, cyano, halogen, hydroxyl and methyl.

57. A compound of claim 54, wherein n is 4.

58. A compound of claim 54, wherein
R³ represents hydrogen, cyano or nitro;
R⁴ represents hydrogen; and
R⁹ and R¹⁰, which may be the same or different, each independently represent hydrogen or $C_{1-6}$alkyl.

59. A compound of claim 58, wherein R³ represents hydrogen or cyano.

60. A compound of claim 58, wherein R⁴ represents hydrogen.

61. A compound of claim 58, wherein R⁹ and R¹⁰, which may be the same or different, each independently represent hydrogen.

62. A compound of claim 1, which is selected from:
7,7-Dimethyl-2-(2-methyl-allylsulfanyl)-5-oxo-5,6,7,8-tetrahydroquinoline-3-carbonitrile,
2-Isopropylsulfanyl-7,7-dimethyl-5-oxo-5,6,7,8-tetrahydroquinoline-3-carbonitrile,
7,7-Dimethyl-5-oxo-2-propylsulfanyl-5,6,7,8-tetrahydroquinoline-3-carbonitrile,
2-(2-Methyl-allylsulfanyl)-5-oxo-5,6,7,8-tetrahydroquinoline-3-carbonitrile,
2-Butylsulfanyl-7,7-dimethyl-5-oxo-5,6,7,8-tetrahydroquinoline-3-carbonitrile,
2-Isobutylsulfanyl-7,7-dimethyl-5-oxo-5,6,7,8-tetrahydroquinoline-3-carbonitrile,
2-Benzylsulfanyl-7,7-dimethyl-3-nitro-7,8-dihydro-6H-quinolin-5-one, and
2-Benzylsulfanyl-3-chloro-7,7-dimethyl-7,8-dihydro-6H-quinolin-5-one,
and optical isomers, pharmaceutically-acceptable acid and base addition salts, and hydrates thereof.

63. A compound of claim 1, which is selected from:
2-Cyclohexyloxy-7,7-dimethyl-7,8-dihydro-6H-quinolin-5-one,
2-Isobutoxy-7,7-dimethyl-5,6,7,8-tetrahydroquinolin-5-one,
2-Benzyloxy-7,7-dimethyl-7,8-dihydro-6H-quinolin-5-one,
2-Benzyloxy-7-(4-chloro-phenyl)-7,8-dihydro-6H-quinolin-5-one,
2-Isobutoxy-7-phenyl-7,8-dihydro-6H-quinolin-5-one,
2-Phenoxy-7-phenyl-7,8-dihydro-6H-quinolin-5-one,
2-Benzyloxy-7,7-pentamethylene-7,8-dihydro-6H-quinoline-5-one,
2-Ethoxy-7,7-pentamethylene-7,8-dihydro-6H-quinoline-5-one,
2-(2-Hydroxyethoxy)-1-yl-7,7-pentamethylene-7,8-dihydro-6H-quinoline-5-one,
2-Benzyloxy-7-ethyl-7,8-dihydro-6H-quinolin-5-one, and
2-Ethoxy-7-furan-2-yl-7,8-dihydro-6H-quinolin-5-one,
and optical isomers, pharmaceutically-acceptable acid and base addition salts, and hydrates thereof.

64. A compound of claim 1, which is selected from:
2-Biphenyl-4-yl-7,8-dihydro-6H-quinolin-5-one,
2-Biphenyl-4-yl-5-oxo-5,6,7,8-tetrahydro-quinoline-3-carbonitrile,
2-(3-Methoxy-4-pyridin-3-yl-phenyl)-7,8-dihydro-6H-quinolin-5-one, and
2-(3-Methoxy-4-pyridin-2-yl-phenyl)-7,8-dihydro-6H-quinolin-5-one,
and optical isomers, pharmaceutically-acceptable acid and base addition salts, and hydrates thereof.

65. A compound of claim 1, which is selected from:
3-[2-(5-Oxo-5,6,7,8-tetrahydro-quinolin-2-yl)-thiazol-5-yl]-benzonitrile,
3-Fluoro-5-[2-(5-oxo-5,6,7,8-tetrahydro-quinolin-2-yl)-thiazol-5-yl]-benzonitrile,
3-[2-(7,7-Dimethyl-5-oxo-5,6,7,8-tetrahydro-quinolin-2-yl)-thiazol-5-yl]-benzonitrile,
3-[2-(7,7-Dimethyl-5-oxo-5,6,7,8-tetrahydro-quinolin-2-yl)-thiazol-5-yl]-5-fluoro-benzonitrile,
3-[2-(5-Oxo-5,6,7,8-tetrahydro-quinolin-2-yl)-oxazol-5-yl]-benzonitrile,
3-[3-(5-Oxo-5,6,7,8-tetrahydro-quinolin-2-yl)-isoxazol-5-yl]-benzonitrile,
3-[2-(7,7-Dimethyl-5-oxo-5,6,7,8-tetrahydro-quinolin-2-yl)-oxazol-5-yl]-benzonitrile,
3-[3-(7,7-Dimethyl-5-oxo-5,6,7,8-tetrahydro-quinolin-2-yl)-isoxazol-5-yl]-benzonitrile,
3-[2-(7,7-Dimethyl-5-oxo-5,6,7,8-tetrahydro-quinolin-2-yl)-oxazol-5-yl]-5-fluoro-benzonitrile,
3-[3-(7,7-Dimethyl-5-oxo-5,6,7,8-tetrahydro-quinolin-2-yl)-isoxazol-5-yl]-5-fluoro-benzonitrile,
7,7-Dimethyl-2-(5-pyridin-3-yl-thiazol-2-yl)-7,8-dihydro-6H-quinolin-5-one,
2-(5-Pyridin-3-yl-thiazol-2-yl)-7,8-dihydro-6H-quinolin-5-one,
3-[3-(7,7-Dimethyl-5-oxo-5,6,7,8-tetrahydro-quinolin-2-yl)-isoxazol-5-yl]-benzonitrile, and
7,7-Dimethyl-5-oxo-2-(3,4,5,6-tetrahydro-2H-[4,4']bipyridinyl-1-yl)-5,6,7,8-tetrahydro-quinoline-3-carbonitrile,
and optical isomers, pharmaceutically-acceptable acid and base addition salts, and hydrates thereof.

66. A compound of claim 1, which is selected from:
7,7-Dimethyl-2-phenethyl-7,8-dihydro-6H-quinolin-5-one,
2-Benzyl-7,7-dimethyl-7,8-dihydro-6H-quinolin-5-one,
2-[2-(2-Methoxyphenyl)ethyl]-7,8-dihydro-6H-quinolin-5-one,
2-Phenethyl-7,8-dihydro-6H-quinolin-5-one,
2-Cyclohexylmethyl-7,7-tetramethylene-7,8-dihydro-6H-quinolin-5-one,
2-Benzyl-7,7-tetramethylene-7,8-dihydro-6H-quinolin-5-one,
2-Benzyl-6-propyl-7,8-dihydro-6H-quinolin-5-one,
2-Benzyl-6-ethyl-7,8-dihydro-6H-quinolin-5-one,
2-Benzyl-7-propyl-7,8-dihydro-6H-quinolin-5-one,
2-Benzyl-6,6-dimethyl-7,8-dihydro-6H-quinolin-5-one,
2-Benzyl-6,6,8-trimethyl-7,8-dihydro-6H-quinolin-5-one,
2-Benzyl-7-ethyl-7,8-dihydro-6H-quinolin-5-one,
(cis,trans) 2-Benzyl-6-ethyl-8-methyl-7,8-dihydro-6H-quinolin-5-one and 2-benzyl-8-ethyl-6-methyl-7,8-dihydro-6H-quinolin-5-one,
2-Cyclohexylmethyl-7,7-dimethyl-7,8-dihydro-6H-quinolin-5-one,
2-Cyclohexylmethyl-7-ethyl-7,8-dihydro-6H-quinolin-5-one,
2-Cyclohexylmethyl-6,6-dimethyl-7,8-dihydro-6H-quinolin-5-one,
2-Cyclohexylmethyl-6-ethyl-7,8-dihydro-6H-quinolin-5-one,
2-Benzyl-7,8-dihydro-6H-quinolin-5-one,
7,7-Dimethyl-2-styryl-7,8-dihydro-6H-quinolin-5-one,
2-[2-(3,5-Dimethoxy-phenyl)-vinyl]-7,8-dihydro-6H-quinolin-5-one, and
2-[2-(3,5-Dimethoxy-phenyl)-vinyl]-7,7-dimethyl-7,8-dihydro-6H-quinolin-5-one,
2-[1-(4-Methoxy-phenyl)-piperidin-4-yl]-7,7-dimethyl-5-oxo-5,6,7,8-tetrahydro-quinoline-3-carbonitrile, and optical isomers, pharmaceutically-acceptable acid and base addition salts, and hydrates thereof.

67. A compound of claim 1, which is selected from
2-Adamantan-1-yl-6-propyl-7,8-dihydro-6H-quinolin-5-one,
2-Adamantan-1-yl-7,7-dimethyl-7,8-dihydro-6H-quinolin-5-one,
2-Adamantan-1-yl-7,8-dihydro-6H-quinolin-5-one,
2-Adamantan-1-yl-7,7-pentamethylene-7,8-dihydro-6H-quinoline-5-one,
2-Cyclohexyl-7-propyl-7,8-dihydro-6H-quinolin-5-one,
2-Adamantan-1-yl-6-ethyl-8-methyl-7,8-dihydro-6H-quinolin-5-one,
2-Adamantan-1-yl-6,6-dimethyl-7,8-dihydro-6H-quinolin-5-one,
(cis,trans) 2-Adamantan-1-yl-6-ethyl-8-methyl-7,8-dihydro-6H-quinolin-5-one
and 2-adamantan-1-yl-8-ethyl-6-methyl-7,8-dihydro-6H-quinolin-5-one,
2-Cyclohexyl-7-isopropyl-7,8-dihydro-6H-quinolin-5-one, and
2-Cyclohexyl-6-ethyl-6-methyl-7,8-dihydro-6H-quinolin-5-one,
and optical isomers, pharmaceutically-acceptable acid and base addition salts, and hydrates thereof.

68. A compound of claim 1, which is selected from:
2-Isopropyl-7,7-dimethyl-7,8-dihydro-6H-quinolin-5-one,
7-(4-Dimethylamino-phenyl)-2-hexyl-7,8-dihydro-6H-quinolin-5-one,
cis,trans 6-Ethyl-2-hexyl-6,8-dimethyl-7,8-dihydro-6H-quinolin-5-one,
2-Hexyl-7-phenyl-7,8-dihydro-6H-quinolin-5-one,
2-Hexyl-cis,trans-6,8-dimethyl-7,8-dihydro-6H-quinolin-5-one,
2-Hexyl-7-propyl-7,8-dihydro-6H-quinolin-5-one,
6-Ethyl-2-hexyl-7,8-dihydro-6H-quinolin-5-one,
2-Hexyl-6,6,8-trimethyl-7,8-dihydro-6H-quinolin-5-one,
2-Hexyl-6,6-dimethyl-7,8-dihydro-6H-quinolin-5-one,
cis,trans-8-Ethyl-2-hexyl-6-methyl-7,8-dihydro-6H-quinolin-5-one and
cis,trans-6-ethyl-2-hexyl-8-methyl-7,8-dihydro-6H-quinolin-5-one,
2-Hexyl-7-isopropyl-7,8-dihydro-6H-quinolin-5-one,
2-Hexyl-7-(3-methoxy-phenyl)-7,8-dihydro-6H-quinolin-5-one,
2-Hexyl-6,6-dimethyl-7,8-dihydro-6H-quinolin-5-one,
and optical isomers, pharmaceutically-acceptable acid and base addition salts, and hydrates thereof.

69. A compound of claim 1, which is selected from:
7-Phenyl-2-pyridin-2-yl-7,8-dihydro-6H-quinolin-5-one,
2-(4-Methoxy-phenyl)-6,6-dimethyl-7,8-dihydro-6H-quinolin-5-one,
cis,trans-6-Ethyl-2-(4-methoxy-phenyl)-cis,trans-6,8-dimethyl-7,8-dihydro-6H-quinolin-5-one,
2-(3-Methoxy-phenyl)-7,7-dimethyl-7,8-dihydro-6H-quinolin-5-one,
2-(3-Methoxy-phenyl)-6-ethyl-7,8-dihydro-6H-quinolin-5-one,
2-(3-Methoxy-phenyl)-6-methyl-7,8-dihydro-6H-quinolin-5-one,
2-(3-Methoxy-phenyl)-6,6,8-trimethyl-7,8-dihydro-6H-quinolin-5-one,
cis,trans 6-Ethyl-2-(3-methoxy-phenyl)-8-methyl-7,8-dihydro-6H-quinolin-5-one and 8-ethyl-2-(3-methoxy-phenyl)-6-methyl-7,8-dihydro-6H-quinolin-5-one,
cis 2-(3-Methoxy-phenyl)-6,8-dimethyl-7,8-dihydro-6H-quinolin-5-one,
2-(3-Methoxy-phenyl)-6,6-dimethyl-7,8-dihydro-6H-quinolin-5-one,
2-(3-Methoxy-phenyl)-7,7-tetramethylene-7,8-dihydro-6H-quinolin-5-one,
2-(4-Methoxy-phenyl)-6-propyl-7,8-dihydro-6H-quinolin-5-one,
2-(3-Methoxy-phenyl)-6-propyl-7,8-dihydro-6H-quinolin-5-one,
2-(4-Methoxy-phenyl)-6,6,8-trimethyl-7,8-dihydro-6H-quinolin-5-one,
2-(4-Methoxy-phenyl)-7,7-tetramethylene-7,8-dihydro-6H-quinolin-5-one,
7-Ethyl-2-(4-methoxy-phenyl)-7,8-dihydro-6H-quinolin-5-one,
2-(4-Methoxy-phenyl)-6,8-dimethyl-7,8-dihydro-6H-quinolin-5-one,
2-(4-Methoxy-phenyl)-8-methyl-6-propyl-7,8-dihydro-6H-quinolin-5-one,
7-Isopropyl-2-pyridin-3-yl-7,8-dihydro-6H-quinolin-5-one,
2-(1,3-Dihydro-isoindol-2-yl)-7,7-dimethyl-5-oxo-5,6,7,8-tetrahydro-quinoline-3-carbonitrile, and
2-(3,4-Dihydro-1H-isoquinolin-2-yl)-7,7-dimethyl-5-oxo-5,6,7,8-tetrahydro-quinoline-3-carbonitrile,
and optical isomers, pharmaceutically-acceptable acid and base addition salts, and hydrates thereof.

70. A compound of claim 1, which is selected from:
2-Hexylamino-7,7-dimethyl-5-oxo-5,6,7,8-tetrahydro-quinoline-3-carbonitrile,
7,7-Dimethyl-5-oxo-2-[(tetrahydro-furan-2-ylmethyl)-amino]-5,6,7,8-tetrahydro-quinoline-3-carbonitrile,
2-(2-Methoxy-ethylamino)-5-oxo-5,6,7,8-tetrahydro-quinoline-3-carbonitrile,
2-(Benzyl-methyl-amino)-5-oxo-5,6,7,8-tetrahydro-quinoline-3-carbonitrile,
5-Oxo-2-[(tetrahydro-furan-2-ylmethyl)-amino]-5,6,7,8-tetrahydro-quinoline-3-carbonitrile,
5-Oxo-2-[(pyridin-2-ylmethyl)-amino]-5,6,7,8-tetrahydro-quinoline-3-carbonitrile,
2-(Benzyl-methyl-amino)-7,7-dimethyl-5-oxo-5,6,7,8-tetrahydro-quinoline-3-carbonitrile,
7,7-Dimethyl-5-oxo-2-[(pyridin-3-ylmethyl)-amino]-5,6,7,8-tetrahydro-quinoline-3-carbonitrile,
7,7-Dimethyl-2-(1-phenyl-ethylamino)-7,8-dihydro-6H-quinolin-5-one,
2-(3,5-Dimethoxy-benzylamino)-7,8-dihydro-6H-quinolin-5-one,
2-(3,5-Difluoro-benzylamino)-7,8-dihydro-6H-quinolin-5-one,
5-Oxo-2-(1-phenyl-ethylamino)-5,6,7,8-tetrahydro-quinoline-3-carbonitrile,
2-(3-Fluoro-benzylamino)-7,8-dihydro-6H-quinolin-5-one,
2-Benzylamino-7,7-dimethyl-5-oxo-5,6,7,8-tetrahydro-quinoline-3-carbonitrile, and
2-Benzylamino-7,7-dimethyl-7,8-dihydro-6H-quinolin-5-one,
and optical isomers, pharmaceutically-acceptable acid and base addition salts, and hydrates thereof.

71. A compound of claim 1, which is selected from:
2-(4-Methoxy-phenylamino)-7,7-dimethyl-7,8-dihydro-6H-quinolin-5-one,
2-Phenylamino-7,8-dihydro-6H-quinolin-5-one,
2-(3-Methoxy-4-pyridin-2-yl-phenylamino)-7,7-dimethyl-7,8-dihydro-6H-quinolin-5-one, 2-(3-Methoxy-4-pyridin-3-yl-phenylamino)-7,7-dimethyl-7,8-dihydro-6H-quinolin-5-one,
2-(3-Fluoro-4-pyridin-2-yl-phenylamino)-7,7-dimethyl-7,8-dihydro-6H-quinolin-5-one,
7,7-Dimethyl-2-(pyridin-2-ylamino)-7,8-dihydro-6H-quinolin-5-one,
2-(3-Methoxy-phenylamino)-7,7-dimethyl-7,8-dihydro-6H-quinolin-5-one,
2-(Indan-2-ylamino)-7,7-dimethyl-5-oxo-5,6,7,8-tetrahydro-quinoline-3-carbonitrile,
7,7-Dimethyl-5-oxo-2-phenylamino-5,6,7,8-tetrahydro-quinoline-3-carbonitrile,
2-(4-Methoxy-phenylamino)-7,7-dimethyl-5-oxo-5,6,7,8-tetrahydro-quinoline-3-carbonitrile,
2-(4-Methoxy-phenylamino)-7,7-dimethyl-3-nitro-7,8-dihydro-6H-quinolin-5-one,
3-[(5-Oxo-5,6,7,8-tetrahydro-quinolin-2-ylamino)-methyl]-benzonitrile,
[4-(7,7-Dimethyl-5-oxo-5,6,7,8-tetrahydro-quinolin-2-ylamino)-2-methoxy-phenyl]-acetonitrile,
2-(3-Fluoro-4-pyridin-3-yl-phenylamino)-7,7-dimethyl-7,8-dihydro-6H-quinolin-5-one,
[4-(7,7-Dimethyl-5-oxo-5,6,7,8-tetrahydro-quinolin-2-ylamino)-2-fluoro-phenyl]-acetonitrile,
2-(3-Methoxy-4-pyridin-2-yl-phenylamino)-7,8-dihydro-6H-quinolin-5-one,
2-(3-Methoxy-4-pyridin-3-yl-phenylamino)-7,8-dihydro-6H-quinolin-5-one,
[2-Methoxy-4-(5-oxo-5,6,7,8-tetrahydro-quinolin-2-ylamino)-phenyl]-acetonitrile,
2-(3-Fluoro-4-pyridin-2-yl-phenylamino)-7,8-dihydro-6H-quinolin-5-one,
2-(3-Fluoro-4-pyridin-3-yl-phenylamino)-7,8-dihydro-6H-quinolin-5-one,
[2-Fluoro-4-(5-oxo-5,6,7,8-tetrahydro-quinolin-2-ylamino)-phenyl]-acetonitrile,
7,7-Dimethyl-2-(pyridin-3-ylamino)-7,8-dihydro-6H-quinolin-5-one,
7,7-Dimethyl-2-(pyridin-4-ylamino)-7,8-dihydro-6H-quinolin-5-one,
2-(3-Methoxy-4-pyridin-2-yl-phenylamino)-7,7-dimethyl-5-oxo-5,6,7,8-tetrahydro-quinoline-3-carbonitrile,
2-(3-Methoxy-4-pyridin-3-yl-phenylamino)-7,7-dimethyl-5-oxo-5,6,7,8-tetrahydro-quinoline-3-carbonitrile,
7,7-Dimethyl-5-oxo-2-(pyridin-4-ylamino)-5,6,7,8-tetrahydro-quinoline-3-carbonitrile,
7,7-Dimethyl-3-nitro-2-(pyridin-4-ylamino)-7,8-dihydro-6H-quinolin-5-one, and
2-(3,5-Dimethoxy-phenylamino)-7,7-dimethyl-7,8-dihydro-6H-quinolin-5-one,
and optical isomers, pharmaceutically-acceptable acid and base addition salts, and hydrates thereof.

72. A compound of claim 1 which is selected from:
2-Cyclopentylamino-7,7-dimethyl-5-oxo-5,6,7,8-tetrahydro-quinoline-3-carbonitrile,
2-Cyclohexylamino-5-oxo-5,6,7,8-tetrahydro-quinoline-3-carbonitrile,
2-(Adamantan-1-ylamino)-7,7-dimethyl-5-oxo-5,6,7,8-tetrahydro-quinoline-3-carbonitrile,
2-Cyclopentylamino-7,7-dimethyl-3-nitro-7,8-dihydro-6H-quinolin-5-one,
3-Chloro-2-cyclopentylamino-7,7-dimethyl-7,8-dihydro-6H-quinolin-5-one,
7,7-Dimethyl-5-oxo-2-(6,7,8,9-tetrahydro-5H-benzocyclohepten-7-ylamino)-5,6,7,8-tetrahydro-quinoline-3-carbonitrile,
2-(4-Methoxy-cyclohexylamino)-7,7-dimethyl-3-nitro-7,8-dihydro-6H-quinolin-5-one,
2-(4-Methoxy-cyclohexylamino)-7,7-dimethyl-3-nitro-7,8-dihydro-6H-quinolin-5-one,
2-(4-Methoxy-cyclohexylamino)-7,7-dimethyl-7,8-dihydro-6H-quinolin-5-one,
2-(4-Methoxy-cyclohexylamino)-7,7-dimethyl-5-oxo-5,6,7,8-tetrahydro-quinoline-3-carbonitrile,
2-(Cyclohexyl-methyl-amino)-7,8-dihydro-6H-quinolin-5-one, and
2-(Cyclohexyl-methyl-amino)-7,7-dimethyl-7,8-dihydro-6H-quinolin-5-one,
and optical isomers, pharmaceutically-acceptable acid and base addition salts, and hydrates thereof.

73. A compound of claim 1, which is selected from:
2-Azepan-1-yl-5-oxo-5,6,7,8-tetrahydro-quinoline-3-carbonitrile,
7,7-Dimethyl-5-oxo-2-(4-phenyl-piperazin-1-yl)-5,6,7,8-tetrahydro-quinoline-3-carbonitrile,
2-Azepan-1-yl-7,7-dimethyl-7,8-dihydro-6H-quinolin-5-one,
2-(4-Phenyl-piperazin-1-yl)-7,8-dihydro-6H-quinolin-5-one,
4-Chloro-5-oxo-2-(4-phenyl-piperazin-1-yl)-5,6,7,8-tetrahydro-quinoline-3-carbonitrile,
4-Bromo-5-oxo-2-(4-phenyl-piperazin-1-yl)-5,6,7,8-tetrahydro-quinoline-3-carbonitrile,
4-Methoxy-5-oxo-2-(4-phenyl-piperazin-1-yl)-5,6,7,8-tetrahydro-quinoline-3-carbonitrile,
4-Ethoxy-5-oxo-2-(4-phenyl-piperazin-1-yl)-5,6,7,8-tetrahydro-quinoline-3-carbonitrile,
4-Ethoxy-7,7-dimethyl-5-oxo-2-(4-phenyl-piperazin-1-yl)-5,6,7,8-tetrahydro-quinoline-3-carbonitrile,
4-Methoxy-7,7-dimethyl-5-oxo-2-(4-phenyl-piperazin-1-yl)-5,6,7,8-tetrahydro-quinoline-3-carbonitrile,
4-Chloro-7,7-dimethyl-5-oxo-2-(4-phenyl-piperazin-1-yl)-5,6,7,8-tetrahydro-quinoline-3-carbonitrile,
4-Bromo-7,7-dimethyl-5-oxo-2-(4-phenyl-piperazin-1-yl)-5,6,7,8-tetrahydro-quinoline-3-carbonitrile,
4-Bromo-7,7-dimethyl-5-oxo-2-(4-phenyl-piperidin-1-yl)-5,6,7,8-tetrahydro-quinoline-3-carbonitrile,
4-Chloro-7,7-dimethyl-5-oxo-2-(4-phenyl-piperidin-1-yl)-5,6,7,8-tetrahydro-quinoline-3-carbonitrile,
4-Methoxy-7,7-dimethyl-5-oxo-2-(4-phenyl-piperidin-1-yl)-5,6,7,8-tetrahydro-quinoline-3-carbonitrile,
4-Ethoxy-7,7-dimethyl-5-oxo-2-(4-phenyl-piperidin-1-yl)-5,6,7,8-tetrahydro-quinoline-3-carbonitrile,
4-(2-Hydroxy-ethoxy)-7,7-dimethyl-5-oxo-2-(4-phenyl-piperidin-1-yl)-5,6,7,8-tetrahydro-quinoline-3-carbonitrile,
3-Chloro-7,7-dimethyl-2-(4-phenyl-piperidin-1-yl)-7,8-dihydro-6H-quinolin-5-one,
3-Bromo-7,7-dimethyl-2-(4-phenyl-piperidin-1-yl)-7,8-dihydro-6H-quinolin-5-one,
3-Fluoro-7,7-dimethyl-2-(4-phenyl-piperidin-1-yl)-7,8-dihydro-6H-quinolin-5-one,
3-Methoxy-7,7-dimethyl-2-(4-phenyl-piperidin-1-yl)-7,8-dihydro-6H-quinolin-5-one,
7,7-Dimethyl-3-nitro-2-(4-phenyl-piperidin-1-yl)-7,8-dihydro-6H-quinolin-5-one,
7,7-Dimethyl-3-nitro-2-(4-phenyl-piperazin-1-yl)-7,8-dihydro-6H-quinolin-5-one,
3-Fluoro-7,7-dimethyl-2-(4-phenyl-piperazin-1-yl)-7,8-dihydro-6H-quinolin-5-one, 3-Bromo-7,7-dimethyl-2-(4-phenyl-piperazin-1-yl)-7,8-dihydro-6H-quinolin-5-one,
3-Chloro-7,7-dimethyl-2-(4-phenyl-piperazin-1-yl)-7,8-dihydro-6H-quinolin-5-one,
3-Methoxy-7,7-dimethyl-2-(4-phenyl-piperazin-1-yl)-7,8-dihydro-6H-quinolin-5-one,
2-[4-(4-Methoxy-phenyl)-piperazin-1-yl]-7,7-dimethyl-5-oxo-5,6,7,8-tetrahydro-quinoline-3-carbonitrile,
2-[4-(4-Fluoro-phenyl)-piperazin-1-yl]-7,7-dimethyl-5-oxo-5,6,7,8-tetrahydro-quinoline-3-carbonitrile,
3-[1-(5-Oxo-5,6,7,8-tetrahydro-quinolin-2-yl)-1H-imidazol-4-yl]-benzonitrile,
3-[1-(7,7-Dimethyl-5-oxo-5,6,7,8-tetrahydro-quinolin-2-yl)-1H-imidazol-4-yl]-benzonitrile,
3-[1-(7,7-Dimethyl-5-oxo-5,6,7,8-tetrahydro-quinolin-2-yl)-1H-imidazol-4-yl]-5-fluoro-benzonitrile,
7,7-Dimethyl-3-morpholin-4-yl-2-(4-phenyl-piperidin-1-yl)-7,8-dihydro-6H-quinolin-5-one,
7,7-Dimethyl-3-nitro-2-piperidin-1-yl-7,8-dihydro-6H-quinolin-5-one,
3-Chloro-7,7-dimethyl-2-piperidin-1-yl-7,8-dihydro-6H-quinolin-5-one,
3-Chloro-2-[4-(4-methoxy-phenyl)-piperazin-1-yl]-7,7-dimethyl-7,8-dihydro-6H-quinolin-5-one,
2-[4-(4-Methoxy-phenyl)-piperazin-1-yl]-7,7-dimethyl-3-nitro-7,8-dihydro-6H-quinolin-5-one,
2-[4-(4-Methoxy-phenyl)-piperidin-1-yl]-7,7-dimethyl-5-oxo-5,6,7,8-tetrahydro-quinoline-3-carbonitrile, and
7,7-Dimethyl-5-oxo-2-piperidin-1-yl-5,6,7,8-tetrahydro-quinoline-3-carbonitrile,
and optical isomers, pharmaceutically-acceptable acid and base addition salts, and hydrates thereof.

74. A compound of claim 1, which is selected from:
2-Phenylamino-6,7,8,9,9a,10-hexahydro-5aH-benzo[g]quinolin-5-one,
2-(1-Phenyl-ethylamino)-6,7,8,9,9a,10-hexahydro-5aH-benzo[g]quinolin-5-one,
2-(Cyclohexyl-methyl-amino)-6,7,8,9,9a,10-hexahydro-5aH-benzo[g]quinolin-5-one,
2-(4-Phenyl-piperazin-1-yl)-6,7,8,9,9a,10-hexahydro-5aH-benzo[g]quinolin-5-one,
3-(5-Oxo-5,5a,6,7,8,9,9a,10-octahydro-benzo[g]quinolin-2-yl)-benzonitrile,
2-Pyridin-3-yl-6,7,8,9,9a,10-hexahydro-5aH-benzo[g]quinolin-5-one,
2-Piperidin-1-yl-6,7,8,9,9a,10-hexahydro-5aH-benzo[g]quinolin-5-one, and
2-Adamantan-1-yl-6,7,8,9,9a,10-hexahydro-5aH-benzo[g]quinolin-5-one,
and optical isomers, pharmaceutically-acceptable acid and base addition salts, and hydrates thereof.

75. A compound of claim 1, which is 2-cyclopentylamino-7,7-dimethyl-5-oxo-5,6,7,8-tetrahydroquinoline-3-carbonitrile, or an optical isomer, pharmaceutically-acceptable acid or base addition salt, or hydrate thereof.

76. A compound of claim 1, which is 7,7-dimethyl-5-oxo-2-(4-phenyl-piperazin-1-yl)-5,6,7,8-tetrahydroquinoline-3-carbonitrile, or an optical isomer, pharmaceutically-acceptable acid or base addition salt, or hydrates thereof.

77. A pharmaceutical composition comprising as active ingredient a compound of claim 1 together with together with one or more pharmaceutically acceptable excipients or vehicles.

* * * * *

UNITED STATES PATENT AND TRADEMARK OFFICE
CERTIFICATE OF CORRECTION

| | | |
|---|---|---|
| PATENT NO. | : 7,598,384 B2 | |
| APPLICATION NO. | : 11/066899 | |
| DATED | : October 6, 2009 | |
| INVENTOR(S) | : Aigars Jirgensons et al. | |

It is certified that error appears in the above-identified patent and that said Letters Patent is hereby corrected as shown below:

Column 140, Line 28: "$C_{1-4}$" should be -- $C_{1-6}$ --.

Column 140, Line 54: "A compound Claim 19" should be -- A compound of Claim 19 --.

Column 150, Line 29: "ingredient a compound of claim 1 together with together with" should be
-- ingredient a compound of claim 1 together with --.

Signed and Sealed this
Tenth Day of May, 2011

David J. Kappos
*Director of the United States Patent and Trademark Office*